US008105773B2

(12) United States Patent
Sharma et al.

(10) Patent No.: US 8,105,773 B2
(45) Date of Patent: Jan. 31, 2012

(54) OLIGONUCLEOTIDES FOR CANCER DIAGNOSIS

(75) Inventors: Praveen Sharma, Oslo (NO); Anders Lönneborg, Aas (NO)

(73) Assignee: Diagenic AS, Olso (NO)

( * ) Notice: Subject to any disclaimer, the term of this patent is extended or adjusted under 35 U.S.C. 154(b) by 0 days.

(21) Appl. No.: 11/628,300

(22) PCT Filed: Jun. 2, 2005

(86) PCT No.: PCT/GB2005/002180
§ 371 (c)(1),
(2), (4) Date: Jul. 18, 2007

(87) PCT Pub. No.: WO2005/118851
PCT Pub. Date: Dec. 15, 2005

(65) Prior Publication Data
US 2008/0026385 A1 Jan. 31, 2008

(30) Foreign Application Priority Data
Jun. 2, 2004 (GB) .................................. 0412301.4

(51) Int. Cl.
C12Q 1/68 (2006.01)
C07H 21/02 (2006.01)
C07H 21/04 (2006.01)
(52) U.S. Cl. ..................... 435/6.1; 536/23.1; 536/24.3
(58) Field of Classification Search ............... 435/6, 7.1, 435/6.1; 536/23.1, 24.3; 530/350
See application file for complete search history.

(56) References Cited

U.S. PATENT DOCUMENTS

| | | | |
|---|---|---|---|
| 4,981,783 A | 1/1991 | Augenlicht | |
| 5,474,796 A | 12/1995 | Brennan | |
| 5,545,531 A | 8/1996 | Rava et al. | |
| 5,633,137 A | 5/1997 | Paul et al. | |
| 5,677,125 A | 10/1997 | Holt et al. | |
| 5,800,992 A | 9/1998 | Fodor et al. | |
| 5,830,645 A | 11/1998 | Pinkel et al. | |
| 5,871,928 A | 2/1999 | Fodor et al. | |
| 5,874,219 A | 2/1999 | Rava et al. | |
| 5,925,525 A | 7/1999 | Fodor et al. | |
| 5,994,076 A | 11/1999 | Chenchik et al. | |
| 6,004,755 A | 12/1999 | Wang | |
| 6,040,138 A | 3/2000 | Lockhart et al. | |
| 6,174,680 B1* | 1/2001 | Makrigiorgos | 435/6 |
| 6,190,857 B1 | 2/2001 | Ralph et al. | |
| 6,607,879 B1 | 8/2003 | Cocks et al. | |
| 6,864,100 B1* | 3/2005 | Ribbe et al. | 436/178 |
| 6,955,876 B2* | 10/2005 | Kane et al. | 435/6 |
| 7,108,969 B1* | 9/2006 | Warrington et al. | 435/6 |
| 7,118,853 B2* | 10/2006 | Botstein et al. | 435/4 |
| 7,229,774 B2* | 6/2007 | Chinnaiyan et al. | 435/7.1 |
| 7,306,921 B2* | 12/2007 | Nevalainen et al. | 435/7.1 |
| 7,335,467 B2* | 2/2008 | Scanlan et al. | 435/4 |
| 2002/0022222 A1 | 2/2002 | Sharma et al. | |
| 2002/0169560 A1 | 11/2002 | Hytopoulos et al. | |
| 2003/0068642 A1 | 4/2003 | Urnovitz | |
| 2003/0099973 A1* | 5/2003 | Wang et al. | 435/6 |
| 2003/0108896 A1* | 6/2003 | Vogt | 435/6 |
| 2003/0175736 A1 | 9/2003 | Chinnaiyan et al. | |
| 2003/0175753 A1* | 9/2003 | Shaughnessy et al. | 435/6 |
| 2003/0195431 A1* | 10/2003 | Sukhatme | 600/562 |
| 2003/0219760 A1 | 11/2003 | Gordon et al. | |
| 2003/0225526 A1* | 12/2003 | Golub et al. | 702/19 |
| 2003/0232350 A1 | 12/2003 | Afar et al. | |
| 2004/0005615 A1* | 1/2004 | Li et al. | 435/6 |
| 2004/0014059 A1 | 1/2004 | Liew | |
| 2004/0203023 A1* | 10/2004 | Chandrasiri Herath | 435/6 |
| 2004/0241653 A1* | 12/2004 | Feinstein et al. | 435/6 |
| 2004/0241726 A1 | 12/2004 | Liew | |
| 2004/0241727 A1 | 12/2004 | Liew | |
| 2004/0241728 A1 | 12/2004 | Liew | |
| 2004/0241729 A1 | 12/2004 | Liew | |
| 2004/0248169 A1 | 12/2004 | Liew | |
| 2004/0248170 A1 | 12/2004 | Liew | |
| 2004/0265868 A1 | 12/2004 | Liew | |
| 2004/0265869 A1 | 12/2004 | Liew | |
| 2005/0003394 A1 | 1/2005 | Liew | |
| 2005/0042630 A1 | 2/2005 | Liew | |
| 2005/0112630 A1* | 5/2005 | Shaughnessy et al. | 435/6 |
| 2006/0024692 A1* | 2/2006 | Nakamura et al. | 435/6 |
| 2006/0281081 A1* | 12/2006 | Nakamura et al. | 435/6 |
| 2007/0178503 A1* | 8/2007 | Jiang | 435/6 |
| 2009/0099087 A1* | 4/2009 | Kisiel et al. | 514/12 |
| 2009/0118132 A1* | 5/2009 | Haferlach et al. | 506/8 |
| 2009/0233276 A1* | 9/2009 | Kopreski | 435/6 |

FOREIGN PATENT DOCUMENTS

EP 0408918 A1 1/1991
(Continued)

OTHER PUBLICATIONS

Duggan et al., Expression profiling using cDNA microarrays. Nature Genetics 21 Supplemental : 10-14 (1999).*
Cole et al., The genetics of cancer—a 3D model. Nature Genetics 21 Supplemental : 38-41 (1999).*
Ono et al., Identification by cDNA microarray of Genes involved in Ovarian Carcinogenesis. Cancer Research 60 : 5007-5011 (2000).*
Okabe et al., Genome-wide analysis of gene expression in human hepatocellular carcinomas using cDNA microarray: Identification of genes involved in viral carcinogenesis and tumor progression. Cancer Research 61 : 2129-2137 (2001).*
Kitahara et al., Alterations of gene expression during colorectal carcinogenesis revealked by cDNA microarrays after laser-capture microdissection of tumor tissues and normal epithelia. Cancer Research 61 : 3544-3549 (2001).*
Inoue et al., Prognostic score of gastric cancer determined by cDNA microarray. Clinical Cancer Research 8 : 3475-3479 (2002).*

(Continued)

Primary Examiner — Ethan C Whisenant
(74) Attorney, Agent, or Firm — Sughrue Mion, PLLC

(57) ABSTRACT

The present invention provides sets of oligonucleotides corresponding to genes encoding proteins involved in protein synthesis and/or stability or genes encoding proteins involved in the regulation of defence and/or chromatin remodelling for use in preparing transcript patterns particularly for cancer diagnosis. The invention also extends to such sets and kits containing such sets as well as related methods reliant on analysis of marker polypeptides encoded by the genes to develop characteristic expression profiles.

49 Claims, 4 Drawing Sheets

FOREIGN PATENT DOCUMENTS

| | | |
|---|---|---|
| EP | 0534640 A1 | 3/1993 |
| EP | 0979308 A | 2/2000 |
| GB | 2260811 A | 4/1993 |
| WO | 9318143 A1 | 9/1993 |
| WO | 9520681 A1 | 8/1995 |
| WO | 9722720 A1 | 6/1997 |
| WO | 9727317 A1 | 7/1997 |
| WO | 9729212 A1 | 8/1997 |
| WO | 9808083 A1 | 2/1998 |
| WO | WO 98/49342 * | 4/1998 |
| WO | 9906831 A2 | 2/1999 |
| WO | 9944062 A1 | 9/1999 |
| WO | 9949083 A1 | 9/1999 |
| WO | 0004187 A2 | 1/2000 |
| WO | 0014281 A2 | 3/2000 |
| WO | 0022168 A1 | 4/2000 |
| WO | 0022172 A1 | 4/2000 |
| WO | 0024940 A1 | 5/2000 |
| WO | 0026412 A1 | 5/2000 |
| WO | 00/40749 A2 | 7/2000 |
| WO | 02057787 A2 | 7/2002 |
| WO | 02/059271 A2 | 8/2002 |
| WO | 02/059367 A2 | 8/2002 |
| WO | 02/070737 A2 | 9/2002 |
| WO | 2004/024892 A2 | 3/2004 |
| WO | 2004046382 A2 | 6/2004 |
| WO | 2004112589 A2 | 12/2004 |

OTHER PUBLICATIONS

Kitahara et al., Classification of sensitivity or resistance of cervical cancers to ionizing radiation according to expression profiles of 62 genes selected by cDNA microarray analysis. Neoplasia 4(4) : 295-303 (2002).*

Lin et al., Molecular diagnosis of colorectal tumors by expression profiles of 50 genes expressed differentially in adenomas and carcinomas. Oncogene 21 : 4120-4128 (2002).*

Churchill G.A., Fundamentals of experimental design for cDNA microarrays. Nature Genetics Supplement 32 : 490-495 (2002).*

Slonim, D.K., From patterns to pathways : gene expression data analysis comes of age. Nature Genetics Supplement 32 : 502-508 (2002).*

Chung et al., Molecular portraits and the family tree of cancer. Nature Genetics Supplement 32 : 533-540 (2002).*

Brooks, JD., Microarray analysis in prostate cancer research. Current Opinion in Urology 12 : 395-399 (2002).*

Bull et al., Identification of potential diagnostic markers of prostate cancer and prostatic intraepithelial neoplasia using cDNA microarray British J. of Cancer 84 (11) : 1512-1519 (2001).*

Dhanasekaran et al., Delineation of prognostic biomarkers in prostate cancer. Nature 412 : 822-826 (2001).*

Golub et al., Molecular classification of cancer: class discovery and class prediction by gene expression monitoring. Science 286 : 531-537 (1999).*

Huppi et al., Molecular profiling of prostate cancer. Current Urology Reports 5 45-51 (2004).*

Li et al., PGDB: a curated and integrated database of genes related to the prostate. Nucleic Acids Research 31 (1) : 291-293 (2003).*

Liotta ert al., Molecular profiling of human cancer. Nature Reviews/Genetics 1 : 48-56 (2000).*

Moul et al., cDNA microarray gene chip for prostate cancer and translational study in a prospective tissue bank and clinical longitudinal database. Prostate Cancer and Prostatic Dieseases 3 : Suppl.1 S30- (2000).*

Nelson PS., Predicting prostate cancer behavior using transcript profiles. J. of Urology 172 : 528-533 (2004).*

Singh et al., Gene expression correlates of clinical prostate cancer behavior. Cancer Cell 1 : 203-209 (2002).*

Walker et al., Prediction of Gene Function by Genome-Scale Expression Analysis: Prostate Cancer-Associated Genes. Genome Research 9 : 1198-1203 (1999).*

Zahn et al. Blood 99(5) : 1745-1757 (2002).*

Friend et al. Gene expression profiling predicts clinical outcome of breast cancer.Nature 415: 530-536 (2002).*

Friend et al., A gene expression signature as a predictor of survival in breast cancer. 347 (25) : 1999-2009 (2002).*

Liew et al., The peripheral blood transcriptome dynamically reflects system wide biology: a potentialdiagnostic tool, J. Lab. Clin. Med., 2006, 126-132, 147, Mosby, Inc.

Cheung et al., Natural variation in human gene expression assessed in lymphoblastoid cells, NatureGenetics, Mar. 2003, 422-425, vol. 33.

Wu, Analysing gene expression data from DNA microarrays to identify candidate genes, Journal of Pathology, 2001, 53-65, 195, John Wiley & Sons, Ltd.

Newton et al., On Differential Variability of Expression Ratios: Improving Statistical Inference aboutGene Expression Changes from Microarray Data, Journal of Computational Biology, 2001, 37-52, vol. 8, No. 1, Mary Ann Liebert, Inc.

Fujioka, ACTA Hepatol. Jpn., 34(12): 940-949 (1993).

Enderlin et al., Aging decreases the abundance of retinoic acid (RAR) and triiodothryonine (TR)nuclear receptor mRNA in rat brain: effect of the administration of retinoids, FEBS Letters, 1997, 629632, 412.

Schena et al., Parallel human genome analysis: Microarray-based expression monitoring of 1000 genes,Proc. Natl. Acad. Sci., Oct. 1996, 10614-10619, vol. 93.

Lonneborg et al, Construction of Subtractive cDNA Library Using Magentic Beads and PCR, PCRMethods and Applications, 1995, S168-S176, 4, Cold Spring Harbor Laboratory.

Zhi-Xin et al, Zhongguo Zhongliu Lichung, pp. 243-246 (1996).

Schena, Genome analysis with gene expression microarrays, BioEssays, 1996, 427-431, vol. 18, No. 5,ICSU Press.

Knoll et al., Characterization of Differentially Expressed Genes Following Brief Cardiac Ischemia,Biochemical and Biophysica Research Communications, 1996, 402-407, 221, Article No. 0608, AcademicPress, Inc.

Jonas et al., Identification of carcinoembryonic antigen-producing cells circulating in the blood ofpatients with colorectal carcinoma by reverse transcriptase polymerase chain reaction, GUT, 1996, 717721, 39.

Kruger et al., Reverse transcriptase/polymerase chain reaction detection of cytokeratin-19 mRNA inbone marrow and blood of breast cancer patients, J. Cancer Res. Clin. Oncol., 1996, 679-686, 122,Springer-Verlag.

Understanding the GEM Solution: Building a GEM Library, www.synteni.com/gemsol1.htm (1997).

Understanding the GEM Solution: Building a GEM Library, www.synteni.com/gemsol2.htm (1997).

Understanding the GEM Solution: Building a GEM Library, www.synteni.com/gemsol3.htm (1997).

Sample GEM Data, www.synteni.com/sample.htm (1997).

Schena et al., Quantitative Monitoring of Gene Expression Patterns with a Complementary DNAMicroarray, Science, Oct. 20, 1995, 467-470, vol. 270.

Urakami et al., Cu, Zn superoxide dismutase in patients with dementia of the Alzheimer type, Acta Neurol Scand, 1995, 165-168, 91.

Buckland et al., Amyloid precursor protein mRNA levels in the mononuclear blood cells ofAlzheimer's and Down's patients, Molecular Brain Research, 1991, 316-320, 18, Elsevier SciencePublishers B.V.

Ditkoff et al., Detection of circulating thyroid cells in peripheral blood, Surgery, 1996, 959-965, vol. 120, No. 6, Mosby-Year Book, Inc.

Graber et al., Isolation of Differntially Expressed Genes in Carcinoma of the Esophagus, Annals of Surgical Oncology, 1996, 192-197, 3(2), Lippincott-Raven Publishers.

Wadhwa et al., An Effective Elimination of False Positives Isolated from Differential Display ofmRNAs, Molecular Biotechnology, 1996, 213-217, vol. 6, Humana Press Inc.

Stratagene Catalog, p. 39 (1998).

Bauer et al., Identification of differentially expressed mRNA species by an improved display technique(DDRT-PCR), Nucleic Acids Research, 1993, 4272-4280, vol. 12, No. 18, Oxford University Press.

Heller et al., Discovery and analysis of inflammatory disease-related genes using cDNA microarrays,Proc. Natl. Acad. Sci., Mar. 1997, 2150-2155, vol. 94.

Shalon et al., A DNA Microarray System for Analyzing Complex DNA Samples Using Two-Color Fluorescent Probe Hybridization, Genome Research, 1996, 639-645, 6, Cold Spring Harbor Laboratory Press.

Bomprezzi et al, Gene Expression profile in multiple sclerosis patients and healthy controls: identifying pathways relet to disease; Human Molecular Genetics, 12(17):2191-2199 (2003).

Vernon et al, Utility blood for gene expression profiling and biomarker discovery in chronic fatigue syndrome; Disease Markers, 18:139-199 (2002).

Twine et al, Disease-associated expression profiles in peripheral blood mononuclear cells from patients with advanced renal cell carcinoma; Cancer Res., 63:6069-6075 (2003).

Hashida et al, Analysis of gene expression in peripheral blood eosinophils from patients with atopic dermatitis by differential display; Int.Arch. Allergy Immunol., 131(suppl 1)26-33 (2003).

Bro et al, On the difference between low-rank and subspace approximation: improved model for multi-linear PLS regression; Chemometrics and Intelligent Laboratory Systems, 58:3-13 (2001).

Golub et al, Molecular classification of cancer: class discovery and class prediction by gene expression monitoring; Science, 286:531-537 (1999).

Wasserman et al, Identification of regulatory regions which confer muscle-specfic gene expression; J. Mol. Biol., 278:167-181 (1998).

Sherlock, Analysis of large-scale gene expression data; Immunological Techniques, pp. 201-205.

Heyer et al, Exploring expression data: Identification and analysis of coexpressed genes; Genome Research, 9:1106-1115 (1999).

Hardy et al, Double-case diagnostic fro outliers indentification; Chemometrics and Intelligent Laboratory Systems, 34:117-129 (1996).

Lukas et al. Identification and characterization of genes differentially expressed in breast ductal carcinoma; (Journal of Investigative Medicine, 1997, vol. 45, No. 1, p. 132A).

Database GEO Profiles Online! NCBI; Jan. 2, 2004, "http://www.ncbi.nih.gov/projects/geo/query/acc.cgi?acc=GPL887".

Alizadeh A A et al: "Distinct Types of Diffuse Large B-Cell Lymphoma Identified by Gene Expression Profiling Nature", Nature, vol. 403, Feb. 3, 2000,pp. 503-512.

Brooks et al: "Transcript Profiles of Microdissected Tissue in a Mouse Model of Idiopathic Parkinson's disease Using the Ribo-SPIATM Amplification Process" Online! Nov. 2003, p. 1.

Vivian G. Cheung et al., "Natural variation in human gene expression assessed in lymphoblastoid cells", Nature Genetics, 2003, 33: 422-425.

Thomas D. Wu, "Analysing gene expression data from DNA microarrays to identify candidate genes", Journal of Pathology, 2001, 195: 53-65.

M.A. Newton et al., "On Differential Variability of Expression Ratios: Improving Statistical Inference about Gene Expression Changes from Microarray Data", Journal of Computational Biology, 2001, 8(1): 37-52.

André Ahr et al., "Molecular classification of breast cancer patients by gene expression profiling", Journal of Pathology, 2001, 195: 312-320.

Sorin Draghici et al., "Reliability and reproducibility issues in DNA microarray measurements", Trends in Genetics, 2006, 22(2): 101-109.

Maria C. Grekova et al., "Deficient Expression in Multiple Sclerosis of the Inhibitory Transcription Factor Sp3 in Mononuclear Blood Cells", Annals of Neurology., 1996, 40(1): 108-112.

Campbell, Biology, Fourth Edition, 1996, Chapter 38: Circulation and Gas Exchange, p. 833.

Adeline R. Whitney et al., "Individuality and variation in gene expression patterns in human blood", PNAS, 2003, 100(4): 1896-1901.

US 6,066,453, 05/2000, Pinkel et al. (withdrawn)

* cited by examiner

```
                              SEQUENCE LISTING

<160> NUMBER OF SEQ ID NOS: 146

<210> SEQ ID NO 1
<211> LENGTH: 60
<212> TYPE: DNA
<213> ORGANISM: Unknown
<220> FEATURE:
<223> OTHER INFORMATION: probe 1

<400> SEQUENCE: 1
tttacttcta cctgctcttc cccaactccc tgagcctgag tgagcgtgtg gccatcatca      60

<210> SEQ ID NO 2
<211> LENGTH: 60
<212> TYPE: DNA
<213> ORGANISM: Unknown
<220> FEATURE:
<223> OTHER INFORMATION: probe 2

<400> SEQUENCE: 2
actccagact gggaagacct ttccattttc aggatcgacg cttcacgttg aggggagggc      60

<210> SEQ ID NO 3
<211> LENGTH: 60
<212> TYPE: DNA
<213> ORGANISM: Unknown
<220> FEATURE:
<223> OTHER INFORMATION: probe 3

<400> SEQUENCE: 3
ttaccaaact caaagcttat ttgagtagaa tgggctcatg ggcaatgtga tgttccctgt      60
```

```
<210> SEQ ID NO 4
<211> LENGTH: 60
<212> TYPE: DNA
<213> ORGANISM: Unknown
<220> FEATURE:
<223> OTHER INFORMATION: probe 4

<400> SEQUENCE: 4
tgggcctcaa aatggagatg gatcccaggt cttgtgggac cctgggatgt ttggggactt      60

<210> SEQ ID NO 5
<211> LENGTH: 60
<212> TYPE: DNA
<213> ORGANISM: Unknown
<220> FEATURE:
<223> OTHER INFORMATION: probe 5

<400> SEQUENCE: 5
tgttggttgg aggacaagtg ggcactgaga ccctggtgac ccatggaaag ggtgggcctg      60

<210> SEQ ID NO 6
<211> LENGTH: 60
<212> TYPE: DNA
<213> ORGANISM: Unknown
<220> FEATURE:
<223> OTHER INFORMATION: probe 6

<400> SEQUENCE: 6
tggagaaagg accctggacc tgtgggtcca tcgtccgttc caggagcagg caggctgggg      60

<210> SEQ ID NO 7
<211> LENGTH: 60
<212> TYPE: DNA
<213> ORGANISM: Unknown
<220> FEATURE:
<223> OTHER INFORMATION: probe 7

<400> SEQUENCE: 7
taatatcccc aaacctgaga tgagcactac gatggcagag agcagcctgt tggacctgct      60

<210> SEQ ID NO 8
<211> LENGTH: 60
<212> TYPE: DNA
<213> ORGANISM: Unknown
<220> FEATURE:
<223> OTHER INFORMATION: probe 8

<400> SEQUENCE: 8
tggacattcg aacagagttc aagaagcatt atggctattc cctatattca gcaattaaat      60

<210> SEQ ID NO 9
<211> LENGTH: 60
<212> TYPE: DNA
<213> ORGANISM: Unknown
<220> FEATURE:
<223> OTHER INFORMATION: probe 9

<400> SEQUENCE: 9
gactgaaaaa tcagctttct atttacatga aacactttgg gggtcatggg agtgcacagc      60

<210> SEQ ID NO 10
<211> LENGTH: 60
<212> TYPE: DNA
<213> ORGANISM: Unknown
<220> FEATURE:
<223> OTHER INFORMATION: probe 10
```

```
<400> SEQUENCE: 10
atcagaagtc cactgaactg cttattcgta aactaccttt ccagcgcctg gtgcgcgaga      60

<210> SEQ ID NO 11
<211> LENGTH: 60
<212> TYPE: DNA
<213> ORGANISM: Unknown
<220> FEATURE:
<223> OTHER INFORMATION: probe 11

<400> SEQUENCE: 11
agggataatt caaactgaca acctgtgcag tcccgtggag ggtaggggag tgtgggtgat      60

<210> SEQ ID NO 12
<211> LENGTH: 60
<212> TYPE: DNA
<213> ORGANISM: Unknown
<220> FEATURE:
<223> OTHER INFORMATION: probe 12

<400> SEQUENCE: 12
taaattatga tttactctgt gctgtttcca aattgggacc aggagagaaa tatgaacttc      60

<210> SEQ ID NO 13
<211> LENGTH: 60
<212> TYPE: DNA
<213> ORGANISM: Unknown
<220> FEATURE:
<223> OTHER INFORMATION: probe 13

<400> SEQUENCE: 13
tttgtggaaa ctgtgtgtta tactttgtgg tatagactgc ctgtttagta tgaaggggcg      60

<210> SEQ ID NO 14
<211> LENGTH: 60
<212> TYPE: DNA
<213> ORGANISM: Unknown
<220> FEATURE:
<223> OTHER INFORMATION: probe 14

<400> SEQUENCE: 14
tctattattt ataacttcag acttgggccc cctgttcttt ctttcccatt aacttgagtg      60

<210> SEQ ID NO 15
<211> LENGTH: 60
<212> TYPE: DNA
<213> ORGANISM: Unknown
<220> FEATURE:
<223> OTHER INFORMATION: probe 15

<400> SEQUENCE: 15
aacattttac ttctgcgctt ctatgtttgg gaaacattgc tctgataaaa aatagctgtc      60

<210> SEQ ID NO 16
<211> LENGTH: 60
<212> TYPE: DNA
<213> ORGANISM: Unknown
<220> FEATURE:
<223> OTHER INFORMATION: probe 16

<400> SEQUENCE: 16
cctcccagca gttaagtaac ttgtgtgaag atgggaccct tgttcctaat ggttctagaa      60

<210> SEQ ID NO 17
<211> LENGTH: 60
```

```
<212> TYPE: DNA
<213> ORGANISM: Unknown
<220> FEATURE:
<223> OTHER INFORMATION: probe 17

<400> SEQUENCE: 17
ctgaatctgt tttgtcttcc taatctatca caattgccac ccatcgggtt ttgggtgtgt       60

<210> SEQ ID NO 18
<211> LENGTH: 60
<212> TYPE: DNA
<213> ORGANISM: Unknown
<220> FEATURE:
<223> OTHER INFORMATION: probe 18

<400> SEQUENCE: 18
ccatgtttct gaatcttctt tgtttcaaat ggtgctgcat gttttcaact acaataagtg       60

<210> SEQ ID NO 19
<211> LENGTH: 60
<212> TYPE: DNA
<213> ORGANISM: Unknown
<220> FEATURE:
<223> OTHER INFORMATION: probe 19

<400> SEQUENCE: 19
atcattcaga atctgaaaag aaattcttct tattttctgg ggctgtcaga tccaggggt        60

<210> SEQ ID NO 20
<211> LENGTH: 60
<212> TYPE: DNA
<213> ORGANISM: Unknown
<220> FEATURE:
<223> OTHER INFORMATION: probe 20

<400> SEQUENCE: 20
ccaccgagct gctgatcaga aagctgcctt ttcagcgtct ggtgcgtgag atcgcgcagg       60

<210> SEQ ID NO 21
<211> LENGTH: 60
<212> TYPE: DNA
<213> ORGANISM: Unknown
<220> FEATURE:
<223> OTHER INFORMATION: probe 21

<400> SEQUENCE: 21
ctgagagttt ttgcagaaat ggggcagagg gacaccettt gggcgtggct tcctggtgat       60

<210> SEQ ID NO 22
<211> LENGTH: 60
<212> TYPE: DNA
<213> ORGANISM: Unknown
<220> FEATURE:
<223> OTHER INFORMATION: probe 22

<400> SEQUENCE: 22
cgagtggctc actcagaatt cttcattgat gggctaggga ccctactcgt ggggtcatgc       60

<210> SEQ ID NO 23
<211> LENGTH: 60
<212> TYPE: DNA
<213> ORGANISM: Unknown
<220> FEATURE:
<223> OTHER INFORMATION: probe 23

<400> SEQUENCE: 23
tctgttgatg accttggatg ctgtaaagtg attcgtcata gtctctgggg tacccatgta       60
```

```
<210> SEQ ID NO 24
<211> LENGTH: 60
<212> TYPE: DNA
<213> ORGANISM: Unknown
<220> FEATURE:
<223> OTHER INFORMATION: probe 24

<400> SEQUENCE: 24
tctcagaaga atgttggcca tgagactatc attcagagga ggagggatt tctctcttca      60

<210> SEQ ID NO 25
<211> LENGTH: 60
<212> TYPE: DNA
<213> ORGANISM: Unknown
<220> FEATURE:
<223> OTHER INFORMATION: probe 25

<400> SEQUENCE: 25
aagcggctgg caactgaagg ctggaacact tgctactgga taatcgtagc ttttaatgtt      60

<210> SEQ ID NO 26
<211> LENGTH: 60
<212> TYPE: DNA
<213> ORGANISM: Unknown
<220> FEATURE:
<223> OTHER INFORMATION: probe 26

<400> SEQUENCE: 26
aatcctgtga ttctgtgtgt gcctgtgtgt gtatgctgtt aataagataa ggctgcccat      60

<210> SEQ ID NO 27
<211> LENGTH: 60
<212> TYPE: DNA
<213> ORGANISM: Unknown
<220> FEATURE:
<223> OTHER INFORMATION: probe 27

<400> SEQUENCE: 27
gatggctgaa ggagctctat gaccatgctg aagccacgat cgtcgtcatg ctcgtgggta      60

<210> SEQ ID NO 28
<211> LENGTH: 60
<212> TYPE: DNA
<213> ORGANISM: Unknown
<220> FEATURE:
<223> OTHER INFORMATION: probe 28

<400> SEQUENCE: 28
tgcatgggga gtacattcat ctggaggctg cgtcctgatg aatgtcctgt ctgctggggt      60

<210> SEQ ID NO 29
<211> LENGTH: 60
<212> TYPE: DNA
<213> ORGANISM: Unknown
<220> FEATURE:
<223> OTHER INFORMATION: probe 29

<400> SEQUENCE: 29
gtttttgagt ttttgcagtt cagtatccct ctgtctattc acacttcgtg ttagtggtaa      60

<210> SEQ ID NO 30
<211> LENGTH: 60
<212> TYPE: DNA
<213> ORGANISM: Unknown
<220> FEATURE:
<223> OTHER INFORMATION: probe 30
```

<400> SEQUENCE: 30
gaggagctct tttctagaga gccgggagtt ggggaggggg tatttatttt gttatttatt     60

<210> SEQ ID NO 31
<211> LENGTH: 60
<212> TYPE: DNA
<213> ORGANISM: Unknown
<220> FEATURE:
<223> OTHER INFORMATION: probe 31

<400> SEQUENCE: 31
cagtttatgg atgtctgggc aatcatagca cttgccattt aaaaacatgc tacaggggca     60

<210> SEQ ID NO 32
<211> LENGTH: 60
<212> TYPE: DNA
<213> ORGANISM: Unknown
<220> FEATURE:
<223> OTHER INFORMATION: probe 32

<400> SEQUENCE: 32
attatcaact cactggtaac aacagtattc atgctcatcg tatctgtgtt ggcactgata     60

<210> SEQ ID NO 33
<211> LENGTH: 60
<212> TYPE: DNA
<213> ORGANISM: Unknown
<220> FEATURE:
<223> OTHER INFORMATION: probe 33

<400> SEQUENCE: 33
cctctgactg cctccaacgt aaaaatgtaa atataaattt ggttgagatc tggagggggg     60

<210> SEQ ID NO 34
<211> LENGTH: 60
<212> TYPE: DNA
<213> ORGANISM: Unknown
<220> FEATURE:
<223> OTHER INFORMATION: probe 34

<400> SEQUENCE: 34
gaaaccggat cgcaagcttc ccaggattcc tcttcgtgct gctggggtg ggaagcatgg     60

<210> SEQ ID NO 35
<211> LENGTH: 60
<212> TYPE: DNA
<213> ORGANISM: Unknown
<220> FEATURE:
<223> OTHER INFORMATION: probe 35

<400> SEQUENCE: 35
tcaatttcaa ggcctccctg cctctactag gcgccttagc tcactatggg gaaccacttg     60

<210> SEQ ID NO 36
<211> LENGTH: 60
<212> TYPE: DNA
<213> ORGANISM: Unknown
<220> FEATURE:
<223> OTHER INFORMATION: probe 36

<400> SEQUENCE: 36
gccacactgg ctttaggacc tgttgacacg gagggggtt tttaatttgg tttttaacaa     60

<210> SEQ ID NO 37
<211> LENGTH: 60

```
<212> TYPE: DNA
<213> ORGANISM: Unknown
<220> FEATURE:
<223> OTHER INFORMATION: probe 37

<400> SEQUENCE: 37
caaaatagct acatccctga acacagtccg gaatattacg gccggaccag ggaatcggga      60

<210> SEQ ID NO 38
<211> LENGTH: 60
<212> TYPE: DNA
<213> ORGANISM: Unknown
<220> FEATURE:
<223> OTHER INFORMATION: probe 38

<400> SEQUENCE: 38
aacaaactac agttttaccg tgtgtttgcc atttgagctg tgtggtgggc aggggctgg       60

<210> SEQ ID NO 39
<211> LENGTH: 60
<212> TYPE: DNA
<213> ORGANISM: Unknown
<220> FEATURE:
<223> OTHER INFORMATION: probe 39

<400> SEQUENCE: 39
agagaggatg gctgtattcc tatcccagct caagctgcca gcagcaatgt tggctgccca      60

<210> SEQ ID NO 40
<211> LENGTH: 60
<212> TYPE: DNA
<213> ORGANISM: Unknown
<220> FEATURE:
<223> OTHER INFORMATION: probe 40

<400> SEQUENCE: 40
ttaattctat tggctcttag tcacttggaa ctgattaatt ctgactttct gtcactaagc      60

<210> SEQ ID NO 41
<211> LENGTH: 60
<212> TYPE: DNA
<213> ORGANISM: Unknown
<220> FEATURE:
<223> OTHER INFORMATION: probe 41

<400> SEQUENCE: 41
gtctcaaaca gccgaaacct gtcttgcaat gggggagggg ggcgtttcgc tttccttctt      60

<210> SEQ ID NO 42
<211> LENGTH: 60
<212> TYPE: DNA
<213> ORGANISM: Unknown
<220> FEATURE:
<223> OTHER INFORMATION: probe 42

<400> SEQUENCE: 42
ttggctttta gacattatat atattatcag agaagtagcc tagtggtcgt ggggcacaga      60

<210> SEQ ID NO 43
<211> LENGTH: 60
<212> TYPE: DNA
<213> ORGANISM: Unknown
<220> FEATURE:
<223> OTHER INFORMATION: probe 43

<400> SEQUENCE: 43
aattttcaag acttcttttc actctttgat ttggatctgg caaattgggg aggggatgct      60
```

<210> SEQ ID NO 44
<211> LENGTH: 60
<212> TYPE: DNA
<213> ORGANISM: Unknown
<220> FEATURE:
<223> OTHER INFORMATION: probe 44

<400> SEQUENCE: 44
ttgcccaact gaccgtgggc tgaacacacg ttctgcttga ctcatttagg ggggagggaa    60

<210> SEQ ID NO 45
<211> LENGTH: 60
<212> TYPE: DNA
<213> ORGANISM: Unknown
<220> FEATURE:
<223> OTHER INFORMATION: probe 45

<400> SEQUENCE: 45
ggaacactgt gaaagttact tggggagggt gggccggtgg ggccgtagct ctctacctct    60

<210> SEQ ID NO 46
<211> LENGTH: 60
<212> TYPE: DNA
<213> ORGANISM: Unknown
<220> FEATURE:
<223> OTHER INFORMATION: probe 46

<400> SEQUENCE: 46
atgaggtgat cactgtgttc agtgttgttg gaatggattc agactggcta atggggaaa    60

<210> SEQ ID NO 47
<211> LENGTH: 60
<212> TYPE: DNA
<213> ORGANISM: Unknown
<220> FEATURE:
<223> OTHER INFORMATION: probe 47

<400> SEQUENCE: 47
tcagacagag cttggtaagt gacccctctt agaactattt ctcctcaggg ccgggtccag    60

<210> SEQ ID NO 48
<211> LENGTH: 60
<212> TYPE: DNA
<213> ORGANISM: Unknown
<220> FEATURE:
<223> OTHER INFORMATION: probe 48

<400> SEQUENCE: 48
gggggagatc agaatcgtcc agctgggctt cgacttggat gcccatggaa ttatcttcac    60

<210> SEQ ID NO 49
<211> LENGTH: 60
<212> TYPE: DNA
<213> ORGANISM: Unknown
<220> FEATURE:
<223> OTHER INFORMATION: probe 49

<400> SEQUENCE: 49
aggttgaact cttttttgtt gctcaagttc taggagtccc tttcctgaat atatacttgt    60

<210> SEQ ID NO 50
<211> LENGTH: 60
<212> TYPE: DNA
<213> ORGANISM: Unknown
<220> FEATURE:
<223> OTHER INFORMATION: probe 50

```
<400> SEQUENCE: 50
aatcttctga acggcataag tcctatttta gccttacctc ctgcatttgc aatacgtaat    60

<210> SEQ ID NO 51
<211> LENGTH: 60
<212> TYPE: DNA
<213> ORGANISM: Unknown
<220> FEATURE:
<223> OTHER INFORMATION: probe 51

<400> SEQUENCE: 51
cgaacaaaca aaatacttgg cggggcccga gagggctcgt ttggcctatt cgttggggat    60

<210> SEQ ID NO 52
<211> LENGTH: 60
<212> TYPE: DNA
<213> ORGANISM: Unknown
<220> FEATURE:
<223> OTHER INFORMATION: probe 52

<400> SEQUENCE: 52
ctactttaga gtcttctcca atgtccaaaa ggctaggggg ttggaggtgg ggactctgga    60

<210> SEQ ID NO 53
<211> LENGTH: 60
<212> TYPE: DNA
<213> ORGANISM: Unknown
<220> FEATURE:
<223> OTHER INFORMATION: probe 53

<400> SEQUENCE: 53
atagtcatgg gtgtcatgaa aaataccaa atgtaagaga acctccaagt cagggcgcag    60

<210> SEQ ID NO 54
<211> LENGTH: 60
<212> TYPE: DNA
<213> ORGANISM: Unknown
<220> FEATURE:
<223> OTHER INFORMATION: probe 54

<400> SEQUENCE: 54
acagaaaaca gacttgtaaa aagcttagat catcaagtgt tttggattgg gggcctccca    60

<210> SEQ ID NO 55
<211> LENGTH: 60
<212> TYPE: DNA
<213> ORGANISM: Unknown
<220> FEATURE:
<223> OTHER INFORMATION: probe 55

<400> SEQUENCE: 55
gacattgaga aggaaaaccg ggaggtggga gactggcgca agaatatcga tgcactaagt    60

<210> SEQ ID NO 56
<211> LENGTH: 60
<212> TYPE: DNA
<213> ORGANISM: Unknown
<220> FEATURE:
<223> OTHER INFORMATION: probe 56

<400> SEQUENCE: 56
tgcagaatgc ataagatgaa cattgcatga ccggatcatt ttagtgtctt tgcgttaaaa    60

<210> SEQ ID NO 57
<211> LENGTH: 60
```

```
<212> TYPE: DNA
<213> ORGANISM: Unknown
<220> FEATURE:
<223> OTHER INFORMATION: probe 57

<400> SEQUENCE: 57
tgaagatcat gaagaagcag ggcctctacc tacaaaagtg aatcttgctc attctgaaat      60

<210> SEQ ID NO 58
<211> LENGTH: 60
<212> TYPE: DNA
<213> ORGANISM: Unknown
<220> FEATURE:
<223> OTHER INFORMATION: probe 58

<400> SEQUENCE: 58
catattccat ttttaagaag aggtgttcca gttctgcatc tgataccgtc tcctttccct      60

<210> SEQ ID NO 59
<211> LENGTH: 60
<212> TYPE: DNA
<213> ORGANISM: Unknown
<220> FEATURE:
<223> OTHER INFORMATION: probe 59

<400> SEQUENCE: 59
ctggatgttt acctggagac cgagagccat gacgacagtg tggaggggcc caaggaattt      60

<210> SEQ ID NO 60
<211> LENGTH: 60
<212> TYPE: DNA
<213> ORGANISM: Unknown
<220> FEATURE:
<223> OTHER INFORMATION: probe 60

<400> SEQUENCE: 60
gaaaatccct tgctatgtct ttcctactag aaatgttcta gaatcgctgg acgtgtgggt      60

<210> SEQ ID NO 61
<211> LENGTH: 60
<212> TYPE: DNA
<213> ORGANISM: Unknown
<220> FEATURE:
<223> OTHER INFORMATION: probe 61

<400> SEQUENCE: 61
tggtggtgga tcctggaatt ttctcacgca ggagccattg ctctcctaga gggggtctca      60

<210> SEQ ID NO 62
<211> LENGTH: 60
<212> TYPE: DNA
<213> ORGANISM: Unknown
<220> FEATURE:
<223> OTHER INFORMATION: probe 62

<400> SEQUENCE: 62
ttaatgcttt atactgccga gtctgggggc ttgttttggt ttgggggcag ccatcctcca      60

<210> SEQ ID NO 63
<211> LENGTH: 60
<212> TYPE: DNA
<213> ORGANISM: Unknown
<220> FEATURE:
<223> OTHER INFORMATION: probe 63

<400> SEQUENCE: 63
ggctctttgt ggaggaaact aaacattccc ttgatggtct caagctatga tcagaagact      60
```

<210> SEQ ID NO 64
<211> LENGTH: 60
<212> TYPE: DNA
<213> ORGANISM: Unknown
<220> FEATURE:
<223> OTHER INFORMATION: probe 64

<400> SEQUENCE: 64
tctaggacta attcacactg caacaaaggg gctgattaga gcttttgaag atgggggat     60

<210> SEQ ID NO 65
<211> LENGTH: 60
<212> TYPE: DNA
<213> ORGANISM: Unknown
<220> FEATURE:
<223> OTHER INFORMATION: probe 65

<400> SEQUENCE: 65
gacttaacca cgtcagagga aggactttgg caagtgatat tgtcttcatg tggggtatta     60

<210> SEQ ID NO 66
<211> LENGTH: 60
<212> TYPE: DNA
<213> ORGANISM: Unknown
<220> FEATURE:
<223> OTHER INFORMATION: probe 66

<400> SEQUENCE: 66
ctgtcaaatt gccacgatct cactaaagga tttctatttg ctgtcagtta aaaataaagc     60

<210> SEQ ID NO 67
<211> LENGTH: 60
<212> TYPE: DNA
<213> ORGANISM: Unknown
<220> FEATURE:
<223> OTHER INFORMATION: probe 67

<400> SEQUENCE: 67
tgaagctatt tctgggagcc cagaagaaat gctcttttgc ttggagtttg tcatcctaca     60

<210> SEQ ID NO 68
<211> LENGTH: 60
<212> TYPE: DNA
<213> ORGANISM: Unknown
<220> FEATURE:
<223> OTHER INFORMATION: probe 68

<400> SEQUENCE: 68
ttggtttcct ctagggtgat attcgtcatt actctgtctc ttcaatccat ccagctaaat     60

<210> SEQ ID NO 69
<211> LENGTH: 60
<212> TYPE: DNA
<213> ORGANISM: Unknown
<220> FEATURE:
<223> OTHER INFORMATION: probe 69

<400> SEQUENCE: 69
aagaaaacac acctcggcga caatgtcttg ctgctcggat taggtggggg atgggcgaca     60

<210> SEQ ID NO 70
<211> LENGTH: 60
<212> TYPE: DNA
<213> ORGANISM: Unknown
<220> FEATURE:
<223> OTHER INFORMATION: probe 70

```
<400> SEQUENCE: 70
ctgagtttgc cttgttaatc ttcaatagtt ttacctaccc cagtctttgg aaccctaaat      60

<210> SEQ ID NO 71
<211> LENGTH: 60
<212> TYPE: DNA
<213> ORGANISM: Unknown
<220> FEATURE:
<223> OTHER INFORMATION: probe 71

<400> SEQUENCE: 71
aaagtgtcaa gtgattaagt gtgtatttgt accctagatg atatgaacca gcagtcttgt      60

<210> SEQ ID NO 72
<211> LENGTH: 60
<212> TYPE: DNA
<213> ORGANISM: Unknown
<220> FEATURE:
<223> OTHER INFORMATION: probe 72

<400> SEQUENCE: 72
tgagctgttc ccttctctaa gccataatct cttagtggat tgagccctct tggaaagact      60

<210> SEQ ID NO 73
<211> LENGTH: 60
<212> TYPE: DNA
<213> ORGANISM: Unknown
<220> FEATURE:
<223> OTHER INFORMATION: probe 73

<400> SEQUENCE: 73
tgttattggc ctagagctac acgtatatgg gtttgtcctg agtccgtttt caaatgacct      60

<210> SEQ ID NO 74
<211> LENGTH: 60
<212> TYPE: DNA
<213> ORGANISM: Unknown
<220> FEATURE:
<223> OTHER INFORMATION: probe 74

<400> SEQUENCE: 74
tcatctgcac tcaacattta atcgtgtcct tgctgtcttt ttattttcct ttttgtttgt      60

<210> SEQ ID NO 75
<211> LENGTH: 60
<212> TYPE: DNA
<213> ORGANISM: Unknown
<220> FEATURE:
<223> OTHER INFORMATION: probe 75

<400> SEQUENCE: 75
gcgggaggag cggccgctga tggtgttcaa cgtcaagtag cgcccgcgca gggcggggca      60

<210> SEQ ID NO 76
<211> LENGTH: 60
<212> TYPE: DNA
<213> ORGANISM: Unknown
<220> FEATURE:
<223> OTHER INFORMATION: probe 76

<400> SEQUENCE: 76
cctgttctgt ttttgctttt cctcttcttg accaaagcat gtgccactag ctgtccttga      60

<210> SEQ ID NO 77
<211> LENGTH: 60
```

```
<212> TYPE: DNA
<213> ORGANISM: Unknown
<220> FEATURE:
<223> OTHER INFORMATION: probe 77

<400> SEQUENCE: 77
ctgtctccct gtttgtgtaa acatactaga gtatactgcg gcgtgttttc tgtctaccca      60

<210> SEQ ID NO 78
<211> LENGTH: 60
<212> TYPE: DNA
<213> ORGANISM: Unknown
<220> FEATURE:
<223> OTHER INFORMATION: probe 78

<400> SEQUENCE: 78
gagagtttct tttaaataat cagcgggtgt tggtgatttg tagcccttct gcccttaaat      60

<210> SEQ ID NO 79
<211> LENGTH: 60
<212> TYPE: DNA
<213> ORGANISM: Unknown
<220> FEATURE:
<223> OTHER INFORMATION: probe 79

<400> SEQUENCE: 79
atactttgtg agttcacctg tctttatact caaaagtgtc ccttaatagt gtccttgccc      60

<210> SEQ ID NO 80
<211> LENGTH: 60
<212> TYPE: DNA
<213> ORGANISM: Unknown
<220> FEATURE:
<223> OTHER INFORMATION: probe 80

<400> SEQUENCE: 80
ttgaaggcaa agatcatcaa tatctgcatc tggctgctgt cgtcatctgt tggcatctct      60

<210> SEQ ID NO 81
<211> LENGTH: 60
<212> TYPE: DNA
<213> ORGANISM: Unknown
<220> FEATURE:
<223> OTHER INFORMATION: probe 81

<400> SEQUENCE: 81
acctttgaat ttgcggatgc tgaggaggat gatgaggtca aggtgtgagg ggctggggca      60

<210> SEQ ID NO 82
<211> LENGTH: 60
<212> TYPE: DNA
<213> ORGANISM: Unknown
<220> FEATURE:
<223> OTHER INFORMATION: probe 82

<400> SEQUENCE: 82
tattagacta tgtcatcaat ttttgcaaag gtaaatttga cttccttgaa cggctctcag      60

<210> SEQ ID NO 83
<211> LENGTH: 60
<212> TYPE: DNA
<213> ORGANISM: Unknown
<220> FEATURE:
<223> OTHER INFORMATION: probe 83

<400> SEQUENCE: 83
aaatactggg tggcttggtt tagagctaat tgtagtggaa gcctgcaagg ttgaggggtg      60
```

<210> SEQ ID NO 84
<211> LENGTH: 60
<212> TYPE: DNA
<213> ORGANISM: Unknown
<220> FEATURE:
<223> OTHER INFORMATION: probe 84

<400> SEQUENCE: 84
actcactatg gccagaaagc aatcttgttt ctcccctgc cagtctcttc tgattaaaga    60

<210> SEQ ID NO 85
<211> LENGTH: 60
<212> TYPE: DNA
<213> ORGANISM: Unknown
<220> FEATURE:
<223> OTHER INFORMATION: probe 85

<400> SEQUENCE: 85
aacaaatatt tattttgcac tctctttgcg gcactctggg ggcggtgggg tgcgtggggg    60

<210> SEQ ID NO 86
<211> LENGTH: 60
<212> TYPE: DNA
<213> ORGANISM: Unknown
<220> FEATURE:
<223> OTHER INFORMATION: probe 86

<400> SEQUENCE: 86
caagttgtca ctggagatgc gcgcggactt ggcccaaaac gtgcttctct gcggtgggtc    60

<210> SEQ ID NO 87
<211> LENGTH: 60
<212> TYPE: DNA
<213> ORGANISM: Unknown
<220> FEATURE:
<223> OTHER INFORMATION: probe 87

<400> SEQUENCE: 87
gatttccctg acccaattca gagattcttt atgcaaaagt gagttcagtc catctctata    60

<210> SEQ ID NO 88
<211> LENGTH: 60
<212> TYPE: DNA
<213> ORGANISM: Unknown
<220> FEATURE:
<223> OTHER INFORMATION: probe 88

<400> SEQUENCE: 88
gaaggactcg gtgataccca ctgggatctt ttatcctttg ttgcaaaagt gtggacactt    60

<210> SEQ ID NO 89
<211> LENGTH: 60
<212> TYPE: DNA
<213> ORGANISM: Unknown
<220> FEATURE:
<223> OTHER INFORMATION: probe 89

<400> SEQUENCE: 89
cagggcaact caaagaatgt tctgctggca tgtcctatga acatgtaccc gcatggacgc    60

<210> SEQ ID NO 90
<211> LENGTH: 60
<212> TYPE: DNA
<213> ORGANISM: Unknown
<220> FEATURE:
<223> OTHER INFORMATION: probe 90

<400> SEQUENCE: 90
gagaaaagca aagctctttc ttattttcct cataatcagc taccctggag gggagggaga   60

<210> SEQ ID NO 91
<211> LENGTH: 60
<212> TYPE: DNA
<213> ORGANISM: Unknown
<220> FEATURE:
<223> OTHER INFORMATION: probe 91

<400> SEQUENCE: 91
cgaattggga ggcttatatt tttcagcaaa gaaattttgg ggggttttgt gttgttgggc   60

<210> SEQ ID NO 92
<211> LENGTH: 60
<212> TYPE: DNA
<213> ORGANISM: Unknown
<220> FEATURE:
<223> OTHER INFORMATION: probe 92

<400> SEQUENCE: 92
tgaaatgctg gaagggttct ctcccacaa cccctgcctc acggaggcca ttgcagctaa   60

<210> SEQ ID NO 93
<211> LENGTH: 60
<212> TYPE: DNA
<213> ORGANISM: Unknown
<220> FEATURE:
<223> OTHER INFORMATION: probe 93

<400> SEQUENCE: 93
agacctcggt gatcactgag ggatttccgc gagctcggcc tcacttctgc cccgacttgt   60

<210> SEQ ID NO 94
<211> LENGTH: 60
<212> TYPE: DNA
<213> ORGANISM: Unknown
<220> FEATURE:
<223> OTHER INFORMATION: probe 94

<400> SEQUENCE: 94
ctacaagatt ggcaaagaga tgcagaatgc ataagatgaa cattgcatga ccggatcatt   60

<210> SEQ ID NO 95
<211> LENGTH: 60
<212> TYPE: DNA
<213> ORGANISM: Unknown
<220> FEATURE:
<223> OTHER INFORMATION: probe 95

<400> SEQUENCE: 95
aataaacaac tttgatgatg taacttgacc ttccagagtt atggaaattt tgtccccatg   60

<210> SEQ ID NO 96
<211> LENGTH: 60
<212> TYPE: DNA
<213> ORGANISM: Unknown
<220> FEATURE:
<223> OTHER INFORMATION: probe 96

<400> SEQUENCE: 96
aggttctcag aatgaccgta agatagctta catttcctct ttttgccttt atctccccaa   60

<210> SEQ ID NO 97
<211> LENGTH: 60

```
<212> TYPE: DNA
<213> ORGANISM: Unknown
<220> FEATURE:
<223> OTHER INFORMATION: probe 97

<400> SEQUENCE: 97
agagacctgc aggggcctcg gcccctcaca tcgtgtatgt ctctccttga tttgtgttgt      60

<210> SEQ ID NO 98
<211> LENGTH: 60
<212> TYPE: DNA
<213> ORGANISM: Unknown
<220> FEATURE:
<223> OTHER INFORMATION: probe 98

<400> SEQUENCE: 98
ccgttttgtt tctgctcagt aatatagtca agcaagtttg ttccaagtga cccattgagc      60

<210> SEQ ID NO 99
<211> LENGTH: 60
<212> TYPE: DNA
<213> ORGANISM: Unknown
<220> FEATURE:
<223> OTHER INFORMATION: probe 99

<400> SEQUENCE: 99
aaattggcgc tggaatttgg gctgggaaaa atcttgtggt tatttccttt aaaaaggaac      60

<210> SEQ ID NO 100
<211> LENGTH: 60
<212> TYPE: DNA
<213> ORGANISM: Unknown
<220> FEATURE:
<223> OTHER INFORMATION: probe 100

<400> SEQUENCE: 100
gccaaagctc aaatgcccac catagaacga ctgtccatga caagatattt ctacctcttt      60

<210> SEQ ID NO 101
<211> LENGTH: 60
<212> TYPE: DNA
<213> ORGANISM: Unknown
<220> FEATURE:
<223> OTHER INFORMATION: probe 101

<400> SEQUENCE: 101
tggctcccca tcatgtatcc tcccgattat tgcgtattct aaaataggaa acaagacttt      60

<210> SEQ ID NO 102
<211> LENGTH: 60
<212> TYPE: DNA
<213> ORGANISM: Unknown
<220> FEATURE:
<223> OTHER INFORMATION: probe 102

<400> SEQUENCE: 102
tcacgttaac atatagacac tgttggaagc agttccttct aaaagggtag ccctggactt      60

<210> SEQ ID NO 103
<211> LENGTH: 60
<212> TYPE: DNA
<213> ORGANISM: Unknown
<220> FEATURE:
<223> OTHER INFORMATION: probe 103

<400> SEQUENCE: 103
ctatgacacc tttaaggagg ttcttggatc agggatgcag tacccacttg cagtcaaaat      60
```

```
<210> SEQ ID NO 104
<211> LENGTH: 60
<212> TYPE: DNA
<213> ORGANISM: Unknown
<220> FEATURE:
<223> OTHER INFORMATION: probe 104

<400> SEQUENCE: 104
tgtgggtgtc cagcatcttc ttcttccttc ctgtcttctg tctcacggtc ctctacagtc    60

<210> SEQ ID NO 105
<211> LENGTH: 60
<212> TYPE: DNA
<213> ORGANISM: Unknown
<220> FEATURE:
<223> OTHER INFORMATION: probe 105

<400> SEQUENCE: 105
gatgacactg ccacctctga cttctgcctc tggccttcca ctctcagtaa gaagagccag    60

<210> SEQ ID NO 106
<211> LENGTH: 60
<212> TYPE: DNA
<213> ORGANISM: Unknown
<220> FEATURE:
<223> OTHER INFORMATION: probe 106

<400> SEQUENCE: 106
gtcgcctggg attttcatcc ctcgcacaag gactacgggt tcacacggtg aactggggga    60

<210> SEQ ID NO 107
<211> LENGTH: 60
<212> TYPE: DNA
<213> ORGANISM: Unknown
<220> FEATURE:
<223> OTHER INFORMATION: probe 107

<400> SEQUENCE: 107
gccataagaa atttgacaag atggtggaca ctcctgcctc cgagcctgcc caagcctcca    60

<210> SEQ ID NO 108
<211> LENGTH: 60
<212> TYPE: DNA
<213> ORGANISM: Unknown
<220> FEATURE:
<223> OTHER INFORMATION: probe 108

<400> SEQUENCE: 108
aaggcctttg aggttgtgac tgtggctggt atatctggct gccattttc tgatgcattt    60

<210> SEQ ID NO 109
<211> LENGTH: 60
<212> TYPE: DNA
<213> ORGANISM: Unknown
<220> FEATURE:
<223> OTHER INFORMATION: probe 109

<400> SEQUENCE: 109
agaattctta acttcacaag tgttttactt cgacgatgtg cctttgattt aatttgggac    60

<210> SEQ ID NO 110
<211> LENGTH: 60
<212> TYPE: DNA
<213> ORGANISM: Unknown
<220> FEATURE:
<223> OTHER INFORMATION: probe 110
```

<400> SEQUENCE: 110
tcattagaca tcggggattt cactctgcag agtaatcctg gaactacatt aaagtggggg    60

<210> SEQ ID NO 111
<211> LENGTH: 60
<212> TYPE: DNA
<213> ORGANISM: Unknown
<220> FEATURE:
<223> OTHER INFORMATION: probe 111

<400> SEQUENCE: 111
tgcgggaagc ctttcagcca ccgttgcaac ctcaacgagc accagaagcg gcacggggc    60

<210> SEQ ID NO 112
<211> LENGTH: 60
<212> TYPE: DNA
<213> ORGANISM: Unknown
<220> FEATURE:
<223> OTHER INFORMATION: probe 112

<400> SEQUENCE: 112
ttgtaggact taatggctaa gaattagaac atagcaaggg ggctcctctg ttggagtaat    60

<210> SEQ ID NO 113
<211> LENGTH: 1400
<212> TYPE: DNA
<213> ORGANISM: Homo sapiens
<220> FEATURE:
<223> OTHER INFORMATION: cDNA of clone ID I-30

<400> SEQUENCE: 113
cttttcctcc cgctgtcccc cacggagggg actgctctcc cccgctgcat cctttctgtg      60
aggtacctta cccacctcag cacctgagag ggtgaaatag aattctaacc tcgacattcg     120
ggaagtgttt ttgagaagtc tcggtcggta agggaagtct tccaagtccg tgcagcacta    180
acgtattggc acctgcctcc tcttcggcca cccccagat gaggcagctg tgactgtgtc     240
aagggaagcc acgactctga ccatagtctt ctctcagctt ccactgccgt ctccacagga    300
aacccagaag ttctgtgaac aagtccatgc tgccatcaag gcatttattg cagtgtacta    360
tttgcttcca aaggatcagg ccctgagaac aatgacctta tttcctacaa cagtgtctgg    420
gttgcgtgcc agcagatgcc tcagatacca agagataaca aagctgcagc tcttttgatg    480
ctgaccaaga atgtggattt tgtgaaggat gcacatgaaa aaatggagca ggctgtggaa    540
gaatgtgacc cttactctgg cctcttgaat gatactgagg agaacaactc tgacaaccac    600
aatcatgagg atgatgtgtt ggggtttccc agcaatcagg acttgtattg gtcagaggac    660
gatcaagagc tcataatccc atgccttgcg ctggtgagag catccaaagc ctgcctgaag    720
aaaattcgga tgttagtggc agagaatggg aagaaggatc aggtggcaca gctggatgac    780
attgtggata tttctgatga aatcagccct agtgtggatg atttggctct gagcatatat    840
ccacctatgt gtcacctgac cgtgcgaatc aattctgcga aacttgtatc tgttttaaag    900
aaggcacttg aaattacaaa agcaagtcat gtgaccccctc agccagaaga tagttggatc    960
ccttttactta ttaatgccat tgatcattgc atgaatagaa tcaaggagct cactcagagt   1020
gaacttgaat tatgactttt caggctcatt tgtactctct tccctctca tcgtcatggt    1080
caggctctga tacctgcttt taaaatggag ctagaatgct tgctggattg aaagggagtg   1140
cctatctata tttagcaaga gacactatta ccaaagattt ttggttaggc cagattgaca   1200
cctatttata aaccatatgc gtatattttt ctgtgctata tatgaaaaat aattgcatga   1260

-continued

| tttctcattc ctgagtcatt tctcagagat tcctaggaaa gctgccttat tctcttttg | 1320 |
| cagtaaagta tgttgttttc attgtaaaga tgttgatggt ctcaataaaa tgctaacttg | 1380 |
| ccagtgaaaa aaaaaaaaaa | 1400 |

<210> SEQ ID NO 114
<211> LENGTH: 1062
<212> TYPE: DNA
<213> ORGANISM: Homo sapiens
<220> FEATURE:
<223> OTHER INFORMATION: cDNA of clone ID III-02

<400> SEQUENCE: 114

| aggatctaag accagcctgg cagccaccag atggtgattc tagtcctggc tcagtcagta | 60 |
| ataggtcact gaccccagag aaatcaattc agcctcccca ggtccttgga tttctttctg | 120 |
| tgaaaatgaa agcataggta ggaatttccc atggaacagc tagcagagga gaaatattaa | 180 |
| aagtcaggag actcatgcta tagttttcat acttcattac aacaatgttg tttaggacaa | 240 |
| gtgagttaac ctgttagctt cctctatata aaatggaaag tcattaaaaa cctacatagc | 300 |
| agggttcttg tgaagatcaa gtgataatgt aggaagcatg tacaaatgtc acattctgcc | 360 |
| gtcacgtaat ggtcctcaca gcttgaggta gcatttagca tgtgtcatga tttagtacaa | 420 |
| gggttggcaa actgttgctc ttggattaag tctggctcat tgcctgtttt tcaaagaaaa | 480 |
| aaattgtata tgtgtgtata tatgttatat ataggtacac acacatatgt gctatatata | 540 |
| gcatatatac acacataata tataaacatg tacatatata gcattatata tatacgtgta | 600 |
| taatatctcc agtcctcatg accagccatg cttgttcatt tacatttgca tactctatga | 660 |
| ttgctttcat gcaacaatgg cagagttgag tgattgtttt gcaacagaga ctgtatggcc | 720 |
| cactaaacct aaaatattta gtctctgacc ctgaaatgta agattgatag cccaggacca | 780 |
| ggcgtggtgg ctcacacttg taatcctagc actttggcag gccaaggagg gtggatcacc | 840 |
| tgaggtcagg agttaaagac cagcctggcc aacatggtga aaccctgact ctactaaaaa | 900 |
| tacagaaatt agctgggcgt ggtaatgggt gcctgcaatc caagctactc tggaggctga | 960 |
| ggcaggagaa tcacttgaac ccaggaggca gaagttacag tgagctgaga tggtgccact | 1020 |
| gcactccagc ctggacgaca gagtgagact ccatctcaaa aa | 1062 |

<210> SEQ ID NO 115
<211> LENGTH: 266
<212> TYPE: DNA
<213> ORGANISM: Homo sapiens
<220> FEATURE:
<223> OTHER INFORMATION: cDNA of clone ID III-27

<400> SEQUENCE: 115

| ccattctcct gcctcagcct ctcaagtagc tgggactaca ggcgcccaca accacgcccg | 60 |
| gctaatgttt tggtattttt tcgtagagac ggggtttcac cttgttagcc aggatggtct | 120 |
| tgatctcctg acctcgtgat ctgcctgcct cggcctccca agtgttggg attacaggca | 180 |
| cattttcac aatttttaa cacttaagaa tgacttaact gaatcatgcc tttagaagaa | 240 |
| actttctgtt taaaaaaaaa aaaaaa | 266 |

<210> SEQ ID NO 116
<211> LENGTH: 1271
<212> TYPE: DNA
<213> ORGANISM: Homo sapiens
<220> FEATURE:
<223> OTHER INFORMATION: cDNA of clone ID III-60

<400> SEQUENCE: 116

| | |
|---|---|
| ctgccgccgc cccagctcc ccgcctcgg ggagggcacc aggtcactgc agccagaggg | 60 |
| gtccagaaga gagaggaggc actgcctcca ctacagcaac tgcacccacg atgcagagca | 120 |
| tcaagtgcgt ggtggtgggt gatggggctg tgggcaagac gtgcctgctc atctgctaca | 180 |
| caactaacgc tttccccaaa gagtacatcc ccaccgtgtt cgacaattac agcgcgcaga | 240 |
| gcgcagttga cgggcgcaca gtgaacctga acctgtggga cactgcgggc caggaggagt | 300 |
| atgaccgcct ccgtacactc tcctaccctc agaccaacgt tttcgtcatc tgtttctcca | 360 |
| ttgccagtcc gccgtcctat gagaacgtgc ggcacaagtg gcatccagag gtgtgccacc | 420 |
| actgccctga tgtgcccatc ctgctggtgg gcaccaagaa ggacctgaga gcccagcctg | 480 |
| acaccctacg gcgcctcaag gagcagggcc aggcgcccat cacaccgcag cagggccagg | 540 |
| cactggccaa gcagatccac gctgtgcgct acctcgaatg ctcagccctg caacaggatg | 600 |
| gtgtcaagga agtgttcgcc gaggctgtcc gggctgtgct caaccccacg ccgatcaagc | 660 |
| gtgggcggtc ctgcatcctc ttgtgaccct ggcacttggc ttggaggctg cccctgccct | 720 |
| ccccccacca gttgtgcctt ggtgccttgt ccgcctcagc tgtgccttaa ggactaattc | 780 |
| tggcacccct ttccagggg ttccctgaat gccttttctt ctgagtgcct ttttctcctt | 840 |
| aaggaggcct gcagagaaag gggctttggg ctctgccccc ctctgcttgg aacactggg | 900 |
| tattctcatg agctcatcca agccaaggtt ggaccctcc ccaagaggcc aacccagtgc | 960 |
| cccctcccat tttccgtact gaccagttca tccagctttc cacacagttg ttgctgccta | 1020 |
| ttgtggtgcc gcctcaggtt aggggctctc agccatctct aacctctgcc ctcgctgctc | 1080 |
| ttggaattgc gccccaaga tgctctctcc cttctccaat gagggagcca cagaatcctg | 1140 |
| agaaggtgaa tgtgccctaa cctgctcctc tgtgcctagg ccttacgcat ttgctgactg | 1200 |
| actcagcccc catgcttctg gggacctttc ctaccccat cagcatcaat aaaacctcct | 1260 |
| gtctccagtg a | 1271 |

<210> SEQ ID NO 117
<211> LENGTH: 831
<212> TYPE: DNA
<213> ORGANISM: Homo sapiens
<220> FEATURE:
<223> OTHER INFORMATION: cDNA of clone ID IV-26

<400> SEQUENCE: 117

| | |
|---|---|
| cagccctccg tcacctcttc accgcaccct cggactgccc caaggccccc gccgccgctc | 60 |
| cagcgccgcg cagccaccgc cgccgccgcc gcctctcctt agtcgccgcc atgacgaccg | 120 |
| cgtccacctc gcaggtgcgc cagaactacc accaggacta gaggccgcc atcaaccgcc | 180 |
| agatcaacct ggagctctac gcctcctacg tttacctgtc catgtcttac tactttgacc | 240 |
| gcgatgatgt ggctttgaag aactttgcca atactttct tcaccaatct catgaggaga | 300 |
| gggaacatgc tgagaaactg atgaagctgc agaaccaacg aggtggccga atcttccttc | 360 |
| aggatatcaa gaaaccagac tgtgatgact gggagagcgg gctgaatgca atggagtgtg | 420 |
| cattacattt ggaaaaaaat gtgaatcagt cactactgga actgcacaaa ctggccactg | 480 |
| acaaaaatga ccccatttg tgtgacttca ttgagacaca ttacctgaat gagcaggtga | 540 |
| aagccatcaa agaattgggt gaccacgtga ccaacttgcg caagatggga gcgcccgaat | 600 |
| ctggcttggc ggaatatctc tttgacaagc acacctggg agacagtgat aatgaaagct | 660 |
| aagcctcggg ctaatttccc catagccgtg gggtgacttc cctggtcacc aaggcagtgc | 720 |

```
atgcatgttg gggtttcctt tacctttct ataagttgta ccaaaacatc cacttaagtt    780
ctttgatttg taccattcct tcaaataaag aaatttggta cccaaaaaaa a            831

<210> SEQ ID NO 118
<211> LENGTH: 197
<212> TYPE: DNA
<213> ORGANISM: Homo sapiens
<220> FEATURE:
<223> OTHER INFORMATION: cDNA of clone ID IV-41

<400> SEQUENCE: 118
gccatttcta agacctacag ctacctgacc cccgacctct ggaaggagac tgtattcacc    60
aagtctccct atcaggagtt cactgaccac ctcgtcaaga cccacaccag agtctccgtg   120
cagcggactc aggctccagc tgtggctaca acatagggtt tttatacaag aaaaataaag   180
tgaattaagc gtgaaaa                                                   197

<210> SEQ ID NO 119
<211> LENGTH: 426
<212> TYPE: DNA
<213> ORGANISM: Homo sapiens
<220> FEATURE:
<223> OTHER INFORMATION: cDNA of clone ID IV-51

<400> SEQUENCE: 119
atttctgtgg atacagtgcc caccgccctc ctccacttgg aaacggtatc ctccctgccc    60
atccgtctgt ctgtcgccct tctcccggcc ctcactaagc cccggcactt ctagtggtct   120
cacctggagg caagagggag gggacagagg ccctgccacg tcccgctgcc tcctgctctc   180
tggaggtact gagacagggt gctgatggga aggaggggag cctttggggg gccacccggg   240
gcctggacct atgcagggag gccacgtccc accccacctc ttgtttctgg gtccctgctc   300 cccttttgggg gtgtgtgtgt gtgttttaat tttctttatg gaaaattga caaaaaaaa    360 tagagagaga ggtatttaac tgcaataaac tggccccatg tggccccgc cttgtcaaaa    420 aaaaaa                                                              426

<210> SEQ ID NO 120
<211> LENGTH: 990
<212> TYPE: DNA
<213> ORGANISM: Homo sapiens
<220> FEATURE:
<223> OTHER INFORMATION: cDNA of clone ID V-09

<400> SEQUENCE: 120
tggattcccg tcgtaactta aagggaaact ttcacaatgt ccggagccct tgatgtcctg    60
caaatgaagg aggaggatgt ccttaagttc cttgcagcag gaacccactt aggtggcacc   120
aatcttgact tccagatgga acagtacatc tataaaagga aaagtgatgg catctatatc   180
ataaatctca gaggacctg ggagaagctt ctgctggcag ctcgtgcaat tgttgccatt   240
gaaaaccctg ctgatgtcag tgttatatcc tccaggaata ctggccagag ggctgtgctg   300
aagtttgctg ctgccactgg agccactcca attgctggcc gcttcactcc tggaaccttc   360
actaaccaga tccaggcagc cttccgggag ccacggcttc ttgtggttac tgaccccagg   420
gctgaccacc agcctctcac ggaggcatct tatgttaacc tacctaccat gcgctgtgt    480 aacacagatt ctcctctgcg ctatgtggac attgccatcc catgcaacaa caagggagct   540
cactcagtgg gtttaatgtg gtggatgctg gctcgggaag ttctgcgcat gcgtggcacc   600
atttcccgtg aacacccatg ggaggtcatg cctgatctgt acttctacag agatcctgaa   660
```

```
gagattgaaa aagaagagca ggctgctgct gagaaggcag tgaccaagga ggaatttcag      720
ggtgaatgga ctgctcccgc tcctgagttc actgctactc agcctgaggt tgcagactgg      780
tctgaaggtg tacaggtgcc ctctgtgcct attcagcaat tccctactga agactggagc      840
gctcagcctg ccacggaaga ctggtctgca gctcccactg ctcaggccac tgaatgggta      900
ggagcaacca ctgactggtc ttaagctgtt cttgcatagg ctcttaagca gcatggaaaa      960
atggttgatg gaaataaac atcagtttct                                        990
```

<210> SEQ ID NO 121
<211> LENGTH: 1279
<212> TYPE: DNA
<213> ORGANISM: Homo sapiens
<220> FEATURE:
<223> OTHER INFORMATION: cDNA of clone ID V-38

<400> SEQUENCE: 121

```
gtttaaattt gacaaactaa agctaattac tgctataaga gtaataactg ctcatttcc       60 ataactcatt cttaaagttt tagtaatgta aaagttattt ttttgcagta agttataatg     120
atagaagctt acatgttttt tcatgcctca tctgtttccc cttaaaacta aattatcag     180 taaagtcctg tggtattttt caatttgtaa gaaactaggc tatatataca ttgggaaaaa     240
cagccttcat ttgtcaatgc actagtgttc caaaggtttc tggtaattgt gtgctattgc     300
tttttgttga cttgcaaaaa aaaaaaaaaa aaaattacta tgacttgtgg tagccctgca     360
accttcggaa gtgcttagcc cagtctgacc atacatttat atttagaatg cttaggtaaa     420
taaataatat gcctaaaccc aatgctataa gatactatat aatatctcat aattttaaaa     480
atcactgttt tgtataataa taaaacaagg caggcaagct gttctacaat gactgttggt     540
aagggtgctg aggaagaaaa acaaacaatc ttgattcagg gatagtgaat agacaaaaaa     600
tgtcctaatc aatgaagctg tgtgatgatt ctgattgaca gagagtgctg ccacaagatt     660
cttaggctac actcaaatca gcagaaaaag tgctacaata aattagaagt gactattaca     720
ggtgcagatg agggttggta gtacctgttt gccatttctc ttctaatctt atattttctg     780
accctcctac tgtaagtcgc gcggaggcgg aggcttgggt gcgttcaaga ttcaacttca     840
cccgtaaccc accgccatgg ccgaggaagg cattgctgct ggaggtgtaa tggacgttaa     900
tactgcttta caagaggttc tgaagactgc cctcatccac gatggcctag cacgtggaat     960
tcgcgaagct gccaaagcct tagacaagcg ccaagcccat ctttgtgtgc ttgcatccaa    1020
ctgtgatgag cctatgtatg tcaagttggt ggaggccctt tgtgctgaac accaaatcaa    1080
cctaattaag gttgatgaca acaagaaact aggagaatgg gtaggccttt gtaaaattga    1140
cagagagggg aaacccgta aagtggttgg ttgcagttgt gtagtagtta aggactatgg      1200
caaggagtct caggccaagg atgtcattga agagtatttc aaatgcaaga atgaagaaa     1260 taaatctttg gctcacaaa                                                 1279
```

<210> SEQ ID NO 122
<211> LENGTH: 753
<212> TYPE: DNA
<213> ORGANISM: Homo sapiens
<220> FEATURE:
<223> OTHER INFORMATION: cDNA of clone ID VI-44

<400> SEQUENCE: 122

```
gagaatggct tgaacccagt aggcagaggt tgtagtgagc cgagattggg ccactgcact       60
ttagcctggg tgacagagtg agactctgtc tcaaaaaaaa aaaaaaaaaa tttaaataaa     120
```

```
ataaaaaacc tttacttatt tttaaattgg gttgtctttt tggtattgag ttgttaaagt    180
tctttatata ttttaggtac aaatcccttta tgagatacgt gatttgaaaa tattttctcc   240
cattctgtgg gttgcttttt cactttcttg gttgtatcct ttgaagcaca gaagttttaa   300
attttgatga agtccagttt atttatttttt ttgctgttgt ttctgctcat acttttgagg   360
tcatgtctga gaaaccattg tcaaatccaa ggtcgtgatg acttacccct gtgttttctt   420
ctaagagttt taaaggcatc tgaagcttaa tgtgcactag atggattcta aatatcatct   480
catccaaaac ctgctatata tactaccttc ctcatctcag ttgaaggcaa gtccattgtt   540
tcaattgcct gggcaaaaaa tattctaaat aattcataat ttttcctcaa ctccacatct   600
attggtaaat cctgtgggtt ctccttttaa aacatatcca aaatagaatc atttctcact   660
atcattccac tgcaggcacc aagtctcaat agtctcctag cagataatca tgtctacatt   720
tattctcaat gtagcagcta gagagcttttt ttg                               753
```

```
<210> SEQ ID NO 123
<211> LENGTH: 517
<212> TYPE: DNA
<213> ORGANISM: Homo sapiens
<220> FEATURE:
<223> OTHER INFORMATION: cDNA of clone ID VI-49

<400> SEQUENCE: 123
gcggtcgtaa gggctgagga tttttggtcc gcacgctcct gctcctgact caccgctgtt    60
cgctctcgcc gaggaacaag tcggtcagga agcccgcgcg caacagccat ggcttttaag   120
gataccggaa aaacacccgt ggagccggag gtggcaattc accgaattcg aatcacccta   180
acaagccgca acgtaaaatc cttggaaaag gtgtgtgctg acttgataag aggcgcaaaa   240
gaaaagaatc tcaaagtgaa aggaccagtt cgaatgccta ccaagacttt gagaatcact   300
acaagaaaaa ctccttgtgg tgaaggttct aagacgtggg atcgtttcca gatgagaatt   360
cacaagcgac tcattgactt gcacagtcct tctgagattg ttaagcagat tacttccatc   420
agtattgagc caggagttga ggtggaagtc accattgcag atgcttaagt caactatttt   480
aataaattga tgaccagttg ttaaaaaaaa aaaaaaa                             517
```

```
<210> SEQ ID NO 124
<211> LENGTH: 159
<212> TYPE: DNA
<213> ORGANISM: Homo sapiens
<220> FEATURE:
<221> NAME/KEY: misc_feature
<222> LOCATION: (9)..(149)
<223> OTHER INFORMATION: cDNA of clone ID VI-52

<400> SEQUENCE: 124
gaaaagggnt ngcncccaan gggcagaggt tgggctgatg ccgatattgg gccnctgcnc    60
tncanacctg ggtgacatga atgaaactct gtctcacata aaaacccaaa aaanctaaat   120
gaaataaaag acctttgctt attnctaant tgggtacgc                           159
```

```
<210> SEQ ID NO 125
<211> LENGTH: 315
<212> TYPE: DNA
<213> ORGANISM: Homo sapiens
<220> FEATURE:
<223> OTHER INFORMATION: cDNA of clone ID VII-15

<400> SEQUENCE: 125
cccatcccct cgaccgctcg cgtcgcattt ggccgcctcc ctaccgctcc aagcccagcc    60
```

```
ctcagccatg gcatgccccc tggatcaggc cattggcctc ctcgtggcca tcttccacaa    120
gtactccggc agggagggtg acaagcacac cctgagcaag aaggagctga aggagctgat    180
ccagaaggag ctcaccattg gctcgaagct gcaggatgct gaaattgcaa ggctgatgga    240
agacttggac cggaacaagg accaggaggt gaacttccag gagtatgtca ccttcctggg    300
ggccttggct ttgat                                                    315
```

```
<210> SEQ ID NO 126
<211> LENGTH: 491
<212> TYPE: DNA
<213> ORGANISM: Homo sapiens
<220> FEATURE:
<223> OTHER INFORMATION: cDNA of clone ID VII-32

<400> SEQUENCE: 126
aattagagag gtgaggatct ggtatttcct ggactaaatt ccccttgggg aagacgaagg     60
gatgctgcag ttccaaaaga gaaggactct tccagagtca tctacctgag tcccaaagct    120
ccctgtcctg aaagccacag acaatatggt cccaaatgac tgactgcacc ttctgtgcct    180
cagccgttyt tgacatcaag aatcttctgt tccacatcca cacagccaat acaattagtc    240
aaaccactgt tattaacaga tgtagcaaca tgagaaacgc ttatgttaca ggttacatga    300
gagcaatcat gtaagtctat atgacttcag aaatgttaaa atagactaac ctctaacaac    360
aaattaaaag tgattgtttc aaggtgatgc aattattgat gacctatttt attttctat     420 aatgatcata tattacccttt gtaataaaac attataacca aaaaaaaaaa aaaaaaaaa    480 aaaaaaaaaa a                                                         491
```

```
<210> SEQ ID NO 127
<211> LENGTH: 707
<212> TYPE: DNA
<213> ORGANISM: Homo sapiens
<220> FEATURE:
<223> OTHER INFORMATION: cDNA of clone ID VII-48

<400> SEQUENCE: 127
cttaagtatg ccctgacagg agatgaagta aagaagattt gcatgcagcg gttcattaaa     60
atcgatggca aggtccgaac tgatataacc taccctgctg gattcatgga tgtcatcagc    120
attgacaaga cgggagagaa tttccgtctg atctatgaca ccaagggtcg ctttgctgta    180
catcgtatta cacctgagga ggccaagtac aagttgtgca aagtgagaaa gatctttgtg    240
ggcacaaaag gaatccctca tctggtgact catgatgccc gcaccatccg ctaccccgat    300
cccctcatca aggtgaatga taccattcag attgatttag agactggcaa gattactgat    360
ttcatcaagt tcgacactgg taacctgtgt atggtgactg gaggtgctaa cctaggaaga    420
attggtgtga tcaccaacag agagaggcac cctggatctt ttgacgtggt tcacgtgaaa    480
gatgccaatg gcaacagctt tgccactcga cttttccaaca tttttgttat tggcaagggc    540
aacaaaccat ggatttctct tccccgagga aagggtatcc gcctcaccat tgctgaagag    600
agagacaaaa gactggcggc caaacagagc agtgggtgaa atgggtccct gggtgacatg    660
tcagatcttt gtacgtaatt aaaaatattg tggcaggatt aatagcc                 707
```

```
<210> SEQ ID NO 128
<211> LENGTH: 636
<212> TYPE: DNA
<213> ORGANISM: Homo sapiens
<220> FEATURE:
<223> OTHER INFORMATION: cDNA of clone ID VII-76
```

<400> SEQUENCE: 128

| | |
|---|---|
| agacacacga gcatatttca cctccgctac cataatcatc gctatcccca ccggcgtcaa | 60 |
| agtatttagc tgactcgcca cactccacgg aagcaatatg aaatgatctg ctgcagtgct | 120 |
| ctgagcccta ggattcatct ttcttttcac cgtaggtggc ctgactggca ttgtattagc | 180 |
| aaactcatca ctagacatcg tactacacga cacgtactac gttgtagccc acttccacta | 240 |
| tgtcctatca ataggagctg tatttgccat cataggaggc ttcattcact gatttcccct | 300 |
| attctcaggc tacaccctag accaaaccta cgccaaaatc catttcacta tcatattcat | 360 |
| cggcgtaaat ctaactttct tcccacaaca ctttctcggc ctatccggaa tgccccgacg | 420 |
| ttactcggac taccccgatg catacaccac atgaaacatc ctatcatctg taggctcatt | 480 |
| catttctcta acagcagtaa tattaataat tttcatgatt tgagaagcct tcgcttcgaa | 540 |
| gcgaaaagtc ctaatagtag aagaaccctc cataaacctg gagtgactat atggatgccc | 600 |
| cccaccctac cacacattcg aagaacccgt atacat | 636 |

<210> SEQ ID NO 129
<211> LENGTH: 549
<212> TYPE: DNA
<213> ORGANISM: Homo sapiens
<220> FEATURE:
<223> OTHER INFORMATION: cDNA of clone ID IX-24

<400> SEQUENCE: 129

| | |
|---|---|
| agagtgcaag acgatgactt gcaaaatgtc gcagctggaa cgcaacatag agaccatcat | 60 |
| caacaccttc caccaatact ctgtgaagct ggggcaccca gacaccctga ccaggggga | 120 |
| attcaaagag ctggtgcgaa agatctgca aaattttctc aagaaggaga ataagaatga | 180 |
| aaaggtcata gaacacatca tggaggacct ggacacaaat gcagacaagc agctgagctt | 240 |
| cgaggagttc atcatgctga tggcgaggct aacctgggcc tcccacgaga agatgcacga | 300 |
| gggtgacgag ggccctggcc accaccataa gccaggcctc ggggagggca cccctaaga | 360 |
| ccacagtggc caagatcaca gtggccacgg ccacggccac agtcatggtg gccacggcca | 420 |
| cagccactaa tcaggaggcc aggccaccct gcctctaccc aaccagggcc ccggggcctg | 480 |
| ttatgtcaaa ctgtcttggc tgtggggcta ggggctgggg ccaaataaag tctcttcctc | 540 |
| caaaaaaaa | 549 |

<210> SEQ ID NO 130
<211> LENGTH: 425
<212> TYPE: DNA
<213> ORGANISM: Homo sapiens
<220> FEATURE:
<223> OTHER INFORMATION: cDNA of clone ID IX-39

<400> SEQUENCE: 130

| | |
|---|---|
| cttggctcct gtggaggcct gctgggaacg ggacttctaa aaggaactat gtctggaagg | 60 |
| ctgtggtcca aggccatttt tgctggctat aagcggggtc tccggaacca aagggagcac | 120 |
| acagctcttc ttaaaattga aggtgtttac gcccgagatg aaacagaatt ctatttgggc | 180 |
| aagagatgcg cttatgtata taaagcaaag aacaacacag tcactcctgg cggcaaacca | 240 |
| aacaaaacca gagtcatctg ggaaaaagta actcgggccc atggaaacag tggcatggtt | 300 |
| cgtgccaaat tccgaagcaa tcttcctgct aaggccattg gacacagaat ccgagtgatg | 360 |
| ctgtaccccct caaggattta aactaacgaa aaatcaataa ataaatgtgg atttgtgctc | 420 |
| ttgta | 425 |

<210> SEQ ID NO 131
<211> LENGTH: 809
<212> TYPE: DNA
<213> ORGANISM: Homo sapiens
<220> FEATURE:
<223> OTHER INFORMATION: cDNA of clone ID IX-46

<400> SEQUENCE: 131

```
acgcgagatg gcagtgcaaa tatccaagaa gaggaagttt gtcgctgatg gcatcttcaa      60
agctgaactg aatgagtttc ttactcggga gctggctgaa gatggctact ctggagttga     120
ggtgcgagtt acaccaacca ggacagaaat cattatctta gccaccagaa cacagaatgt     180
tcttggtgag aagggccggc ggattcggga actgactgct gtagttcaga gaggtttgg      240
ctttccagag ggcagtgtag agctttatgc tgaaaaggtg ccactagag gtctgtgtgc      300
cattgcccag gcagagtctc tgcgttacaa actcctagga gggcttgctg tgcggagggc     360
ctgctatggt gtgctgcggt tcatcatgga gagtggggcc aaaggctgcg aggttgtggt     420
gtctgggaaa ctccgaggac agagggctaa atccatgaag tttgtggatg cctgatgat     480
ccacagcgga gaccctgtta actactacgt tgacactgct gtgcgccacg tgttgctcag     540
acagggtgtg ctgggcatca aggtgaagat catgctgccc tgggacccaa ctggtaagat     600
tggccctaag aagcccctgc ctgaccacgt gagcattgtg gaacccaaag atgagatact     660
gcccaccacc cccatctcag aacagaaggg tgggaagcca gagccgcctg ccatgcccca     720
gccagtcccc acagcataac agggtctcct tggcagctgt attctggagt ctggatgttg     780
ctctctaaag acctttaata aaattttgt                                       809
```

<210> SEQ ID NO 132
<211> LENGTH: 663
<212> TYPE: DNA
<213> ORGANISM: Homo sapiens
<220> FEATURE:
<223> OTHER INFORMATION: cDNA of clone ID IX-50

<400> SEQUENCE: 132

```
gtccatcctg caggccacaa gctctggatg aggaacttga ggcaagtcac cagcccctga      60
tcatttcgcc taaagagca aggactagag ttcctgacct ccaggccagt ccctgatccc     120
tgacctaatg ttatcgcgga atgatgatat atgtatctac gggggcctgg ggctgggcgg     180
gctcctgctt ctggcagtgg tccttctgtc cgcctgcctg tgttggctgc atcgaagagt     240
aaagaggctg gagaggagct gggcccaggg ctcctcagag caggaactcc actatgcatc     300
tctgcagagg ctgccagtgc ccagcagtga gggacctgac ctcaggggca gagacaagag     360
aggcaccaag gaggatccaa gagctgacta tgcctgcatt gctgagaaca aacccacctg     420
agcaccccag acaccttcct caacccaggc gggtggacag ggtccccctg tggtccagcc     480
agtaaaaacc atggtccccc cacttctgtg tctcagtcct ctcagtccat ctcgagcctc     540
cgttcaaaat gatcatcatc aaaacttatg tggcttttg acctttgaat agggaatttt     600
ttaaatttt taaaaattaa aataaaaaaa acacatggct cacccttcca cccaaaaaaa     660
aaa                                                                  663
```

<210> SEQ ID NO 133
<211> LENGTH: 693
<212> TYPE: DNA
<213> ORGANISM: Homo sapiens
<220> FEATURE:
<223> OTHER INFORMATION: cDNA of clone ID X-77

<400> SEQUENCE: 133

```
cctcccgggc tcttaagccc ctctctttct ctaacagaaa aagcggatgg tggttcctgc    60
tgccctcaag gtcgtgcgtc tgaagcctac aagaaagttt gcctatctgg ggcgcctggc   120
tcacgaggtt ggctggaagt accaggcagt gacagccacc ctggaggaga agaggaaaga   180
gaaagccaag atccactacc ggaagaagaa acagctcatg aggctacgga acaggccga   240
gaagaacgtg gagaagaaaa ttgacaaata cacagaggtc ctcaagaccc acggactcct   300
ggtctgagcc caataaagac tgttaattcc tcatgcgttg cctgcccttc ctccattgtt   360
gccctggaat gtacgggacc caggggcagc agcagtccag gtgccacagg cagccctggg   420
acataggaag ctgggagcaa ggaaagggtc ttagtcactg cctcccgaag ttgcttgaaa   480
gcactcggag aattgtgcag gtgtcattta tctatgacca ataggaagag caaccagtta   540
ctatgagtga aagggagcca aagactgat tggagggccc tatcttgtga gtggggcatc    600
tgttggactt tccacctggt catatactct gcagctgtta aatgtgcaa gcacttgggg    660
acagcatgag cttgctgttg tacacagggt att                                693
```

<210> SEQ ID NO 134
<211> LENGTH: 722
<212> TYPE: DNA
<213> ORGANISM: Homo sapiens
<220> FEATURE:
<223> OTHER INFORMATION: cDNA of clone ID XI-13

<400> SEQUENCE: 134

```
ctgccaacat ggtgttcagg cgcttcgtgg aggttggccg ggtggcctat gtctcctttg    60
gacctcatgc cggaaaattg gtcgcgattg tagatgttat tgatcagaac agggctttgg   120
tcgatggacc ttgcactcaa gtgaggagac aggccatgcc tttcaagtgc atgcagctca   180
ctgatttcat cctcaagttt ccgcacagtg cccaccagaa gtatgtccga caagcctggc   240
agaaggcaga catcaataca aaatgggcag ccacacgatg ggccaagaag attgaagcca   300
gagaaaggaa agccaagatg acagattttg atcgttttaa agttatgaag gcaaagaaaa   360
tgaggaacag aataatcaag aatgaagtta agaagcttca aaaggcagct ctcctgaaag   420
cttctcccaa aaaagcacct ggtactaagg gtactgctgc tgctgctgct gctgctgctg   480
ctgctgctgc tgctgctgct gctaaagttc cagcaaaaaa gatcaccgcc gcgagtaaaa   540
aggctccagc ccagaaggtt cctgcccaga aagccacagg ccagaaagca gcgcctgctc   600
caaaagctca gaagggtcaa aaagctccag cccagaaagc acctgctcca aaggcatctg   660
gcaagaaagc ataagtggca atcataaaaa gtaataaagg ttcttttga cctgttaaaa   720
aa                                                                  722
```

<210> SEQ ID NO 135
<211> LENGTH: 642
<212> TYPE: DNA
<213> ORGANISM: Homo sapiens
<220> FEATURE:
<223> OTHER INFORMATION: cDNA of clone ID XI-49

<400> SEQUENCE: 135

```
gatcaacctg gagctctacg cctcctacgt ttacctgtcc atgtcttact actttgaccg    60
cgatgatgtg gctttgaaga actttgccaa atactttctt caccaatctc atgaggagag   120
ggaacatgct gagaaactga tgaagctgca gaaccaacga ggtggccgaa tcttccttca   180
ggatatcaag aaaccagact gtgatgactg ggagagcggg ctgaatgcaa tggagtgtgc   240
```

| | |
|---|---|
| attacatttg gaaaaaaatg tgaatcagtc actactggaa ctgcacaaac tggccactga | 300 |
| caaaaatgac ccccatttgt gtgacttcat tgagacacat tacctgaatg agcaggtgaa | 360 |
| agccatcaaa gaattgggtg accacgtgac caacttgcgc aagatgggag cgcccgaatc | 420 |
| tggcttggcg gaatatctct tgacaagca caccctggga gacagtgata atgaaagcta | 480 |
| agcctcgggc taatttcccc atagccgtgg ggtgacttcc ctggtcacca aggcagtgca | 540 |
| tgcatgttgg ggtttccttt acctttcta taagttgtac caaaacatcc acttaagttc | 600 |
| tttgatttgt accattcctt caaataaaga aatttggtac cc | 642 |

<210> SEQ ID NO 136
<211> LENGTH: 360
<212> TYPE: DNA
<213> ORGANISM: Homo sapiens
<220> FEATURE:
<223> OTHER INFORMATION: cDNA of clone ID XI-81

<400> SEQUENCE: 136

| | |
|---|---|
| agagcagcag ccatggccct acgctaccct atggccgtgg gcctcaacaa gggccacaaa | 60 |
| gtgaccaaga acgtgagcaa gcccaggcac agccgacgcc gcgggcgtct gaccaaacac | 120 |
| accaagttcg tgcgggacat gattcgggag gtgtgtggct ttgccccgta cgagcggcgc | 180 |
| gccatggagt tactgaaggt ctccaaggac aaacgggccc tcaaatttat caagaaaagg | 240 |
| gtggggacgc acatccgcgc caagaggaag cgggaggagc tgagcaacgt actggccgcc | 300 |
| atgaggaaag ctgctgccaa gaaagactga gcccctcccc tgccctctcc ctgaaataaa | 360 |

<210> SEQ ID NO 137
<211> LENGTH: 622
<212> TYPE: DNA
<213> ORGANISM: Homo sapiens
<220> FEATURE:
<223> OTHER INFORMATION: cDNA of clone ID XII-35

<400> SEQUENCE: 137

| | |
|---|---|
| ctctcctgtc aacagcggcc agcctcccaa ctacgagatg ctcaaggagg agcaggaagt | 60 |
| ggctatgctg ggggcgcccc acaaccctgc tcccccgacg tccaccgtga tccacatccg | 120 |
| cagcgagacc tccgtgcccg accatgtcgt ctggtccctg ttcaacaccc tcttcatgaa | 180 |
| cacctgctgc ctgggcttca tagcattcgc ctactccgtg aagtctaggg acaggaagat | 240 |
| ggttggcgac gtgaccgggg cccaggccta tgcctccacc gccaagtgcc tgaacatctg | 300 |
| ggccctgatt ttgggcatct tcatgaccat tctgctcgtc atcatcccag tgttggtcgt | 360 |
| ccaggcccag cgatagatca ggaggcatca ttgaggccag gagctctgcc cgtgaccctgt | 420 |
| atcccacgta ctctatcttc cattcctcgc cctgccccca gaggccagga gctctgccct | 480 |
| tgacctgtat tccacttact ccaccttcca ttcctcgccc tgtccccaca gccgagtcct | 540 |
| gcatcagccc tttatcctca cacgcttttc tacaatggca ttcaataaag tgtatatgtt | 600 |
| tctggtgctg ctgtgacttc aa | 622 |

<210> SEQ ID NO 138
<211> LENGTH: 372
<212> TYPE: DNA
<213> ORGANISM: Homo sapiens
<220> FEATURE:
<223> OTHER INFORMATION: cDNA of clone ID XII-77

<400> SEQUENCE: 138

| | |
|---|---|
| gtaagaaagc ccttaaataa agaaggtaag aaacctagga ccaaagcacc caagattcag | 60 |

| | |
|---|---|
| cgtcttgtta ctccacgtgt cctgcagcac aaacggcggc gtattgctct gaagaagcag | 120 |
| cgtaccaaga aaataaaga agaggctgca gaatatgcta aacttttggc caagagaatg | 180 |
| aaggaggcta aggagaagcg ccaggaacaa attgcgaaga gacgcagact ttcctctctg | 240 |
| cgagcttcta cttctaagtc tgaatccagt cagaaataag attttttgag taacaaataa | 300 |
| ataagatcag actctgaaaa aaaaaaaaaa aaaaaaaaa aaaaaaaaaa aaaaaaaaaa | 360 |
| aaaaaaaaaa aa | 372 |

<210> SEQ ID NO 139
<211> LENGTH: 836
<212> TYPE: DNA
<213> ORGANISM: Homo sapiens
<220> FEATURE:
<223> OTHER INFORMATION: cDNA of clone ID XIII-29

<400> SEQUENCE: 139

| | |
|---|---|
| ctcgctcacg cagcactcgt ggcagtccct gaaggaccgc tacctcaagc acctgcgggg | 60 |
| ccaggagcat aagtacctgc tgggggacgc gccggtgagc ccctcctccc agaagctcaa | 120 |
| gcggaaggcg gaggaggacc cggaggccgc ggatagcggg gaaccacaga ataagagaac | 180 |
| tccagatttg cctgaagaag agtatgtgaa ggaagaaatc caggagaatg aagaagcagt | 240 |
| caaaaagatg cttgtggaag ccacccggga gtttgaggag gttgtggtgg atgagagccc | 300 |
| tcctgatttt gaaatacata taactatgtg tgatgatgat ccacccacac ctgaggaaga | 360 |
| ctcagaaaca cagcctgatg aggaggaaga agaagaagaa gaaaaagttt ctcaaccaga | 420 |
| ggtgggagct gccattaaga tcattcggca gttaatggag aagtttaact tggatctatc | 480 |
| aacagttaca caggccttcc taaaaaatag tggtgagctg gaggctactt ccgccttctt | 540 |
| agcgtctggt cagagagctg atggatatcc catttggtcc cgacaagatg acatagattt | 600 |
| gcaaaaagat gatgaggata ccagagaggc attggtcaaa aaatttggtg ctcagaatgt | 660 |
| agctcggagg attgaatttc gaaagaaata attggcaaga taatgagaaa agaaaaaagt | 720 |
| catggtaggt gaggtggtta aaaaaaattg tgaccaatga actttagaga gttcttgcat | 780 |
| tggaactggc acttattttc tgaccatcgc tgctgttgct ctgtgagtcc tagatt | 836 |

<210> SEQ ID NO 140
<211> LENGTH: 840
<212> TYPE: DNA
<213> ORGANISM: Homo sapiens
<220> FEATURE:
<223> OTHER INFORMATION: cDNA of clone ID XIII-84

<400> SEQUENCE: 140

| | |
|---|---|
| attatcctca gttcccaaga gcaatcatac ttttccacac ataccgtgtg tctcatgtta | 60 |
| ggtaaatgta tttttacaat gagcaccact tctgtggaaa aagttccctg cacggggagg | 120 |
| tccagcttcc agactgctcc atcgcataag gacttcccca ttcccctaaa tgctgctctg | 180 |
| tcagaacctg cccaggtaat ggtaatgacc ctagagagat gatttctgaa ccgcaatttt | 240 |
| gagcccatta gaaggtgtgt ggtgggcatt tatttcatcc tgatgctctg gtgagaatct | 300 |
| ttgcagacgc actagatcca gaagctgtta atcttggtgc atttattttc ctacctaaaa | 360 |
| gaaccaagca gctcagaggc agtgactgta caggatgcag tgtttataat aatgctgagc | 420 |
| ttgctggtct ggaaccccac acttcagcaa tcccagcatt gttcctgttt atgaagttga | 480 |
| caaagtgacc agggcaaggg ggtattatca ttaaatacac tctaggagag cagaacaca | 540 |
| tgagggcaat gttttttcaga ggtctttagg ccaccgcatc agattctcct ggagcataaa | 600 |

```
gcaaatgctt tatgagtcca gggcccctgc agacctactg tatactagta tacagctccc      660
tcttagtgga tctcaagctt gtttccaaaa agtcattaca ctccttacca aagcccatga      720
cacattcata cagattcatc cagacataac ccactgcatg gtccagtgca tgcttgtgtg      780
cttaacttat tatagatcaa gtgttatttta agtccaacat attaaacgtg actgaatatt     840

<210> SEQ ID NO 141
<211> LENGTH: 325
<212> TYPE: DNA
<213> ORGANISM: Homo sapiens
<220> FEATURE:
<223> OTHER INFORMATION: cDNA of clone ID XV-49

<400> SEQUENCE: 141
aagtctgccc agaaagctca gaaggctaaa tgaatattat ccctaatacc tgccacccca      60
ctcttaatca gtggtggaag aacggtctca gaactgtttg tttcaattgg ccatttaagt     120
ttagtagtaa aagactggtt aatgataaca atgcatcgta aaaccttcag aaggaaagga     180
gaatgttttg tggaccactt tggttttctt ttttgcgtgt ggcagtttta agttattagt     240
ttttaaaatc agtactttt aatggaaaca acttgaccaa aaatttgtca cagaattttg     300
agacccatta aaaaagttaa atgag                                           325

<210> SEQ ID NO 142
<211> LENGTH: 1142
<212> TYPE: DNA
<213> ORGANISM: Homo sapiens
<220> FEATURE:
<223> OTHER INFORMATION: cDNA of clone ID XV-54

<400> SEQUENCE: 142
aagagcaggt ctctggaggc tgagttgcat ggggcctagt aacaccaagc cagtgagcct      60
ctaatgctac tgcgccctgg gggctcccag ggcctgggca acttagctgc aactggcaaa     120
ggagaagggt agtttgaggt gtgacaccag tttgctccag aaagtttaag gggtctgttt     180
ctcatctcca tggacatctt caacagcttc acctgacaac gactgttcct atgaagaagc     240
cacttgtgtt ttaagcagag gcaacctctc tcttctcctc tgtttcgtga aggcagggga     300
cacagatggg agagattgag ccaagtcagc cttctgttgg ttaatatggt ataatgcatg     360
gctttgtgca cagcccagtg tgggattaca gctttgggat gaccgcttac aaagttctgt     420
ttggttagta ttggcatagt ttttctatat agccataaat gcgtatatat acccataggg     480
ctagatctgt atcttagtgt agcgatgtat acatatacac atccacctac atgttgaagg     540
gcctaaccag ccttgggagt attgactggt cccttacctc ttatggctaa gtctttgact     600
gtgttcattt accaagttga cccagtttgt cttttaggtt aagtaagact cgagagtaaa     660
ggcaaggagg ggggccagcc tctgaatgcg gccacggatg ccttgctgct gcaacccttt     720
ccccagctgt ccactgaaac gtgaagtcct gttttgaatg ccaaacccac cattcactgg     780
tgctgactac atagaatggg gttgagagaa gatcagtttg ggcttacag tgtcatttga      840 aaacgttttt tgttttgttt tgtaattatt gtggaaaact ttcaagtgaa cagaaggatg     900
gtgtcctact gtggatgagg gatgaacaag gggatggctt tgatccaatg gagcctggga     960
ggtgtgccca gaaagcttgt ctgtagcggg ttttgtgaga gtgaacactt tccacttttt    1020
gacaccttat cctgatgtat ggttccagga tttggatttt gatttccaa atgtagcttg    1080 aaatttcaat aaactttgct ctgttttttct aaaaataaaa aaaaaaaaa aaaaaaaaa     1140 aa                                                                  1142
```

<210> SEQ ID NO 143
<211> LENGTH: 1006
<212> TYPE: DNA
<213> ORGANISM: Homo sapiens
<220> FEATURE:
<223> OTHER INFORMATION: cDNA of clone ID XV-75

<400> SEQUENCE: 143

| | | | | | |
|---|---|---|---|---|---|
| agcagatgac | ccttcgtggc | accctcaagg | gccacaacgg | ctgggtaacc | cagatcgcta | 60 |
| ctaccccgca | gttcccggac | atgatcctct | ccgcctctcg | agataagacc | atcatcatgt | 120 |
| ggaaactgac | cagggatgag | accaactatg | gaattccaca | gcgtgctctg | cggggtcact | 180 |
| cccactttgt | tagtgatgtg | gttatctcct | cagatggcca | gtttgccctc | tcaggctcct | 240 |
| gggatggaac | cctgcgcctc | tgggatctca | aacgggcac | caccacgagg | cgatttgtgg | 300 |
| gccataccaa | ggatgtgctg | agtgtggcct | tctcctctga | caaccggcag | attgtctctg | 360 |
| gatctcgaga | taaaaccatc | aagctatgga | atacccctggg | tgtgtgcaaa | tacactgtcc | 420 |
| aggatgagag | ccactcagag | tgggtgtctt | gtgtccgctt | ctcgcccaac | agcagcaacc | 480 |
| ctatcatcgt | ctcctgtggc | tgggacaagc | tggtcaaggt | atggaacctg | gctaactgca | 540 |
| agctgaagac | caaccacatt | ggccacacag | gctatctgaa | cacggtgact | gtctctccag | 600 |
| atggatccct | ctgtgcttct | ggaggcaagg | atggccaggc | catgttatgg | gatctcaacg | 660 |
| aaggcaaaca | cctttacacg | ctagatggtg | gggacatcat | caacgccctg | tgcttcagcc | 720 |
| ctaaccgcta | ctggctgtgt | gctgccacag | gccccagcat | caagatctgg | gatttagagg | 780 |
| gaaagatcat | tgtagatgaa | ctgaagcaag | aagttatcag | taccagcagc | aaggcagaac | 840 |
| caccccagtg | cacctccctg | gcctggtctg | ctgatggcca | gactctgttt | gctggctaca | 900 |
| cggacaacct | ggtgcgagtg | tggcaggtga | ccattggcac | acgctagaag | tttatggcag | 960 |
| agctttacaa | ataaaaaaaa | aactggcttt | tctgacaaaa | aaaaaa | | 1006 |

<210> SEQ ID NO 144
<211> LENGTH: 562
<212> TYPE: DNA
<213> ORGANISM: Homo sapiens
<220> FEATURE:
<223> OTHER INFORMATION: cDNA of clone ID XV-86

<400> SEQUENCE: 144

| | | | | | |
|---|---|---|---|---|---|
| gcaaaatgtc | gcagctggaa | cgcaacatag | agaccatcat | caacaccttc | caccaatact | 60 |
| ctgtgaagct | ggggcaccca | gacaccctga | accaggggga | attcaaagag | ctggtgcgaa | 120 |
| aagatctgca | aaattttctc | aagaaggaga | ataagaatga | aaaggtcata | gaacacatca | 180 |
| tggaggacct | ggacacaaat | gcagacaagc | agctgagctt | cgaggagttc | atcatgctga | 240 |
| tggcgaggct | aacctgggcc | tcccacgaga | agatgcacga | gggtgacgag | ggccctggcc | 300 |
| accaccataa | gccaggcctc | ggggagggca | ccccctaaga | ccacagtggc | caagatcaca | 360 |
| gtggccacgg | ccacgccac | agtcatggtg | gccacggcca | cagccactaa | tcaggaggcc | 420 |
| aggccaccct | gcctctaccc | aaccagggcc | ccggggcctg | ttatgtcaaa | ctgtcttggc | 480 |
| tgtggggcta | ggggctgggg | ccaaataaag | tctcttcctc | caaaaaaaaa | aaaaaaaaa | 540 |
| aaaaaaaaaa | aaaaaaaaaa | aa | | | | 562 |

<210> SEQ ID NO 145
<211> LENGTH: 1052
<212> TYPE: DNA
<213> ORGANISM: Homo sapiens

```
<220> FEATURE:
<223> OTHER INFORMATION: cDNA of clone ID XVI-74

<400> SEQUENCE: 145
cgccgccgcg  ccgccgtcgc  tctccaacgc  cagcgccgcc  tctcgctcgc  cgagctccag       60
ccgaaggaga  agggggggtaa gtaaggaggt  ctctgtacca  tggctcgtac  aaagcagact      120
gcccgcaaat  cgaccggtgg  taaagcaccc  aggaagcaac  tggctacaaa  agccgctcgc      180
aagagtgcgc  cctctactgg  aggggtgaag  aaacctcatc  gttacaggcc  tggtactgtg      240
gcgctccgtg  aaattagacg  ttatcagaag  tccactgaac  ttctgattcg  caaacttccc      300
ttccagcgtc  tggtgcgaga  aattgctcag  gactttaaaa  cagatctgcg  cttccagagc      360
gcagctatcg  gtgctttgca  ggaggcaagt  gaggcctatc  tggttggcct  ttttgaagac      420
accaacctgt  gtgctatcca  tgccaaacgt  gtaacaatta  tgccaaaaga  catccagcta      480
gcacgccgca  tacgtggaga  acgtgcttaa  gaatccacta  tgatgggaaa  catttcattc      540
tcaaaaaaaa  aaaaaaaaaa  tttctcttct  tcctgttatt  ggtagttctg  aacgttagat      600 atttttttc  catggggtca  aaaggtacct  aagtatatga  ttgcgagtgg  aaaaatagggg     660 gacagaaatc  aggtattggc  agttttcca  ttttcatttg  tgtgtgaatt  tttaatataa      720
atgcggagac  gtaaagcatt  aatgcaagtt  aaaatgtttc  agtgaacaag  tttcagcggt      780
tcaactttat  aataattata  aataaacctg  ttaaattttt  ctggacaatg  ccagcatttg      840 gatttttta  aaacaagtaa  atttcttatt  gatggcaact  aaatggtgtt  tgtagcattt      900
ttatcataca  gtagattcca  tccattcact  atacttttct  aactgagttg  tcctacatgc      960
aagtacatgt  ttttaatgtt  gtctgtcttc  tgtgctgttc  ctgtaagttt  gctattaaaa     1020
tacattaaac  tataaaaaaa  aaaaaaaaaa  aa                                    1052

<210> SEQ ID NO 146
<211> LENGTH: 450
<212> TYPE: DNA
<213> ORGANISM: Homo sapiens
<220> FEATURE:
<223> OTHER INFORMATION: cDNA of clone ID XVII-77

<400> SEQUENCE: 146
cagacaccct  gaaccagggg  gaattcaaag  agctggtgcg  aaaagatctg  caaaattttc       60
tcaagaagga  gaataagaat  gaaaaggtca  tagaacacat  catggaggac  ctggacacaa      120
atgcagacaa  gcagctgagc  ttcgaggagt  tcatcatgct  gatggcgagg  ctaacctggg      180
cctcccacga  gaagatgcac  gagggtgacg  agggccctgg  ccaccaccat  aagccaggcc      240
tcggggaggg  cacccctaa  gaccacagtg  gccaagatca  cagtggccac  ggccacggcc      300
acagtcatgg  tggccacggc  cacagccact  aatcaggagg  ccaggccacc  ctgcctctac      360
ccaaccaggg  ccccggggcc  tgttatgtca  aactgtcttg  gctgtggggc  tagggctgg      420 ggccaaataa  agtctcttcc  tccaaaaaaa                                         450
```

OLIGONUCLEOTIDES FOR CANCER DIAGNOSIS

This application is a 371 of PCT/GB2005/002180, filed Jun. 2, 2004; the disclosure of which is incorporated herein by reference.

The present invention relates to oligonucleotide probes, for use in assessing gene transcript levels in a cell, which may be used in analytical techniques, particularly diagnostic techniques. Conveniently the probes are provided in kit form. Different sets of probes may be used in techniques to prepare gene expression patterns and identify, diagnose or monitor different cancers or stages thereof.

The identification of quick and easy methods of sample analysis for, for example, diagnostic applications, remains the goal of many researchers. End users seek methods which are cost effective, produce statistically significant results and which may be implemented routinely without the need for highly skilled individuals.

The analysis of gene expression within cells has been used to provide information on the state of those cells and importantly the state of the individual from which the cells are derived. The relative expression of various genes in a cell has been identified as reflecting a particular state within a body. For example, cancer cells are known to exhibit altered expression of various proteins and the transcripts or the expressed proteins may therefore be used as markers of that disease state.

Thus biopsy tissue may be analysed for the presence of these markers and cells originating from the site of the disease may be identified in other tissues or fluids of the body by the presence of the markers. Furthermore, products of the altered expression may be released into the blood stream and these products may be analysed. In addition cells which have contacted disease cells may be affected by their direct contact with those cells resulting in altered gene expression and their expression or products of expression may be similarly analysed.

However, there are some limitations with these methods. For example, the use of specific tumour markers for identifying cancer suffers from a variety of defects, such as lack of specificity or sensitivity, association of the marker with disease states besides the specific type of cancer, and difficulty of detection in asymptomatic individuals.

In addition to the analysis of one or two marker transcripts or proteins, more recently, gene expression patterns have been analysed. Most of the work involving large-scale gene expression analysis with implications in disease diagnosis has involved clinical samples originating from diseased tissues or cells. For example, several recent publications, which demonstrate that gene expression data can be used to distinguish between similar cancer types, have used clinical samples from diseased tissues or cells (Alon et al. 1999, PNAS, 96, p 6745-6750; Golub et al. 1999, Science, 286, p 531-537; Alizadeh et al, 2000, Nature, 403, p 503-511; Bittner et al., 2000, Nature, 406, p 536-540).

However, these methods have relied on analysis of a sample containing diseased cells or products of those cells or cells which have been contacted by disease cells. Analysis of such samples relies on knowledge of the presence of a disease and its location, which may be difficult in asymptomatic patients. Furthermore, samples can not always be taken from the disease site, e.g. in diseases of the brain.

In a finding of great significance, the present inventors identified the previously untapped potential of all cells within a body to provide information relating to the state of the organism from which the cells were derived. WO98/49342 describes the analysis of the gene expression of cells distant from the site of disease, e.g. peripheral blood collected distant from a cancer site. PCT/GB03/005102, incorporated herein by reference, describes specific probes for the diagnosis of breast cancer and Alzheimer's disease and discusses protocols for identifying other appropriate probes for that purpose and for diagnosing other diseases.

This finding is based on the premise that the different parts of an organism's body exist in dynamic interaction with each other. When a disease affects one part of the body, other parts of the body are also affected. The interaction results from a wide spectrum of biochemical signals that are released from the diseased area, affecting other areas in the body. Although, the nature of the biochemical and physiological changes induced by the released signals can vary in the different body parts, the changes can be measured at the level of gene expression and used for diagnostic purposes.

The physiological state of a cell in an organism is determined by the pattern with which genes are expressed in it. The pattern depends upon the internal and external biological stimuli to which said cell is exposed, and any change either in the extent or in the nature of these stimuli can lead to a change in the pattern with which the different genes are expressed in the cell. There is a growing understanding that by analysing the systemic changes in gene expression patterns in cells in biological samples, it is possible to provide information on the type and nature of the biological stimuli that are acting on them. Thus, for example, by monitoring the expression of a large number of genes in cells in a test sample, it is possible to determine whether their genes are expressed with a pattern characteristic for a particular disease, condition or stage thereof. Measuring changes in gene activities in cells, e.g. from tissue or body fluids is therefore emerging as a powerful tool for disease diagnosis.

Such methods have various advantages. Often, obtaining clinical samples from certain areas in the body that is diseased can be difficult and may involve undesirable invasions in the body, for example biopsy is often used to obtain samples for cancer. In some cases, such as in Alzheimer's disease the diseased brain specimen can only be obtained post-mortem. Furthermore, the tissue specimens which are obtained are often heterogeneous and may contain a mixture of both diseased and non-diseased cells, making the analysis of generated gene expression data both complex and difficult.

It has been suggested that a pool of tumour tissues that appear to be pathogenetically homogeneous with respect to morphological appearances of the tumour may well be highly heterogeneous at the molecular level (Alizadeh, 2000, supra), and in fact might contain tumours representing essentially different diseases (Alizadeh, 2000, supra; Golub, 1999, supra). For the purpose of identifying a disease, condition, or a stage thereof, any method that does not require clinical samples to originate directly from diseased tissues or cells is highly desirable since clinical samples representing a homogeneous mixture of cell types can be obtained from an easily accessible region in the body.

We have now identified a family of sequences which allow the derivation of a set of probes of surprising utility for identifying cancer, particularly breast cancer. Thus, we now describe families of genes whose expression is altered in the cells of blood samples from cancer patients, which may be used to generate probes for use in methods of identifying, diagnosing or monitoring cancer or stages thereof.

In work leading up to this invention, the inventors examined the level of expression of a large number of genes in cancer patients relative to normal patients. Not only were a large number of genes found to exhibit altered expression, but, in addition, those which exhibited altered expression were found to fall within discrete families of genes, by virtue of their function. As such these genes provide a pool from which corresponding probes may be generated which can be used collectively to generate a fingerprint of the expression of these genes in an individual. Since the expression of these genes is altered in the cancer individual, and may hence be considered informative for that state, the generated fingerprint from the collection of probes is indicative of the disease relative to the normal state.

The families of genes that have been identified as being differentially expressed in cancer patients may be summarized as follows:

(i) genes encoding proteins involved in protein synthesis and/or stability;

(ii) genes encoding proteins involved in the regulation of defence and/or chromatin remodelling.

Family (i) includes:

(a) genes encoding ribosomal proteins and ribosomal activation proteins (ie. proteins comprising components of ribosomal proteins or involved in modification of their function and are found to be down-regulated in cancer patients). These encoded proteins include ribosomal proteins L1-L56, L7A, L10A, L13A, L18A, L23A, L27A, L35A, L36A, L37A, P0, P1, P2, S2-S29, S31, S33-S36, S3A, S15A, S18A, S18B, S18C, S27A, 63, 115 (and pseudogenes), ribosomal protein kinases (e.g. S6 kinase), ribonucleases, putative S1 RNA binding domain protein, eukaryotic translation initiation factors and guanine nucleotide binding protein G;

(b) genes encoding translation inhibition and initiation factors (ie. proteins involved in the translation of mRNA to a protein product and are found to be down-regulated in cancer patients). These encoded proteins include eukaryotic translation elongation factors, tRNA synthetases, RNA binding proteins, polyadenylation element binding proteins, tyrosine phosphatases, eukaryotic translation initiation factors, and RNA polymerase I, III transcription factors;

(c) genes encoding other modulators of transcription or translation such as cyclin D-type binding protein and guanine nucleotide binding protein.

Family (ii) includes:

(a) genes encoding immune response related proteins (ie. proteins which are up-regulated in response to immune stimulation, and which include proteins upregulated in response to inflammation or in generating an inflammatory response, and are found to be up-regulated in cancer patients). These encoded proteins include T-cell receptor and associated components, e.g. protein kinases, various cytokines, including the interleukins and their receptors (such as IL-1, 2, 3, 4, 5, 6, 7, 8, 9, 10, 11, 12, 13, 15, 17, 18, 20, 22, 24), tumour necrosis factor and its receptor and its superfamily (e.g. TNF superfamily members 2, 3, 4, 5, 6, 7, 8, 9, 11, 12, 13, 14, 15), interferon regulatory factors, oncostatin M, Leukemia inhibitory factor, chemokine ligand and receptor family (e.g. numbers 1-28), complement components, interferon stimulated factors such as transcription factors, MHC (e.g HLA) class I or II (or related components) (e.g. DQ, DR, DO, DP, DM alpha or beta), adhesion proteins (e.g. CD1A, CD1C, CD1D, CD3Z, 6, 8, 11, 14, 18, 24, 27, 28, 29, 40, 44, 50, 54, 59, 74, 79B, 80, 81, 83, 86, 96, ICAM), nuclear factor of kappa polypeptide gene enhancer in B-cells, myelin basic protein, cathepsin, toll-like receptor, proteosome subunits, ferritin, protein kinases or phosphatases as well as their activators and inhibitors, leukocyte immunoglobulin-like receptor, immunoglobulin components, e.g. heavy chain or Fc fragments, e.g. of IgG, IgE or IgA or their superfamily, defensin, oxytocin, S100 calcium binding protein, lectin and its receptor and superfamily, leptin, phospholipase and growth factors (such as endothelial cell growth factor or erythropoietin);

(b) genes encoding TNF-induced proteins (ie. proteins which are induced in an individual in response to exposure to TNF and are found to be up-regulated in cancer patients). These encoded proteins include TNF alpha-induced protein 8, integrin, inhibitor of kappa light polypeptide gene enhancer in B-cells, TNF-associated factor 2, 5, nuclear factor of kappa light polypeptide gene enhancer in B-cells, MAP kinases, protein kinase C, ubiquitous kinase, cadherin, caspase, cyclin D1, superoxide dismutase and interleukins;

(c) genes encoding hypoxia-induced proteins (ie. proteins which are induced when the individual or a part thereof is in a state of hypoxia and are found to be up-regulated in cancer patients). These encoded proteins include sestrin, E1A binding protein p300, endothelin, ataxia telangiectasia and Rad3 related protein, hexokinase 2, TEK tyrosine kinase, DNA fragmentation factor, caspase, plasminogen activator, hypoxia-inducible factor 1 and glucose phosphate isomerase;

(d) genes encoding oxidative stress proteins (ie. proteins which are induced in an individual or part thereof under oxidative stress and are found to be up-regulated in cancer patients). These encoded proteins include superoxide dismutase, glutathione synthetase, catalase, lactoperoxidase, thyroid peroxidase, myeloperoxidase, eosinophil peroxidase, oxidation resistance 1, peroxiredoxin, cytochrome P450, scavenger receptor, paraoxonase, glutathione reductase, NAD(P)H dehydrogenase, glutathione S-transferase, catenin, glutaredoxin, heat shock proteins (such as heat shock transcription factors), mitogen-activated protein kinases, enolase, thioredoxin reductase and peroxiredoxin;

(e) genes encoding proteins involved in chromatin remodelling (ie. proteins which are instrumental in maintaining or modifying chromatin structure and may be essential for gene regulation). These encoded proteins include histone replacement proteins, e.g. H3.3A or H3.3B family.

Appropriate gene sequences falling within the families described above may be identified by interrogation of appropriate databases using as keywords the family name, e.g. "immune response" on gene or protein databases at National Centre for Biotechnology Information, Norway. For confirmation of the utility of such gene sequences for the development of oligonucleotides for the tests described herein, the expression of a particular gene sequence may be assessed in a test cancer patient versus a normal patient. Variation in expression above or below control levels is indicative of the utility of the sequence for probe derivation.

Generally the genes encoding the above (i) families are down-regulated in cancer versus normal patients and in the case of (ii) families the encoding genes are up-regulated.

It is speculated that in cancer patients the systematic decreased expression of genes involved in ribosome production and translation control may indicate that blood cells are responding to a new condition in those patients by decreasing the rate of protein synthesis which may be a cellular adaption to an environment of low oxygen and energy deficiency. This is supported by the observation that genes involved in defence against reactive oxygen species (ROS) such as MnSOD and ferritin are upregulated in cancer samples. Low erythropoietin may explain the low oxygen levels in cancer patients. TNF activation is also believed to be a route for the changes in the families of genes described above since TNF is known to up regulate expression of e.g. ferritin, defensin, MnSOD and calgranulin B. TNF also inhibits EPO production which can itself cause a low oxygen condition in the blood environment. Hypoxia is known to induce TNF levels. These changes may be triggered by angiogenic factors entering the bloodstream. Although not wishing to be bound by theory, the hypothesis underlying the above described effects is shown in FIG. 1.

Thus the invention provides a set of oligonucleotide probes which correspond to genes in a cell whose expression is affected in a pattern characteristic of a particular cancer or stage of, wherein said genes are systemically affected by said cancer or stage thereof. Preferably said genes are constitutively moderately or highly expressed. Preferably the genes are moderately or highly expressed in the cells of the sample but not in cells from disease cells or in cells having contacted such disease cells.

Such probes, particularly when isolated from cells distant to the site of disease, do not rely on the development of disease to clinically recognizable levels and allow detection of a cancer or stage thereof very early after the onset of said cancer, even years before other subjective or objective symptoms appear.

As used herein "systemically" affected genes refers to genes whose expression is affected in the body without direct contact with a disease cell or disease site and the cells under investigation are not disease cells.

"Contact" as referred to herein refers to cells coming into close proximity with one another such that the direct effect of one cell on the other may be observed, e.g. an immune response, wherein these responses are not mediated by secondary molecules released from the first cell over a large distance to affect the second cell. Preferably contact refers to physical contact, or contact that is as close as is sterically possible, conveniently, cells which contact one another are found in the same unit volume, for example within 1 cm$^3$.

A "disease cell" is a cell manifesting phenotypic changes and is present at the disease site at some time during its life-span, e.g. a tumour cell at the tumour site or which has disseminated from the tumour, or a brain cell in the case of cancer of the brain.

"Moderately or highly" expressed genes refers to those present in resting cells in a copy number of more than 30-100 copies/cell (assuming an average $3\times10^5$ mRNA molecules in a cell).

Specific probes having the above described properties are provided herein.

Thus in one aspect, the present invention provides a set of oligonucleotide probes, wherein said set comprises at least 10 oligonucleotides selected from:

an oligonucleotide corresponding to a gene sequence from family (i) or (ii) as defined hereinbefore or derived from such a sequence, or an oligonucleotide with a complementary sequence, or a functionally equivalent oligonucleotide.

The invention further provides a method of preparing a set of oligonucleotides for use in the methods described herein, comprising the step of selecting one or more oligonucleotides corresponding to a gene sequence from family (i) and one or more oligonucleotides corresponding to a gene sequence from family (ii). Preferably more than 1 oligonucleotides is selected from each family (e.g. from different sub-families) and the selected oligonucleotides are from preferred genes as described herein.

The invention also provides one or more oligonucleotide probes, wherein each oligonucleotide probe is selected from the oligonucleotides listed in Table 2, 3 or 4 (e.g. from Table 2) or derived from a sequence described in Table 2, 3 or 4, or a complementary sequence thereof. Said derived oligonucleotides include oligonucleotides derived from the genes corresponding to the sequences provided in those tables, e.g. the genes set forth in Tables 2, 5 or 6 (see the Accession numbers), or the complementary sequences thereof. The use of such probes in products and methods of the invention, form further aspects of the invention.

As referred to herein an "oligonucleotide" is a nucleic acid molecule having at least 6 monomers in the polymeric structure, ie. nucleotides or modified forms thereof. The nucleic acid molecule may be DNA, RNA or PNA (peptide nucleic acid) or hybrids thereof or modified versions thereof, e.g. chemically modified forms, e.g. LNA (Locked Nucleic acid), by methylation or made up of modified or non-natural bases during synthesis, providing they retain their ability to bind to complementary sequences. Such oligonucleotides are used in accordance with the invention to probe target sequences and are thus referred to herein also as oligonucleotide probes or simply as probes.

An oligonucleotide corresponding to a gene sequence from family (i) or (ii) refers to an oligonucleotide corresponding to all or a part of said gene sequence or its transcript. When a part of the gene sequence is used, it satisfies the requirements of the oligonucleotide probes as described herein, e.g. in length and function. Preferably said parts have the size described hereinafter. Said oligonucleotide is referred to hereinafter as the primary oligonucleotide. A derived oligonucleotide refers to an oligonucleotide which is a part of the primary oligonucleotide but satisfies the requirements for probes as described herein.

Preferably the oligonucleotide probes forming said set are at least 15 bases in length to allow binding of target molecules. Especially preferably said oligonucleotide probes are from 20 to 200 bases in length, e.g. from 30 to 150 bases, preferably 50-100 bases in length.

As referred to herein the term "complementary sequences" refers to sequences with consecutive complementary bases (ie. T:A, G:C) and which complementary sequences are therefore able to bind to one another through their complementarity.

Reference to "10 oligonucleotides" refers to 10 different oligonucleotides. Whilst an oligonucleotide from a gene sequence family as described herein, a derived oligonucleotide and their functional equivalent are considered different oligonucleotides, complementary oligonucleotides are not considered different. Preferably however, the at least 10 oligonucleotides correspond to 10 different gene sequences within the described gene sequence families (or derived oligonucleotides or their functional equivalents). Thus said 10 different oligonucleotides are preferably able to bind to 10 different transcripts.

Preferably the at least 10 oligonucleotides are made up of a combination of oligonucleotides from family (i) and (ii), e.g. 5 oligonucleotides from each family may be used, or 4 from one family and 6 from the other family. This advantageously allows the use of genes which are up and down-regulated in cancer relative to normal patients. Conveniently, one or more oligonucleotides from different sub-families may be used, e.g. 2 probes each from (i)a, (i)b, (i)c, (ii)a and (ii)b. Especially preferably said set of oligonucleotides includes oligonucleotides from family (i)a, (ii)a and (ii)e.

Preferred proteins encoded by family (i)a genes are ribosomal proteins and preferably each set includes an oligonucleotide from a gene encoding such a protein.

Preferred immune response proteins encoded by family (ii)a genes include adhesion proteins, interleukins their receptors and superfamily, TNF its receptor and superfamily, immunoglobulin components and erythropoietin.

Particularly preferably said set includes oligonucleotides from genes encoding one or more ribosomal proteins and optionally one or more histones and optionally ferritin.

Preferably said oligonucleotides are as described in Table 2 or 3 or are derived from a sequence described in Table 2 or 3, e.g. as described in Table 2. Said set may additionally comprise one or more oligonucleotide probes listed in Table 4, or derived from a sequence described in Table 4, or a complementary sequence thereof. Said derived oligonucleotides include oligonucleotides derived from the genes corresponding to the sequences provided in those tables, e.g. the genes set forth in Tables 2, 5 or 6 (see the Accession numbers), or the complementary sequences thereof.

A "set" as described refers to a collection of unique oligonucleotide probes (ie. having a distinct sequence) and preferably consists of less than 1000 oligonucleotide probes, especially less than 500 probes, e.g. preferably from 10 to 500, e.g. 10 to 100, 200 or 300, especially preferably 20 to 100, e.g. 30 to 100 probes. In some cases less than 10 probes may be used, e.g. from 2 to 9 probes, e.g. 5 to 9 probes.

It will be appreciated that increasing the number of probes will prevent the possibility of poor analysis, e.g. misdiagnosis by comparison to other diseases which could similarly alter the expression of the particular genes in question. Other oligonucleotide probes not described herein may also be present, particularly if they aid the ultimate use of the set of oligonucleotide probes. However, preferably said set consists only of the oligonucleotides described herein, or a sub-set thereof (e.g. of the size as described above).

Multiple copies of each unique oligonucleotide probe, e.g. 10 or more copies, may be present in each set, but constitute only a single probe.

A set of oligonucleotide probes, which may preferably be immobilized on a solid support or have means for such immobilization, comprises the at least 10 oligonucleotide probes selected from those described hereinbefore. As mentioned above, these 10 probes must be unique and have different sequences. Having said this however, two separate probes may be used which recognize the same gene but reflect different splicing events. However oligonucleotide probes which are complementary to, and bind to distinct genes are preferred.

As described herein a "functionally equivalent" or derived oligonucleotide refers to an oligonucleotide which is capable of identifying the same gene as an oligonucleotide from a sequence in the gene sequence families described herein ie. it can bind to the same mRNA molecule (or DNA) transcribed from a gene (target nucleic acid molecule) as the primary oligonucleotide or the derived oligonucleotide (or its complementary sequence). Thus in a preferred feature said derived or functionally equivalent oligonucleotide is a part of a gene sequence as defined in Table 2, 5 or 6, or the complementary sequence thereof. Preferably said functionally equivalent oligonucleotide is capable of recognizing, ie. binding to the same splicing product as a primary oligonucleotide or a derived oligonucleotide. Preferably said mRNA molecule is the full length mRNA molecule which corresponds to the primary oligonucleotide or the derived oligonucleotide.

As referred to herein "capable of binding" or "binding" refers to the ability to hybridize under conditions described hereinafter.

Alternatively expressed, functionally equivalent oligonucleotides (or complementary sequences) have sequence identity or will hybridize, as described hereinafter, to a region of the target molecule to which molecule a primary oligonucleotide or a derived oligonucleotide or a complementary oligonucleotide binds. Preferably, functionally equivalent oligonucleotides (or their complementary sequences) hybridize to one of the mRNA sequences which corresponds to a primary oligonucleotide or a derived oligonucleotide under the conditions described hereinafter or has sequence identity to a part of one of the mRNA sequences which corresponds to a primary oligonucleotide or a derived oligonucleotide. A "part" in this context refers to a stretch of at least 5, e.g. at least 10 or 20 bases, such as from 5 to 100, e.g. 10 to 50 or 15 to 30 bases.

In a particularly preferred aspect, the functionally equivalent oligonucleotide binds to all or a part of the region of a target nucleic acid molecule (mRNA or cDNA) to which the primary oligonucleotide or derived oligonucleotide binds. A "target" nucleic acid molecule is the gene transcript or related product e.g. mRNA, or cDNA, or amplified product thereof. Said "region" of said target molecule to which said primary oligonucleotide or derived oligonucleotide binds is the stretch over which complementarity exists. At its largest this region is the whole length of the primary oligonucleotide or derived oligonucleotide, but may be shorter if the entire primary sequence or derived oligonucleotide is not complementary to a region of the target sequence.

Preferably said part of said region of said target molecule is a stretch of at least 5, e.g. at least 10 or 20 bases, such as from 5 to 100, e.g. 10 to 50 or 15 to 30 bases. This may for example be achieved by said functionally equivalent oligonucleotide having several identical bases to the bases of the primary oligonucleotide or the derived oligonucleotide. These bases may be identical over consecutive stretches, e.g. in a part of the functionally equivalent oligonucleotide, or may be present non-consecutively, but provide sufficient complementarity to allow binding to the target sequence.

Thus in a preferred feature, said functionally equivalent oligonucleotide hybridizes under conditions of high stringency to a primary oligonucleotide or a derived oligonucleotide or the complementary sequence thereof. Alternatively expressed, said functionally equivalent oligonucleotide exhibits high sequence identity to all or part of a primary oligonucleotide. Preferably said functionally equivalent oligonucleotide has at least 70% sequence identity, preferably at least 80%, e.g. at least 90, 95, 98 or 99%, to all of a primary oligonucleotide or a part thereof. As used in this context, a "part" refers to a stretch of at least 5, e.g. at least 10 or 20 bases, such as from 5 to 100, e.g. 10 to 50 or 15 to 30 bases, in said primary oligonucleotide. Especially preferably when sequence identity to only a part of said primary oligonucleotide is present, the sequence identity is high, e.g. at least 80% as described above.

Functionally equivalent oligonucleotides which satisfy the above stated functional requirements include those which are derived from the primary oligonucleotides and also those which have been modified by single or multiple nucleotide base (or equivalent) substitution, addition and/or deletion, but which nonetheless retain functional activity, e.g. bind to the same target molecule as the primary oligonucleotide or the derived oligonucleotide from which they are further derived or modified. Preferably said modification is of from 1 to 50, e.g. from 10 to 30, preferably from 1 to 5 bases. Especially preferably only minor modifications are present, e.g. variations in less than 10 bases, e.g. less than 5 base changes.

Within the meaning of "addition" equivalents are included oligonucleotides containing additional sequences which are complementary to the consecutive stretch of bases on the target molecule to which the primary oligonucleotide or the derived oligonucleotide binds. Alternatively the addition may comprise a different, unrelated sequence, which may for example confer a further property, e.g. to provide a means for immobilization such as a linker to bind the oligonucleotide probe to a solid support.

Particularly preferred are naturally occurring equivalents such as biological variants, e.g. allelic, geographical or allotypic variants, e.g. oligonucleotides which correspond to a genetic variant, for example as present in a different species.

Functional equivalents include oligonucleotides with modified bases, e.g. using non-naturally occurring bases. Such derivatives may be prepared during synthesis or by post production modification.

"Hybridizing" sequences which bind under conditions of low stringency are those which bind under non-stringent conditions (for example, 6×SSC/50% formamide at room temperature) and remain bound when washed under conditions of low stringency (2×SSC, room temperature, more preferably 2×SSC, 42° C.). Hybridizing under high stringency refers to the above conditions in which washing is performed at 2×SSC, 65° C. (where SSC=0.15M NaCl, 0.015M sodium citrate, pH 7.2).

"Sequence identity" as referred to herein refers to the value obtained when assessed using ClustalW (Thompson et al., 1994, Nucl. Acids Res., 22, p 4673-4680) with the following parameters:
Pairwise alignment parameters—Method: accurate, Matrix: IUB, Gap open penalty: 15.00, Gap extension penalty: 6.66; Multiple alignment parameters—Matrix: IUB, Gap open penalty: 15.00, % identity for delay: 30, Negative matrix: no, Gap extension penalty: 6.66, DNA transitions weighting: 0.5.

Sequence identity at a particular base is intended to include identical bases which have simply been derivatized.

The invention also extends to polypeptides encoded by the mRNA sequence to which a Table 2, 3 or 4 oligonucleotide or a Table 2, 3 or 4 derived oligonucleotide (e.g. having a sequence as defined in Table 2, 5 or 6 or a complementary sequence thereto) binds. The invention further extends to antibodies which bind to any of said polypeptides.

As described above, conveniently said set of oligonucleotide probes may be immobilized on one or more solid supports. Single or preferably multiple copies of each unique probe are attached to said solid supports, e.g. 10 or more, e.g. at least 100 copies of each unique probe are present.

One or more unique oligonucleotide probes may be associated with separate solid supports which together form a set of probes immobilized on multiple solid support, e.g. one or more unique probes may be immobilized on multiple beads, membranes, filters, biochips etc. which together form a set of probes, which together form modules of the kit described hereinafter. The solid support of the different modules are conveniently physically associated although the signals associated with each probe (generated as described hereinafter) must be separately determinable. Alternatively, the probes may be immobilized on discrete portions of the same solid support, e.g. each unique oligonucleotide probe, e.g. in multiple copies, may be immobilized to a distinct and discrete portion or region of a single filter or membrane, e.g. to generate an array.

A combination of such techniques may also be used, e.g. several solid supports may be used which each immobilize several unique probes.

The expression "solid support" shall mean any solid material able to bind oligonucleotides by hydrophobic, ionic or covalent bridges.

"Immobilization" as used herein refers to reversible or irreversible association of the probes to said solid support by virtue of such binding. If reversible, the probes remain associated with the solid support for a time sufficient for methods of the invention to be carried out.

Numerous solid supports suitable as immobilizing moieties according to the invention, are well known in the art and widely described in the literature and generally speaking, the solid support may be any of the well-known supports or matrices which are currently widely used or proposed for immobilization, separation etc. in chemical or biochemical procedures. Such materials include, but are not limited to, any synthetic organic polymer such as polystyrene, polyvinylchloride, polyethylene; or nitrocellulose and cellulose acetate; or tosyl activated surfaces; or glass or nylon or any surface carrying a group suited for covalent coupling of nucleic acids. The immobilizing moieties may take the form of particles, sheets, gels, filters, membranes, microfibre strips, tubes or plates, fibres or capillaries, made for example of a polymeric material e.g. agarose, cellulose, alginate, teflon, latex or polystyrene or magnetic beads. Solid supports allowing the presentation of an array, preferably in a single dimension are preferred, e.g. sheets, filters, membranes, plates or biochips.

Attachment of the nucleic acid molecules to the solid support may be performed directly or indirectly. For example if a filter is used, attachment may be performed by UV-induced crosslinking. Alternatively, attachment may be performed indirectly by the use of an attachment moiety carried on the oligonucleotide probes and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules.

As used herein an "affinity binding pair" refers to two components which recognize and bind to one another specifically (ie. in preference to binding to other molecules). Such binding pairs when bound together form a complex.

Attachment of appropriate functional groups to the solid support may be performed by methods well known in the art, which include for example, attachment through hydroxyl, carboxyl, aldehyde or amino groups which may be provided by treating the solid support to provide suitable surface coatings. Solid supports presenting appropriate moieties for attachment of the binding partner may be produced by routine methods known in the art.

Attachment of appropriate functional groups to the oligonucleotide probes of the invention may be performed by ligation or introduced during synthesis or amplification, for example using primers carrying an appropriate moiety, such as biotin or a particular sequence for capture.

Conveniently, the set of probes described hereinbefore is provided in kit form.

Thus viewed from a further aspect the present invention provides a kit comprising a set of oligonucleotide probes as described hereinbefore immobilized on one or more solid supports.

Preferably, said probes are immobilized on a single solid support and each unique probe is attached to a different region of said solid support. However, when attached to multiple solid supports, said multiple solid supports form the modules which make up the kit. Especially preferably said solid support is a sheet, filter, membrane, plate or biochip.

Optionally the kit may also contain information relating to the signals generated by normal or diseased samples (as discussed in more detail hereinafter in relation to the use of the kits), standardizing materials, e.g. mRNA or cDNA from normal and/or diseased samples for comparative purposes, labels for incorporation into cDNA, adapters for introducing nucleic acid sequences for amplification purposes, primers for amplification and/or appropriate enzymes, buffers and solutions. Optionally said kit may also contain a package insert describing how the method of the invention should be performed, optionally providing standard graphs, data or software for interpretation of results obtained when performing the invention.

The use of such kits to prepare a standard diagnostic gene transcript pattern as described hereinafter forms a further aspect of the invention.

The set of probes as described herein have various uses. Principally however they are used to assess the gene expression state of a test cell to provide information relating to the organism from which said cell is derived. Thus the probes are useful in diagnosing, identifying or monitoring a cancer or stage thereof in an organism.

Thus in a further aspect the invention provides the use of a set of oligonucleotide probes or a kit as described hereinbefore to determine the gene expression pattern of a cell which pattern reflects the level of gene expression of genes to which said oligonucleotide probes bind, comprising at least the steps of:

a) isolating mRNA from said cell, which may optionally be reverse transcribed to cDNA;

b) hybridizing the mRNA or cDNA of step (a) to a set of oligonucleotide probes or a kit as defined herein; and c) assessing the amount of mRNA or cDNA hybridizing to each of said probes to produce said pattern.

The mRNA and cDNA as referred to in this method, and the methods hereinafter, encompass derivatives or copies of said molecules, e.g. copies of such molecules such as those produced by amplification or the preparation of complementary strands, but which retain the identity of the mRNA sequence, ie. would hybridize to the direct transcript (or its complementary sequence) by virtue of precise complementarity, or sequence identity, over at least a region of said molecule. It will be appreciated that complementarity will not exist over the entire region where techniques have been used which may truncate the transcript or introduce new sequences, e.g. by primer amplification. For convenience, said mRNA or cDNA is preferably amplified prior to step b). As with the oligonucleotides described herein said molecules may be modified, e.g. by using non-natural bases during synthesis providing complementarity remains. Such molecules may also carry additional moieties such as signalling or immobilizing means.

The various steps involved in the method of preparing such a pattern are described in more detail hereinafter.

As used herein "gene expression" refers to transcription of a particular gene to produce a specific mRNA product (ie. a particular splicing product). The level of gene expression may be determined by assessing the level of transcribed mRNA molecules or cDNA molecules reverse transcribed from the mRNA molecules or products derived from those molecules, e.g. by amplification.

The "pattern" created by this technique refers to information which, for example, may be represented in tabular or graphical form and conveys information about the signal associated with two or more oligonucleotides. Preferably said pattern is expressed as an array of numbers relating to the expression level associated with each probe.

Preferably, said pattern is established using the following linear model:

$$y = Xb + f \qquad \text{Equation 1}$$

wherein, X is the matrix of gene expression data and y is the response variable, b is the regression coefficient vector and f the estimated residual vector. Although many different methods can be used to establish the relationship provided in equation 1, especially preferably the partial Least Squares Regression (PLSR) method is used for establishing the relationship in equation 1.

The probes are thus used to generate a pattern which reflects the gene expression of a cell at the time of its isolation. The pattern of expression is characteristic of the circumstances under which that cells finds itself and depends on the influences to which the cell has been exposed. Thus, a characteristic gene transcript pattern standard or fingerprint (standard probe pattern) for cells from an individual with a particular cancer may be prepared and used for comparison to transcript patterns of test cells. This has clear applications in diagnosing, monitoring or identifying whether an organism is suffering from a particular cancer or stage thereof.

The standard pattern is prepared by determining the extent of binding of total mRNA (or cDNA or related product), from cells from a sample of one or more organisms with the cancer or stage thereof, to the probes. This reflects the level of transcripts which are present which correspond to each unique probe. The amount of nucleic acid material which binds to the different probes is assessed and this information together forms the gene transcript pattern standard of that cancer or stage thereof. Each such standard pattern is characteristic of the cancer or stage thereof.

In a further aspect therefore, the present invention provides a method of preparing a standard gene transcript pattern characteristic of a cancer or stage thereof in an organism comprising at least the steps of:

a) isolating mRNA from the cells of a sample of one or more organisms having the cancer or stage thereof, which may optionally be reverse transcribed to cDNA;

b) hybridizing the mRNA or cDNA of step (a) to a set of oligonucleotides or a kit as described hereinbefore specific for said cancer or stage thereof in an organism and sample thereof corresponding to the organism and sample thereof under investigation; and c) assessing the amount of mRNA or cDNA hybridizing to each of said probes to produce a characteristic pattern reflecting the level of gene expression of genes to which said oligonucleotides bind, in the sample with the cancer or stage thereof.

For convenience, said oligonucleotides are preferably immobilized on one or more solid supports.

The standard pattern for a great number of cancers and different stages thereof using particular probes may be accumulated in databases and be made available to laboratories on request.

"Disease" samples and organisms or "cancer" samples and organisms as referred to herein refer to organisms (or samples from the same) with abnormal cell proliferation e.g. in a solid mass such as a tumour. Such organisms are known to have, or which exhibit, the cancer or stage thereof under study.

"Stages" thereof refer to different stages of the cancer which may or may not exhibit particular physiological or metabolic changes, but do exhibit changes at the genetic level which may be detected as altered gene expression. It will be appreciated that during the course of a cancer the expression of different transcripts may vary. Thus at different stages, altered expression may not be exhibited for particular transcripts compared to "normal" samples. However, combining information from several transcripts which exhibit altered expression at one or more stages through the course of the cancer can be used to provide a characteristic pattern which is indicative of a particular stage of the cancer. Thus for example different stages in cancer, e.g. pre-stage I, stage I, stage II, II or IV can be identified.

"Normal" as used herein refers to organisms or samples which are used for comparative purposes. Preferably, these are "normal" in the sense that they do not exhibit any indication of, or are not believed to have, any disease or condition that would affect gene expression, particularly in respect of cancer for which they are to be used as the normal standard. However, it will be appreciated that different stages of a cancer may be compared and in such cases, the "normal" sample may correspond to the earlier stage of the cancer.

As used herein a "sample" refers to any material obtained from the organism, e.g. human or non-human animal under investigation which contains cells and includes, tissues, body fluid or body waste or in the case of prokaryotic organisms, the organism itself. "Body fluids" include blood, saliva, spinal fluid, semen, lymph. "Body waste" includes urine, expectorated matter (pulmonary patients), faeces etc. "Tissue samples" include tissue obtained by biopsy, by surgical interventions or by other means e.g. placenta. Preferably however, the samples which are examined are from areas of the body not apparently affected by the cancer. The cells in such samples are not disease cells, i.e. cancer cells, have not been in contact with such disease cells and do not originate from the site of the cancer. The "site of disease" is considered to be that area of the body which manifests the disease in a way which may be objectively determined, e.g. a tumour. Thus for example peripheral blood may be used for the diagnosis of non-haematopoietic cancers, and the blood does not require the presence of malignant or disseminated cells from the cancer in the blood. Similarly in diseases of the brain, in which no diseased cells are found in the blood due to the blood:brain barrier, peripheral blood may still be used in the methods of the invention.

It will however be appreciated that the method of preparing the standard transcription pattern and other methods of the invention are also applicable for use on living parts of eukaryotic organisms such as cell lines and organ cultures and explants.

As used herein, reference to "corresponding" sample etc. refers to cells preferably from the same tissue, body fluid or body waste, but also includes cells from tissue, body fluid or body waste which are sufficiently similar for the purposes of preparing the standard or test pattern. When used in reference to genes "corresponding" to the probes, this refers to genes which are related by sequence (which may be complementary) to the probes although the probes may reflect different splicing products of expression.

"Assessing" as used herein refers to both quantitative and qualitative assessment which may be determined in absolute or relative terms.

The invention may be put into practice as follows.

To prepare a standard transcript pattern for a particular cancer or stage thereof, sample mRNA is extracted from the cells of tissues, body fluid or body waste according to known techniques (see for example Sambrook et. al. (1989), Molecular Cloning: A laboratory manual, 2nd Ed., Cold Spring Harbor Laboratory Press, Cold Spring Harbor, N.Y.) from a diseased individual or organism.

Owing to the difficulties in working with RNA, the RNA is preferably reverse transcribed at this stage to form first strand cDNA. Cloning of the cDNA or selection from, or using, a cDNA library is not however necessary in this or other methods of the invention. Preferably, the complementary strands of the first strand cDNAs are synthesised, ie. second strand cDNAs, but this will depend on which relative strands are present in the oligonucleotide probes. The RNA may however alternatively be used directly without reverse transcription and may be labelled if so required.

Preferably the cDNA strands are amplified by known amplification techniques such as the polymerase chain reaction (PCR) by the use of appropriate primers. Alternatively, the cDNA strands may be cloned with a vector, used to transform a bacteria such as $E.\ coli$ which may then be grown to multiply the nucleic acid molecules. When the sequence of the cDNAs are not known, primers may be directed to regions of the nucleic acid molecules which have been introduced. Thus for example, adapters may be ligated to the cDNA molecules and primers directed to these portions for amplification of the cDNA molecules. Alternatively, in the case of eukaryotic samples, advantage may be taken of the polyA tail and cap of the RNA to prepare appropriate primers.

To produce the standard diagnostic gene transcript pattern or fingerprint for a particular cancer or stage thereof, the above described oligonucleotide probes are used to probe mRNA or cDNA of the diseased sample to produce a signal for hybridization to each particular oligonucleotide probe species, ie. each unique probe. A standard control gene transcript pattern may also be prepared if desired using mRNA or cDNA from a normal sample. Thus, mRNA or cDNA is brought into contact with the oligonucleotide probe under appropriate conditions to allow hybridization.

When multiple samples are probed, this may be performed consecutively using the same probes, e.g. on one or more solid supports, ie. on probe kit modules, or by simultaneously hybridizing to corresponding probes, e.g. the modules of a corresponding probe kit.

To identify when hybridization occurs and obtain an indication of the number of transcripts/cDNA molecules which become bound to the oligonucleotide probes, it is necessary to identify a signal produced when the transcripts (or related molecules) hybridize (e.g. by detection of double stranded nucleic acid molecules or detection of the number of molecules which become bound, after removing unbound molecules, e.g. by washing).

In order to achieve a signal, either or both components which hybridize (ie. the probe and the transcript) carry or form a signalling means or a part thereof. This "signalling means" is any moiety capable of direct or indirect detection by the generation or presence of a signal. The signal may be any detectable physical characteristic such as conferred by radiation emission, scattering or absorption properties, magnetic properties, or other physical properties such as charge, size or binding properties of existing molecules (e.g. labels) or molecules which may be generated (e.g. gas emission etc.). Techniques are preferred which allow signal amplification, e.g. which produce multiple signal events from a single active binding site, e.g. by the catalytic action of enzymes to produce multiple detectable products.

Conveniently the signalling means may be a label which itself provides a detectable signal. Conveniently this may be achieved by the use of a radioactive or other label which may be incorporated during cDNA production, the preparation of complementary cDNA strands, during amplification of the target mRNA/cDNA or added directly to target nucleic acid molecules.

Appropriate labels are those which directly or indirectly allow detection or measurement of the presence of the transcripts/cDNA. Such labels include for example radiolabels, chemical labels, for example chromophores or fluorophores (e.g. dyes such as fluorescein and rhodamine), or reagents of high electron density such as ferritin, haemocyanin or colloidal gold. Alternatively, the label may be an enzyme, for example peroxidase or alkaline phosphatase, wherein the presence of the enzyme is visualized by its interaction with a suitable entity, for example a substrate. The label may also form part of a signalling pair wherein the other member of the pair is found on, or in close proximity to, the oligonucleotide probe to which the transcript/cDNA binds, for example, a fluorescent compound and a quench fluorescent substrate may be used. A label may also be provided on a different entity, such as an antibody, which recognizes a peptide moiety attached to the transcripts/cDNA, for example attached to a base used during synthesis or amplification.

A signal may be achieved by the introduction of a label before, during or after the hybridization step. Alternatively, the presence of hybridizing transcripts may be identified by other physical properties, such as their absorbance, and in which case the signalling means is the complex itself.

The amount of signal associated with each oligonucleotide probe is then assessed. The assessment may be quantitative or qualitative and may be based on binding of a single transcript species (or related cDNA or other products) to each probe, or binding of multiple transcript species to multiple copies of each unique probe. It will be appreciated that quantitative results will provide further information for the transcript fingerprint of the cancer which is compiled. This data may be expressed as absolute values (in the case of macroarrays) or may be determined relative to a particular standard or reference e.g. a normal control sample.

Furthermore it will be appreciated that the standard diagnostic gene pattern transcript may be prepared using one or more disease samples (and normal samples if used) to perform the hybridization step to obtain patterns not biased towards a particular individual's variations in gene expression.

The use of the probes to prepare standard patterns and the standard diagnostic gene transcript patterns thus produced for the purpose of identification or diagnosis or monitoring of a particular cancer or stage thereof in a particular organism forms a further aspect of the invention.

Once a standard diagnostic fingerprint or pattern has been determined for a particular cancer or stage thereof using the selected oligonucleotide probes, this information can be used to identify the presence, absence or extent or stage of that cancer in a different test organism or individual.

To examine the gene expression pattern of a test sample, a test sample of tissue, body fluid or body waste containing cells, corresponding to the sample used for the preparation of the standard pattern, is obtained from a patient or the organism to be studied. A test gene transcript pattern is then prepared as described hereinbefore as for the standard pattern.

In a further aspect therefore, the present invention provides a method of preparing a test gene transcript pattern comprising at least the steps of:

a) isolating mRNA from the cells of a sample of said test organism, which may optionally be reverse transcribed to cDNA;

b) hybridizing the mRNA or cDNA of step (a) to a set of oligonucleotides or a kit as described hereinbefore specific for a cancer or stage thereof in an organism and sample thereof corresponding to the organism and sample thereof under investigation; and c) assessing the amount of mRNA or cDNA hybridizing to each of said probes to produce said pattern reflecting the level of gene expression of genes to which said oligonucleotides bind, in said test sample.

This test pattern may then be compared to one or more standard patterns to assess whether the sample contains cells having the cancer or stage thereof.

Thus viewed from a further aspect the present invention provides a method of diagnosing or identifying or monitoring a cancer or stage thereof in an organism, comprising the steps of:

a) isolating mRNA from the cells of a sample of said organism, which may optionally be reverse transcribed to cDNA;

b) hybridizing the mRNA or cDNA of step (a) to a set of oligonucleotides or a kit as described hereinbefore specific for said cancer or stage thereof in an organism and sample thereof corresponding to the organism and sample thereof under investigation;

c) assessing the amount of mRNA or cDNA hybridizing to each of said probes to produce a characteristic pattern reflecting the level of gene expression of genes to which said oligonucleotides bind, in said sample; and d) comparing said pattern to a standard diagnostic pattern prepared according to the method of the invention using a sample from an organism corresponding to the organism and sample under investigation to determine the presence of said cancer or a stage thereof in the organism under investigation.

The method up to and including step c) is the preparation of a test pattern as described above.

As referred to herein, "diagnosis" refers to determination of the presence or existence of a cancer or stage thereof in an organism. "Monitoring" refers to establishing the extent of a cancer, particularly when an individual is known to be suffering from cancer, for example to monitor the effects of treatment or the development of a cancer, e.g. to determine the suitability of a treatment or provide a prognosis.

The presence of the cancer or stage thereof may be determined by determining the degree of correlation between the standard and test samples' patterns. This necessarily takes into account the range of values which are obtained for normal and diseased samples. Although this can be established by obtaining standard deviations for several representative samples binding to the probes to develop the standard, it will be appreciated that single samples may be sufficient to generate the standard pattern to identify a cancer if the test sample exhibits close enough correlation to that standard. Conveniently, the presence, absence, or extent of a cancer or stage thereof in a test sample can be predicted by inserting the data relating to the expression level of informative probes in test sample into the standard diagnostic probe pattern established according to equation 1.

Data generated using the above mentioned methods may be analysed using various techniques from the most basic visual representation (e.g. relating to intensity) to more complex data manipulation to identify underlying patterns which reflect the interrelationship of the level of expression of each gene to which the various probes bind, which may be quantified and expressed mathematically. Conveniently, the raw data thus generated may be manipulated by the data processing and statistical methods described hereinafter, particularly normalizing and standardizing the data and fitting the data to a classification model to determine whether said test data reflects the pattern of a particular cancer or stage thereof.

The methods described herein may be used to identify, monitor or diagnose a cancer or its stage or progression, for which the oligonucleotide probes are informative. "Informative" probes as described herein, are those which reflect genes which have altered expression in the cancer in question, or particular stages thereof. Probes of the invention may not be sufficiently informative for diagnostic purposes when used alone, but are informative when used as one of several probes to provide a characteristic pattern, e.g. in a set as described hereinbefore.

Preferably said probes correspond to genes which are systemically affected by said cancer or stage thereof. Especially preferably said genes, from which transcripts are derived which bind to probes of the invention, are moderately or highly expressed. The advantage of using probes directed to moderately or highly expressed genes is that smaller clinical samples are required for generating the necessary gene expression data set, e.g. less than 1 ml blood samples.

Furthermore, it has been found that such genes which are already being actively transcribed tend to be more prone to being influenced, in a positive or negative way, by new stimuli. In addition, since transcripts are already being produced at levels which are generally detectable, small changes in those levels are readily detectable as for example, a certain detectable threshold does not need to be reached.

In preferred methods of the invention, the set of probes of the invention are informative for a variety of different cancers or stages thereof. A sub-set of the probes disclosed herein may be used for diagnosis, identification or monitoring a particular cancer or stage thereof.

Cancers for which the probes may be used for diagnosis, identification and monitoring include stomach, lung, breast, prostate gland, bowel, skin, colon and ovary cancer. Especially preferably the probes are used for breast cancer analysis.

The diagnostic method may be used alone as an alternative to other diagnostic techniques or in addition to such techniques. For example, methods of the invention may be used as an alternative or additive diagnostic measure to diagnosis using imaging techniques such as Magnetic Resonance Imagine (MRI), ultrasound imaging, nuclear imaging or X-ray imaging, for example in the identification and/or diagnosis of tumours.

The methods of the invention may be performed on cells from prokaryotic or eukaryotic organisms which may be any eukaryotic organisms such as human beings, other mammals and animals, birds, insects, fish and plants, and any prokaryotic organism such as a bacteria.

Preferred non-human animals on which the methods of the invention may be conducted include, but are not limited to mammals, particularly primates, domestic animals, livestock and laboratory animals. Thus preferred animals for diagnosis include mice, rats, guinea pigs, cats, dogs, pigs, cows, goats, sheep, horses. Particularly preferably cancer of humans is diagnosed, identified or monitored.

As described above, the sample under study may be any convenient sample which may be obtained from an organism. Preferably however, as mentioned above, the sample is obtained from a site distant to the site of disease and the cells in such samples are not disease cells, have not been in contact with such cells and do not originate from the site of the disease. In such cases, although preferably absent, the sample may contain cells which do not fulfil these criteria. However, since the probes of the invention are concerned with transcripts whose expression is altered in cells which do satisfy these criteria, the probes are specifically directed to detecting changes in transcript levels in those cells even if in the presence of other, background cells.

It has been found that the cells from such samples show significant and informative variations in the gene expression of a large number of genes. Thus, the same probe (or several probes) may be found to be informative in determinations regarding two or more cancers, or stages thereof by virtue of the particular level of transcripts binding to that probe or the interrelationship of the extent of binding to that probe relative to other probes. As a consequence, it is possible to use a relatively small number of probes for screening for multiple cancers. This has consequences with regard to the selection of probes, but also for the use of a single set of probes for more than one diagnosis.

Thus, the present invention also provides sets of probes for diagnosing, identifying or monitoring two or more cancers or stages thereof, wherein at least one of said probes is suitable for said diagnosing, identifying or monitoring at least two of said cancers or stages thereof, and kits and methods of using the same. Preferably at least 5 probes, e.g. from 5 to 15 probes, are used in at least two diagnoses.

Thus, in a further preferred aspect, the present invention provides a method of diagnosis or identification or monitoring as described hereinbefore for the diagnosis, identification or monitoring of two or more cancers or stages thereof in an organism, wherein said test pattern produced in step c) of the diagnostic method is compared in step d) to at least two standard diagnostic patterns prepared as described previously, wherein each standard diagnostic pattern is a pattern generated for a different cancer or stage thereof.

Whilst in a preferred aspect the methods of assessment concern the development of a gene transcript pattern from a test sample and comparison of the same to a standard pattern, the elevation or depression of expression of certain markers may also be examined by examining the products of expression and the level of those products. Thus a standard pattern in relation to the expressed product may be generated.

In such methods the levels of expression of a set of polypeptides encoded by the gene to which a primary oligonucleotide or a derived oligonucleotide, binds, are analysed.

Various diagnostic methods may be used to assess the amount of polypeptides (or fragments thereof) which are present. The presence or concentration of polypeptides may be examined, for example by the use of a binding partner to said polypeptide (e.g. an antibody), which may be immobilized, to separate said polypeptide from the sample and the amount of polypeptide may then be determined.

"Fragments" of the polypeptides refers to a domain or region of said polypeptide, e.g. an antigenic fragment, which is recognizable as being derived from said polypeptide to allow binding of a specific binding partner. Preferably such a fragment comprises a significant portion of said polypeptide and corresponds to a product of normal post-synthesis processing.

Thus in a further aspect the present invention provides a method of preparing a standard gene transcript pattern characteristic of a cancer or stage thereof in an organism comprising at least the steps of:

a) releasing target polypeptides from a sample of one or more organisms having the cancer or stage thereof;

b) contacting said target polypeptides with one or more binding partners, wherein each binding partner is specific to a marker polypeptide (or a fragment thereof) encoded by the gene to which a primary oligonucleotide (or derived sequence) binds, to allow binding of said binding partners to said target polypeptides, wherein said marker polypeptides are specific for said cancer in an organism and sample thereof corresponding to the organism and sample thereof under investigation; and c) assessing the target polypeptide binding to said binding partners to produce a characteristic pattern reflecting the level of gene expression of genes which express said marker polypeptides, in the sample with the cancer or stage thereof.

As used herein "target polypeptides" refer to those polypeptides present in a sample which are to be detected and "marker polypeptides" are polypeptides which are encoded by the genes to which primary oligonucleotides or derived oligonucleotides bind, ie. genes within the gene families. The target and marker polypeptides are identical or at least have areas of high similarity, e.g. epitopic regions to allow recognition and binding of the binding partner.

"Release" of the target polypeptides refers to appropriate treatment of a sample to provide the polypeptides in a form accessible for binding of the binding partners, e.g. by lysis of cells where these are present. The samples used in this case need not necessarily comprise cells as the target polypeptides may be released from cells into the surrounding tissue or fluid, and this tissue or fluid may be analysed, e.g. urine or blood. Preferably however the preferred samples as described herein are used. "Binding partners" comprise the separate entities which together make an affinity binding pair as described above, wherein one partner of the binding pair is the target or marker polypeptide and the other partner binds specifically to that polypeptide, e.g. an antibody.

Various arrangements may be envisaged for detecting the amount of binding pairs which form. In its simplest form, a sandwich type assay e.g. an immunoassay such as an ELISA, may be used in which an antibody specific to the polypeptide and carrying a label (as described elsewhere herein) may be bound to the binding pair (e.g. the first antibody:polypeptide pair) and the amount of label detected.

Other methods as described herein may be similarly modified for analysis of the protein product of expression rather than the gene transcript and related nucleic acid molecules.

Thus a further aspect of the invention provides a method of preparing a test gene transcript pattern comprising at least the steps of:

a) releasing target polypeptides from a sample of said test organism;

b) contacting said target polypeptides with one or more binding partners, wherein each binding partner is specific to a marker polypeptide (or a fragment thereof) encoded by the gene to which a primary oligonucleotide (or derived sequence) binds, to allow binding of said binding partners to said target polypeptides, wherein said marker polypeptides are specific for said cancer in an organism and sample thereof corresponding to the organism and sample thereof under investigation; and c) assessing the target polypeptide binding to said binding partners to produce a characteristic pattern reflecting the level of gene expression of genes which express said marker polypeptides, in said test sample.

A yet further aspect of the invention provides a method of diagnosing or identifying or monitoring a cancer or stage thereof in an organism comprising the steps of:

a) releasing target polypeptides from a sample of said organism;

b) contacting said target polypeptides with one or more binding partners, wherein each binding partner is specific to a marker polypeptide (or a fragment thereof) encoded by the gene to which a primary oligonucleotide (or derived sequence) binds, to allow binding of said binding partners to said target polypeptides, wherein said marker polypeptides are specific for said cancer in an organism and sample thereof corresponding to the organism and sample thereof under investigation; and c) assessing the target polypeptide binding to said binding partners to produce a characteristic pattern reflecting the level of gene expression of genes which express said marker polypeptides in said sample; and d) comparing said pattern to a standard diagnostic pattern prepared as described hereinbefore using a sample from an organism corresponding to the organism and sample under investigation to determine the degree of correlation indicative of the presence of said cancer or a stage thereof in the organism under investigation.

The methods of generating standard and test patterns and diagnostic techniques rely on the use of informative oligonucleotide probes to generate the gene expression data. In some cases it will be necessary to select these informative probes for a particular method, e.g. to diagnose a particular cancer, from a selection of available probes, e.g. the Table 2 and/or 3 oligonucleotides, the Table 2 and/or 3 derived oligonucleotides, their complementary sequences and functionally equivalent oligonucleotides and optionally the Table 4 oligonucleotides, their derived oligonucleotides, complementary sequences and functionally equivalent oligonucleotides. Said derived oligonucleotides include oligonucleotides derived from the genes corresponding to the sequences provided in those tables, e.g. the genes set forth in Tables 2, 5 or 6 (see the Accession numbers), or the complementary sequences thereof. The following methodology describes a convenient method for identifying such informative probes, or more particularly how to select a suitable sub-set of probes from the probes described herein.

Probes for the analysis of a particular cancer or stage thereof, may be identified in a number of ways known in the prior art, including by differential expression or by library subtraction (see for example WO98/49342). As described in PCT/GB03/005102 and as described hereinafter, in view of the high information content of most transcripts, as a starting point one may also simply analyse a random sub-set of mRNA or cDNA species corresponding to the family of sequence described herein and pick the most informative probes from that sub-set. The following method describes the use of immobilized oligonucleotide probes (e.g. the probes of the invention) to which mRNA (or related molecules) from different samples are bound to identify which probes are the most informative to identify a particular type of cancer, e.g. a disease sample.

The immobilized probes can be derived from various unrelated or related organisms; the only requirement is that the immobilised probes should bind specifically to their homologous counterparts in test organisms. Probes can also be derived from commercially available or public databases and immobilized on solid supports. The selected probes necessarily correspond to one of the genes in the gene sequence families described herein, but the probes of interest may be randomly selected from within that entire group of families.

The length of the probes immobilised on the solid support should be long enough to allow for specific binding to the target sequences. The immobilised probes can be in the form of DNA, RNA or their modified products or PNAs (peptide nucleic acids). Preferably, the probes immobilised should bind specifically to their homologous counterparts representing highly and moderately expressed genes in test organisms. Conveniently the probes which are used are the probes described herein.

The gene expression pattern of cells in biological samples can be generated using prior art techniques such as microarray or macroarray as described below or using methods described herein. Several technologies have now been developed for monitoring the expression level of a large number of genes simultaneously in biological samples, such as, high-density oligoarrays (Lockhart et al., 1996, Nat. Biotech., 14, p 1675-1680), cDNA microarrays (Schena et al, 1995, Science, 270, p 467-470) and cDNA macroarrays (Maier E et al., 1994, Nucl. Acids Res., 22, p 3423-3424; Bernard et al., 1996, Nucl. Acids Res., 24, p 1435-1442).

In high-density oligoarrays and cDNA microarrays, hundreds and thousands of probe oligonucleotides or cDNAs, are spotted onto glass slides or nylon membranes, or synthesized on biochips. The mRNA isolated from the test and reference samples are labelled by reverse transcription with a red or green fluorescent dye, mixed, and hybridised to the microarray. After washing, the bound fluorescent dyes are detected by a laser, producing two images, one for each dye. The resulting ratio of the red and green spots on the two images provides the information about the changes in expression levels of genes in the test and reference samples. Alternatively, single channel or multiple channel microarray studies can also be performed.

In cDNA macroarray, different cDNAs are spotted on a solid support such as nylon membranes in excess in relation to the amount of test mRNA that can hybridise to each spot. mRNA isolated from test samples is radio-labelled by reverse transcription and hybridised to the immobilised probe cDNA. After washing, the signals associated with labels hybridising specifically to immobilised probe cDNA are detected and quantified. The data obtained in macroarray contains information about the relative levels of transcripts present in the test samples. Whilst macroarrays are only suitable to monitor the expression of a limited number of genes, microarrays can be used to monitor the expression of several thousand genes simultaneously and is, therefore, a preferred choice for large-scale gene expression studies.

A macroarray technique for generating the gene expression data set has been used to illustrate the probe identification method described herein. For this purpose, mRNA is isolated from samples of interest and used to prepare labelled target molecules, e.g. mRNA or cDNA as described above. The labelled target molecules are then hybridised to probes immobilised on the solid support. Various solid supports can be used for the purpose, as described previously. Following hybridization, unbound target molecules are removed and signals from target molecules hybridizing to immobilised probes quantified. If radio labelling is performed, Phospho-Imager can be used to generate an image file that can be used to generate a raw data set. Depending on the nature of label chosen for labelling the target molecules, other instruments can also be used, for example, when fluorescence is used for labelling, a FluoroImager can be used to generate an image file from the hybridised target molecules.

The raw data corresponding to mean intensity, median intensity, or volume of the signals in each spot can be acquired from the image file using commercially available software for image analysis. However, the acquired data needs to be corrected for background signals and normalized prior to analysis, since, several factors can affect the quality and quantity of the hybridising signals. For example, variations in the quality and quantity of mRNA isolated from sample to sample, subtle variations in the efficiency of labelling target molecules during each reaction, and variations in the amount of unspecific binding between different macroarrays can all contribute to noise in the acquired data set that must be corrected for prior to analysis.

Background correction can be performed in several ways. The lowest pixel intensity within a spot can be used for background subtraction or the mean or median of the line of pixels around the spots' outline can be used for the purpose. One can also define an area representing the background intensity based on the signals generated from negative controls and use the average intensity of this area for background subtraction.

The background corrected data can then be transformed for stabilizing the variance in the data structure and normalized for the differences in probe intensity. Several transformation techniques have been described in the literature and a brief overview can be found in Cui, Kerr and Churchill http://www jax.org/research/churchill/research/expression/Cui-Transform.pdf). Normalization can be performed by dividing the intensity of each spot with the collective intensity, average intensity or median intensity of all the spots in a macroarray or a group of spots in a macroarray in order to obtain the relative intensity of signals hybridising to immobilised probes in a macroarray. Several methods have been described for normalizing gene expression data (Richmond and Somerville, 2000, Current Opin. Plant Biol., 3, p 108-116; Finkelstein et al., 2001, In "Methods of Microarray Data Analysis. Papers from CAMDA, Eds. Lin & Johnsom, Kluwer Academic, p 57-68; Yang et al., 2001, In "Optical Technologies and Informatics", Eds. Bittner, Chen, Dorsel & Dougherty, Proceedings of SPIE, 4266, p 141-152; Dudoit et al, 2000, J. Am. Stat. Ass., 97, p 77-87; Alter et al 2000, supra; Newton et al., 2001, J. Comp. Biol., 8, p 37-52). Generally, a scaling factor or function is first calculated to correct the intensity effect and then used for normalising the intensities. The use of external controls has also been suggested for improved normalization.

One other major challenge encountered in large-scale gene expression analysis is that of standardization of data collected from experiments performed at different times. We have observed that gene expression data for samples acquired in the same experiment can be efficiently compared following background correction and normalization. However, the data from samples acquired in experiments performed at different times requires further standardization prior to analysis. This is because subtle differences in experimental parameters between different experiments, for example, differences in the quality and quantity of mRNA extracted at different times, differences in time used for target molecule labelling, hybridization time or exposure time, can affect the measured values. Also, factors such as the nature of the sequence of transcripts under investigation (their GC content) and their amount in relation to the each other determines how they are affected by subtle variations in the experimental processes. They determine, for example, how efficiently first strand cDNAs, corresponding to a particular transcript, are transcribed and labelled during first strand synthesis, or how efficiently the corresponding labelled target molecules bind to their complementary sequences during hybridization. Batch to batch difference in the printing process is also a major factor for variation in the generated expression data.

Failure to properly address and rectify for these influences leads to situations where the differences between the experimental series may overshadow the main information of interest contained in the gene expression data set, i.e. the differences within the combined data from the different experimental series. Hence, when required the expression data should be batch-adjusted prior to data analysis.

Monitoring the expression of a large number of genes in several samples leads to the generation of a large amount of data that is too complex to be easily interpreted. Several unsupervised and supervised multivariate data analysis techniques have already been shown to be useful in extracting meaningful biological information from these large data sets. Cluster analysis is by far the most commonly used technique for gene expression analysis, and has been performed to identify genes that are regulated in a similar manner, and or identifying new/unknown tumour classes using gene expression profiles (Eisen et al., 1998, PNAS, 95, p 14863-14868, Alizadeh et al. 2000, supra, Peron et al. 2000, Nature, 406, p 747-752; Ross et al, 2000, Nature Genetics, 24(3), p 227-235; Herwig et al., 1999, Genome Res., 9, p 1093-1105; Tamayo et al, 1999, Science, PNAS, 96, p 2907-2912).

In the clustering method, genes are grouped into functional categories (clusters) based on their expression profile, satisfying two criteria: homogeneity—the genes in the same cluster are highly similar in expression to each other; and separation—genes in different clusters have low similarity in expression to each other.

Examples of various clustering techniques that have been used for gene expression analysis include hierarchical clustering (Eisen et al., 1998, supra; Alizadeh et al. 2000, supra; Perou et al. 2000, supra; Ross et al, 2000, supra), K-means clustering (Herwig et al., 1999, supra; Tavazoie et al, 1999, Nature Genetics, 22(3), p. 281-285), gene shaving (Hastie et al., 2000, Genome Biology, 1(2), research 0003.1-0003.21), block clustering (Tibshirani et al., 1999, Tech report Univ Stanford.) Plaid model (Lazzeroni, 2002, Stat. Sinica, 12, p 61-86), and self-organizing maps (Tamayo et al. 1999, supra). Also, related methods of multivariate statistical analysis, such as those using the singular value decomposition (Alter et al., 2000, PNAS, 97(18), p 10101-10106; Ross et al. 2000, supra) or multidimensional scaling can be effective at reducing the dimensions of the objects under study.

However, methods such as cluster analysis and singular value decomposition are purely exploratory and only provide a broad overview of the internal structure present in the data. They are unsupervised approaches in which the available information concerning the nature of the class under investigation is not used in the analysis. Often, the nature of the biological perturbation to which a particular sample has been subjected is known. For example, it is sometimes known whether the sample whose gene expression pattern is being analysed derives from a diseased or healthy individual. In such instances, discriminant analysis can be used for classifying samples into various groups based on their gene expression data.

In such an analysis one builds the classifier by training the data that is capable of discriminating between member and non-members of a given class. The trained classifier can then be used to predict the class of unknown samples. Examples of discrimination methods that have been described in the literature include Support Vector Machines (Brown et al, 2000, PNAS, 97, p 262-267), Nearest Neighbour (Dudoit et al., 2000, supra), Classification trees (Dudoit et al., 2000, supra), Voted classification (Dudoit et al., 2000, supra), Weighted Gene voting (Golub et al. 1999, supra), and Bayesian classification (Keller et al. 2000, Tec report Univ of Washington). Also a technique in which PLS (Partial Least Square) regression analysis is first used to reduce the dimensions in the gene expression data set followed by classification using logistic discriminant analysis and quadratic discriminant analysis (LD and QDA) has recently been described (Nguyen & Rocke, 2002, Bioinformatics, 18, p 39-50 and 1216-1226).

A challenge that gene expression data poses to classical discriminatory methods is that the number of genes whose expression are being analysed is very large compared to the number of samples being analysed. However in most cases only a small fraction of these genes are informative in discriminant analysis problems. Moreover, there is a danger that the noise from irrelevant genes can mask or distort the information from the informative genes. Several methods have been suggested in literature to identify and select genes that are informative in microarray studies, for example, t-statistics (Dudoit et al, 2002, J. Am. Stat. Ass., 97, p 77-87), analysis of variance (Kerr et al., 2000, PNAS, 98, p 8961-8965), Neighbourhood analysis (Golub et al, 1999, supra), Ratio of between groups to within groups sum of squares (Dudoit et al., 2002, supra), Non parametric scoring (Park et al., 2002, Pacific Symposium on Biocomputing, p 52-63) and Likelihood selection (Keller et al., 2000, supra).

In the methods described herein the gene expression data that has been normalized and standardized is analysed by using Partial Least Squares Regression (PLSR). Although PLSR is primarily a method used for regression analysis of continuous data (see Appendix A), it can also be utilized as a method for model building and discriminant analysis using a dummy response matrix based on a binary coding. The class assignment is based on a simple dichotomous distinction such as breast cancer (class 1)/healthy (class 2), or a multiple distinction based on multiple disease diagnosis such as breast cancer (class 1)/ovarian cancer (class 2)/healthy (class 3). The list of diseases for classification can be increased depending upon the samples available corresponding to other cancers or stages thereof.

PLSR applied as a classification method is referred to as PLS-DA (DA standing for Discriminant analysis). PLS-DA is an extension of the PLSR algorithm in which the Y-matrix is a dummy matrix containing n rows (corresponding to the number of samples) and K columns (corresponding to the number of classes). The Y-matrix is constructed by inserting 1 in the kth column and −1 in all the other columns if the corresponding ith object of X belongs to class k. By regressing Y onto X, classification of a new sample is achieved by selecting the group corresponding to the largest component of the fitted, $\hat{y}(x)=(\hat{y}_1(x), \hat{y}_2(x), \ldots, \hat{y}_k(x))$. Thus, in a −1/1 response matrix, a prediction value below 0 means that the sample belongs to the class designated as −1, while a prediction value above 0 implies that the sample belongs to the class designated as 1.

An advantage of PLSR-DA is that the results obtained can be easily represented in the form of two different plots, the score and loading plots. Score plots represent a projection of the samples onto the principal components and shows the distribution of the samples in the classification model and their relationship to one another. Loading plots display correlations between the variables present in the data set.

It is usually recommended to use PLS-DA as a starting point for the classification problem due to its ability to handle collinear data, and the property of PLSR as a dimension reduction technique. Once this purpose has been satisfied, it is possible to use other methods such as Linear discriminant analysis, LDA, that has been shown to be effective in extracting further information, Indahl et al. (1999, Chem. and Intell. Lab. Syst., 49, p 19-31). This approach is based on first decomposing the data using PLS-DA, and then using the scores vectors (instead of the original variables) as input to LDA. Further details on LDA can be found in Duda and Hart (Classification and Scene Analysis, 1973, Wiley, USA).

The next step following model building is of model validation. This step is considered to be amongst the most important aspects of multivariate analysis, and tests the "goodness" of the calibration model which has been built. In this work, a cross validation approach has been used for validation. In this approach, one or a few samples are kept out in each segment while the model is built using a full cross-validation on the basis of the remaining data. The samples left out are then used for prediction/classification. Repeating the simple cross-validation process several times holding different samples out for each cross-validation leads to a so-called double cross-validation procedure. This approach has been shown to work well with a limited amount of data, as is the case in some of the Examples described here. Also, since the cross validation step is repeated several times the dangers of model bias and overfitting are reduced.

Once a calibration model has been built and validated, genes exhibiting an expression pattern that is most relevant for describing the desired information in the model can be selected by techniques described in the prior art for variable selection, as mentioned elsewhere. Variable selection will help in reducing the final model complexity, provide a parsimonious model, and thus lead to a reliable model that can be used for prediction. Moreover, use of fewer genes for the purpose of providing diagnosis will reduce the cost of the diagnostic product. In this way informative probes which would bind to the genes of relevance may be identified.

We have found that after a calibration model has been built, statistical techniques like Jackknife (Effron, 1982, The Jackknife, the Bootstrap and other resampling plans. Society for Industrial and Applied mathematics, Philadelphia, USA), based on resampling methodology, can be efficiently used to select or confirm significant variables (informative probes). The approximate uncertainty variance of the PLS regression coefficients B can be estimated by:

$$S^2 B = \sum_{m=1}^{M} ((B - B_m)g)^2$$

where
$S^2B$=estimated uncertainty variance of B;
B=the regression coefficient at the cross validated rank A using all the N objects;
$B_m$=the regression coefficient at the rank A using all objects except the object(s) left out in cross validation segment m; and
g=scaling coefficient (here: g=1).

In our approach, Jackknife has been implemented together with cross-validation. For each variable the difference between the B-coefficients $B_i$ in a cross-validated sub-model and $B_{tot}$ for the total model is first calculated. The sum of the squares of the differences is then calculated in all sub-models to obtain an expression of the variance of the $B_i$ estimate for a variable. The significance of the estimate of $B_i$ is calculated using the t-test. Thus, the resulting regression coefficients can be presented with uncertainty limits that correspond to 2 Standard Deviations, and from that significant variables are detected.

No further details as to the implementation or use of this step are provided here since this has been implemented in commercially available software, The Unscrambler, CAMO ASA, Norway. Also, details on variable selection using Jackknife can be found in Westad & Martens (2000, J. Near Inf. Spectr., 8, p 117-124).

The following approach can be used to select informative probes from a gene expression data set:

a) keep out one unique sample (including its repetitions if present in the data set) per cross validation segment;
b) build a calibration model (cross validated segment) on the remaining samples using PLSR-DA;
c) select the significant genes for the model in step b) using the Jackknife criterion;
d) repeat the above 3 steps until all the unique samples in the data set are kept out once (as described in step a). For example, if 75 unique samples are present in the data set, 75 different calibration models are built resulting in a collection of 75 different sets of significant probes;
e) select the most significant variables using the frequency of occurrence criterion in the generated sets of significant probes in step d). For example, a set of probes appearing in all sets (100%) are more informative than probes appearing in only 50% of the generated sets in step d).

Once the informative probes for a disease have been selected, a final model is made and validated. The two most commonly used ways of validating the model are cross-validation (CV) and test set validation. In cross-validation, the data is divided into k subsets. The model is then trained k times, each time leaving out one of the subsets from training, but using only the omitted subset to compute error criterion, RMSEP (Root Mean Square Error of Prediction). If k equals the sample size, this is called "leave-one-out" cross-validation. The idea of leaving one or a few samples out per validation segment is valid only in cases where the covariance between the various experiments is zero. Thus, one sample at-a-time approach can not be justified in situations containing replicates since keeping only one of the replicates out will introduce a systematic bias in our analysis. The correct approach in this case will be to leave out all replicates of the same samples at a time since that would satisfy assumptions of zero covariance between the CV-segments.

The second approach for model validation is to use a separate test-set for validating the calibration model. This requires running a separate set of experiments to be used as a test set. This is the preferred approach given that real test data are available.

The final model is then used to identify a cancer or stage thereof in test samples. For this purpose, expression data of selected informative genes is generated from test samples and then the final model is used to determine whether a sample belongs to a diseased or non-diseased class or has a cancer or stage thereof.

Preferably a model for classification purposes is generated by using the data relating to the probes identified according to the above described method. Preferably the sample is as described previously. Preferably the oligonucleotides which are immobilized in step (a) are randomly selected from within the family described hereinbefore, but alternatively may be selected to represent the different families, e.g. by selecting one or more of the oligonucleotides corresponding to genes encoding proteins with common functions in different families. Especially preferably, said selection is made to encompass oligonucleotides derived from genes of family (i) and (ii). Such oligonucleotides may be of considerable length, e.g. if using cDNA (which is encompassed within the scope of the term "oligonucleotide"). The identification of such cDNA molecules as useful probes allows the development of shorter oligonucleotides which reflect the specificity of the cDNA molecules but are easier to manufacture and manipulate.

The above described model may then be used to generate and analyse data of test samples and thus may be used for the diagnostic methods of the invention. In such methods the data generated from the test sample provides the gene expression data set and this is normalized and standardized as described above. This is then fitted to the calibration model described above to provide classification.

The method described herein can also be used to simultaneously select informative probes for several cancers. Depending upon which cancers have been included in the calibration or training set, informative probes can be selected for the said cancers. The informative probes selected for one cancer may or may not be similar to the informative probes selected for another cancer of interest. It is the pattern with which the selected genes are expressed in relation to each other during a cancer or stage thereof, that determines whether or not they are informative for the cancer or stage thereof.

In other words, informative genes are selected based on how their expression correlates with the expression of other selected informative genes under the influence of responses generated by the cancer or stage thereof under investigation.

For the purpose of isolating informative probes or identifying several cancers and stages thereof simultaneously, the gene expression data set must contain the information on how genes are expressed when the subject has a particular cancer or stage thereof under investigation. The data set is generated from a set of healthy or diseased samples, where a particular sample may contain the information of only one cancer or stage thereof or may also contain information about multiple cancers or stages thereof. Hence, the method also teaches an efficient experimental design to reduce the number of samples required for isolating informative probes by selecting samples representing more than one cancer or stage thereof.

As mentioned previously, in view of the high information content of most transcripts, the identification and selection of informative probes for use in diagnosing, monitoring or identifying a particular cancer or stage thereof may be dramatically simplified. Thus the pool of genes from which a selection may be made to identify informative probes may be radically reduced.

Unlike, in prior art technologies where informative probes are selected from a population of thousands of genes that are being expressed in a cell, like in microarray, in the method described herein, the informative probes are selected from a limited number of genes as described in the gene sequence families described hereinbefore. From within these families, probes of interest may be randomly selected.

Thus in a preferred aspect, said set of oligonucleotides are randomly selected from the primary oligonucleotides as described hereinbefore.

As referred to herein "random" refers to selection which is not biased based on the extent of information carried by the transcripts in relation to the cancer or organism under study, ie. without bias towards their likely utility as informative probes. Whilst a random selection may be made from a pool of transcripts (or related products) which have been biased, e.g. to highly or moderately expressed transcripts, preferably random selection is made from a pool of transcripts not biased or selected by a sequence-based criterion. The larger set may therefore contain oligonucleotides corresponding to highly and moderately expressed genes, or alternatively, may be enriched for those corresponding to the highly and moderately expressed genes.

Random selection from highly and moderately expressed genes can be achieved in a wide variety of ways. For example, by randomly picking a significant number of cDNA clones from a cDNA library constructed from a biological specimen under investigation containing clones corresponding to the gene sequence families described hereinbefore. Since, in a cDNA library, the cDNA clones corresponding to transcripts present in high or moderate amount are more frequently present than transcripts corresponding to cDNA present in low amount, the former will tend to be picked up more frequently than the latter. A pool of cDNA enriched for those corresponding to highly and moderately expressed genes can be isolated by this approach.

To identify genes that are expressed in high or moderate amount among the isolated population for use in methods of the invention, the information about the relative level of their transcripts in samples of interest can be generated using several prior art techniques. Both non-sequence based methods, such as differential display or RNA fingerprinting, and sequence-based methods such as microarrays or macroarrays can be used for the purpose. Alternatively, specific primer sequences for highly and moderately expressed genes can be designed and methods such as quantitative RT-PCR can be used to determine the levels of highly and moderately expressed genes. Hence, a skilled practitioner may use a variety of techniques which are known in the art for determining the relative level of mRNA in a biological sample.

Especially preferably the sample for the isolation of mRNA in the above described method is as described previously and is preferably not from the site of disease and the cells in said sample are not disease cells and have not contacted disease cells, for example the use of a peripheral blood sample for detection of non-haematopoietic cancer, e.g. breast cancer.

The following examples are given by way of illustration only in which the Figures referred to are as follows.

EXAMPLE 1

Diagnosis of Breast Cancer

Figure 1:
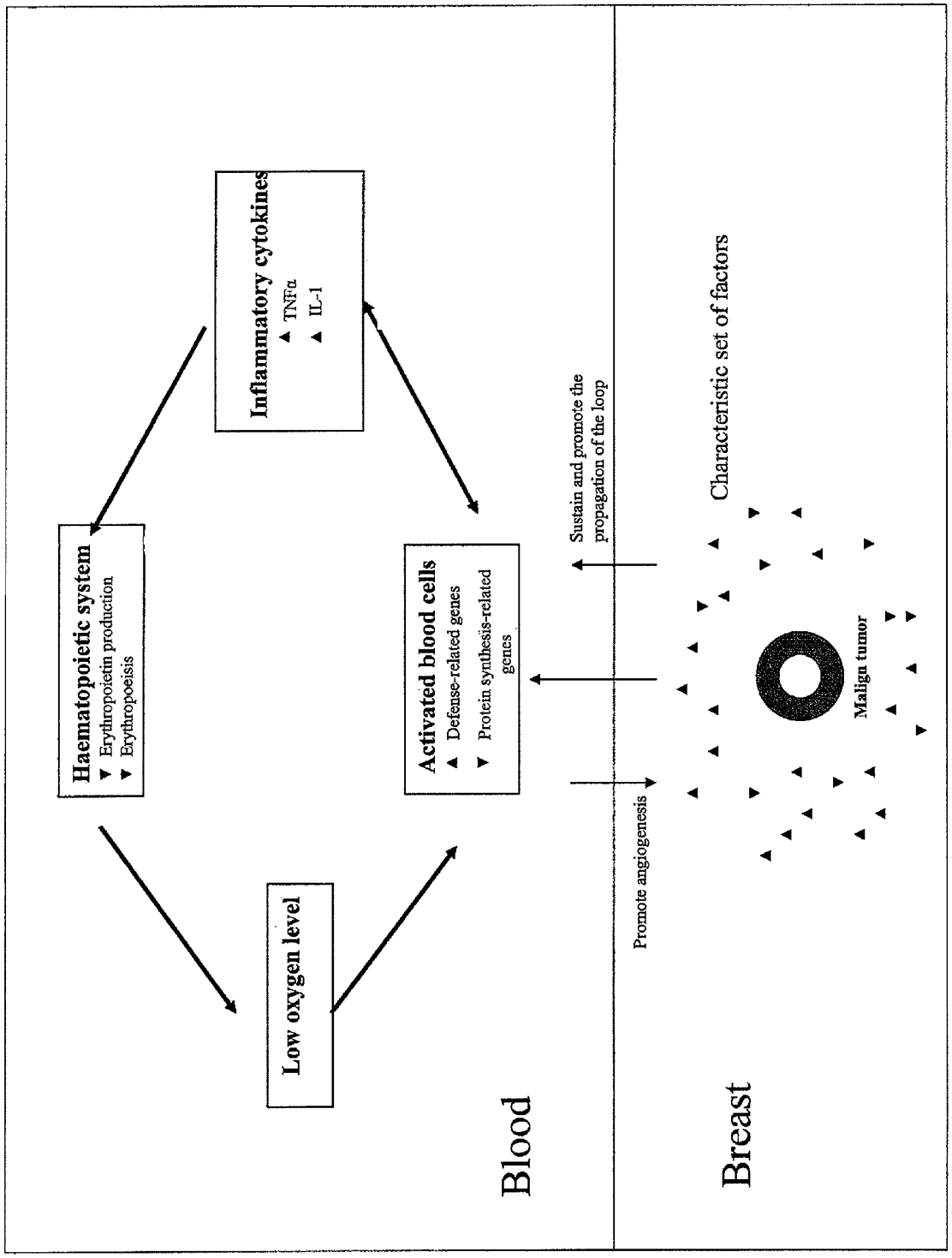
FIG. 1 shows the possible interplay of various factors responsible for changes in expression in an individual with breast cancer.

Methods
Blood Samples

Blood samples were collected from donors with their informed consent under an approval from Regional Ethical Committee of Norway. All donors were treated anonymously during analysis. Blood was drawn from females with a suspect initial mammogram, which included both females with breast cancer and females with abnormal mammograms, prior to any knowledge of whether the abnormality observed during first screening was benign or malignant. In all cases, the blood samples were drawn between 8 a.m. and 4 p.m. From each female, 10 ml blood was drawn by skilled personnel either in vacutainer tubes containing EDTA as anticoagulant (Becton Dickinson, Baltimore, USA) or directly in PAXgene™ tubes (PreAnalytiX, Hombrechtikon, Switzerland). Blood collected in EDTA tubes was immediately stored at −80° C., while PAX tubes were left overnight and then stored at −80° C. until used.

Preparation of cDNA Arrays 1435 cDNA clones were randomly picked from a plasmid library constructed from whole blood of 550 healthy individuals (Clontech, Palo Alto, USA). About 20% of the randomly picked clones were redundant. For amplification of inserts, bacterial clones were grown in microtiter plates containing 150 µl LB with 50 µg/ml carbenicillin, and incubated overnight with agitation at 37° C. To lyse the cells, 5 µl of each culture were diluted with 50 µl H$_2$O and incubated for 12 min. at 95° C. Of this mixture, 2 µl were subjected to a PCR reaction using 40 µpmol of 5'- and 3'-sequencing primer in the presence of 1.5 mM MgCl$_2$. PCR reactions were performed with the following cycling protocol: 4 min. at 95° C., followed by 25 cycles of 1 min. at 94° C., 1 min. at 60° C. and 3 min. at 72° C. either in a RoboCycler® Temperature Cycler (Stratagene, La Jolla, USA) or DNA Engine Dyad Peltier Thermal Cycler (MJ Research Inc., Waltham, USA). The amplified products were denatured with NaOH (0.2 M, final concentration) for 30 min and spotted onto Hybond-N$^+$ membranes (Amersham Phamiacia Biotech, Little Chalfont, UK), using a MicroGrid II workstation according to the manufacturer's instructions (BioRobotics Ltd, Cambridge England). The immobilized cDNAs were fixed using a UV cross-linker (Hoefer Scientific Instruments, San Francisco, USA).

In addition to the 1435 cDNAs, the printed arrays also contained controls for assessing background level, consistency and sensitivity of the assay. These were spotted at multiple positions and included controls such as PCR mix (without any insert); controls of SpotReport™ 10 array validation system (Stratagene, La Jolla, USA) and cDNAs corresponding to constitutively expressed genes such as β-actin, γ-actin, GAPDH, HOD and cyclophilin.

RNA Extraction, Probe Synthesis and Hybridization

Blood collected in EDTA tubes was thawed at 37° C. and transferred to PAX tubes, and total RNA was purified according to the supplier's instructions (PreAnalytiX, Hombrechtikon, Switzerland). From blood collected directly in PAX tubes total RNA was extracted in the tubes as above without any transfer to new tubes. Contaminating DNA was removed from the isolated RNA by DNAase I treatment using DNA-free kit (Ambion, Inc. Austin, USA). RNA quality was determined visually by inspecting the integrity of 28S and 18S ribosomal bands following agarose gel electrophoresis. Only samples from which good quality RNA was extracted were used in this study. In our experience, blood collected in EDTA tubes often resulted in poor quality RNA, while that collected in PAX tubes almost always gave good quality RNA. The concentration and purity of extracted RNA was determined by measuring the absorbance at 260 nm and 280 nm. From the total RNA, mRNA was isolated using Dynabeads according to the supplier's instructions (Dynal AS, Oslo, Norway).

Labelling and hybridization experiments were performed in 16 batches. The number of samples assayed in each batch varied from six to nine. To minimize the noise due to batch-to-batch variation in printing, only the arrays manufactured during the same print run were used in each batch. When samples were assayed more than once (replicates), aliquots from the same mRNA pool were used for probe synthesis. For probe synthesis, aliquots of mRNA corresponding to 4-5 µg of total RNA were mixed together with oligodT$_{25NV}$ (0.5 µg/µl) and mRNA spikes of SpotReport™ 10 array validation system (10 pg; Spike 2, 1 pg), heated to 70° C., and then chilled on ice. Probes were prepared in 35 µl reaction mixes by reverse transcription in the presence of 50 µCi [α$^{33}$P] dATP, 3.5 µM dATP, 0.6 mM each of dCTP, dTTP, dGTP, 200 units of SuperScript reverse transcriptase (Invitrogen, LifeTechnologies) and 0.1 M DTT labelling for 1.5 hr at 42° C. Following synthesis, the enzyme was deactivated for 10 min. at 70° C. and mRNA removed by incubating the reaction mix for 20 min. at 37° C. in 4 units of Ribo H (Promega, Madison USA). Unincorporated nucleotides were removed using ProbeQuant G 50 Columns (Amersham Biosciences, Piscataway, USA).

The membranes were equilibrated in 4×SSC for 2 hr at room temperature and prehybridized overnight at 65° C. in 10 ml prehybridization solution (4×SSC, 0.1 M NaH$_2$PO$_4$, 1 mM EDTA, 8% dextran sulphate, 10×Denhardt's solution, 1% SDS). Freshly prepared probes were added to 5 ml of the same prehybridization solution, and hybridization continued overnight at 65° C. The membranes were washed at 65° C. with increasing stringency (2×30 min. each in 2×SSC, 0.1% SDS; 1×SSC, 0.1% SDS; 0.1×SSC, 0.1% SDS).

Quantification of Hybridization Signals

The hybridized membranes were exposed to Phospho-screen (super resolution) for two days and an image file generated using PhosphoImager (Cyclone, Packard, Meriden, USA). The identification and quantification of the hybridization signals, as well as subtraction of local background values was performed using Phoretix software (Non Linear Dynamics, UK). For background subtraction, the median of the line of pixels around each spot outline was subtracted from the intensity of the signals assessed in each spot.

Data Analysis

From the 1435 background-subtracted expression data, signals of 67 genes were removed from each membrane to exclude genes expressed with a high degree of variance. These included removal of 1.25% of the lowest and highest signals from each membrane. For normalization, the value of each spot was first divided by the mean of signals in each array followed by a cube root transformation of all the spots. The normalized data was then batch adjusted using a one-way analysis of variance (ANOVA).

The pre-processed data was then used to isolate the informative probes by:

a) building a crossvalidated PLSR model, where one unique sample (including all repetitions of the selected sample) was kept out per cross-validation segment.

b) selecting the set of significant genes for the model in step a) using the Jackknife criterion.

c) building a crossvalidated PLSR-DA model as in step a) using the gene selected in step b).

d) selecting again the set of most significant genes for the model in step c) using the Jackknife criterion.

Step b) resulted in 125 genes.

Step d) resulted in selection of 35 significant genes. Based on these genes a final classification model was constructed.

Figure 2:
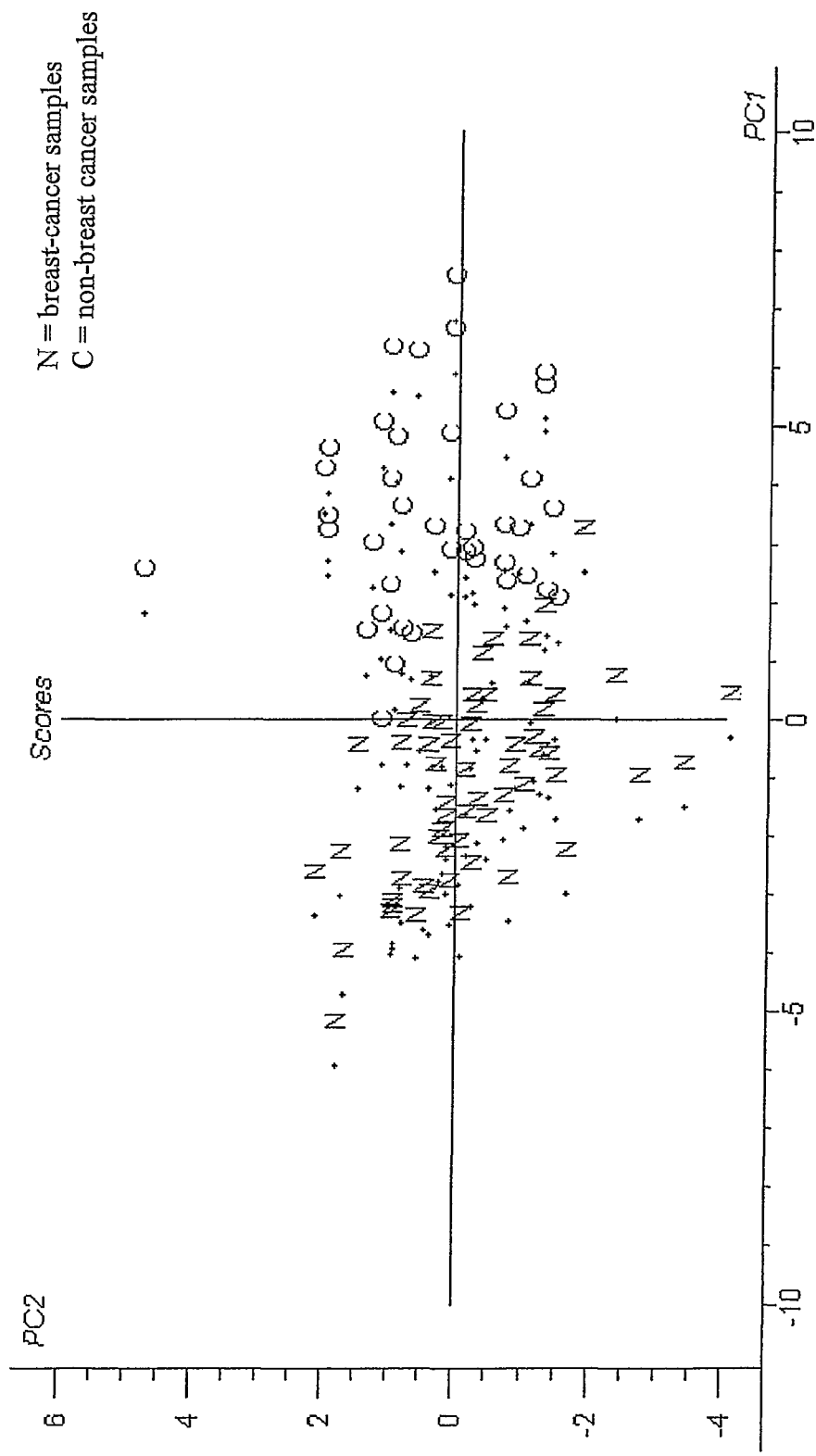
FIG. 2 shows the projection of 102 normal (including benign) and breast cancer samples onto a classification model generated by PLSR-DA using the data of 35 informative genes, in which PC is the principal components and N and C are normal and breast cancer samples, respectively.

The selected informative probes based on occurrence criterion were used to construct a classification model. The result of the classification model based on 35 probes is shown in FIG. 2 in which it is seen that the expression pattern of these genes was able to classify most women with breast cancer and women with no breast cancer into distinct groups. In this figure PC1 and PC2 indicate the two principal components statistically derived from the data which best define the systemic variability present in the data. This allows each sample, and the data from each of the informative probes to which the sample's labelled first strand cDNA was bound, to be represented on the classification model as a single point which is a projection of the sample onto the principal components—the score plot.

Figure 3:
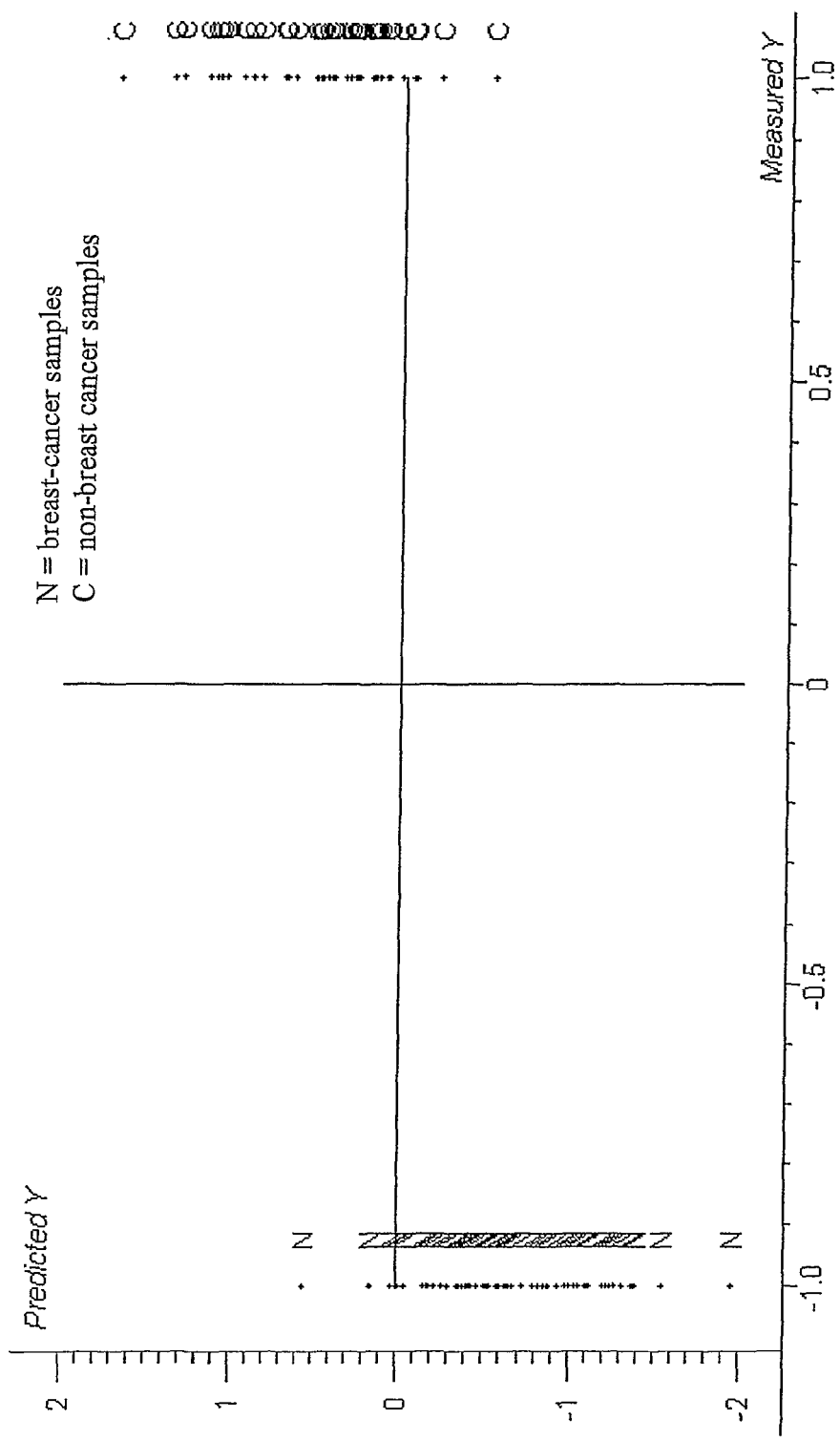
FIG. 3 shows a prediction plot based on 3 principal components using the data of 35 cDNAs.

FIG. 3 shows the prediction plot using the 35 significant genes. In the prediction plot shown, the cancer samples appear on the x axis at +1 and the non-cancer samples appear at −1. The y axis represents the predicted class membership. During prediction, if the prediction is correct, cancer samples should fall above zero and non-cancer samples should fall below zero. In each case almost all samples are correctly predicted. For cross-validation 102 experimental samples were divided into 60 cross-validation segments where each segment represented one unique sample and included its replicates if present.

Correct prediction of most breast cancer cells was achieved. 19 out of 22 cancer patients were correctly predicted as were 34/35 normal patients. Full details of the individuals examined and the accuracy of prediction are shown in Table 1. Table 2 provides details of the 35 informative genes, the genes in public databases to which they show sequence similarity and their putative biological function. Their sequences follow these examples.

Figure 4:
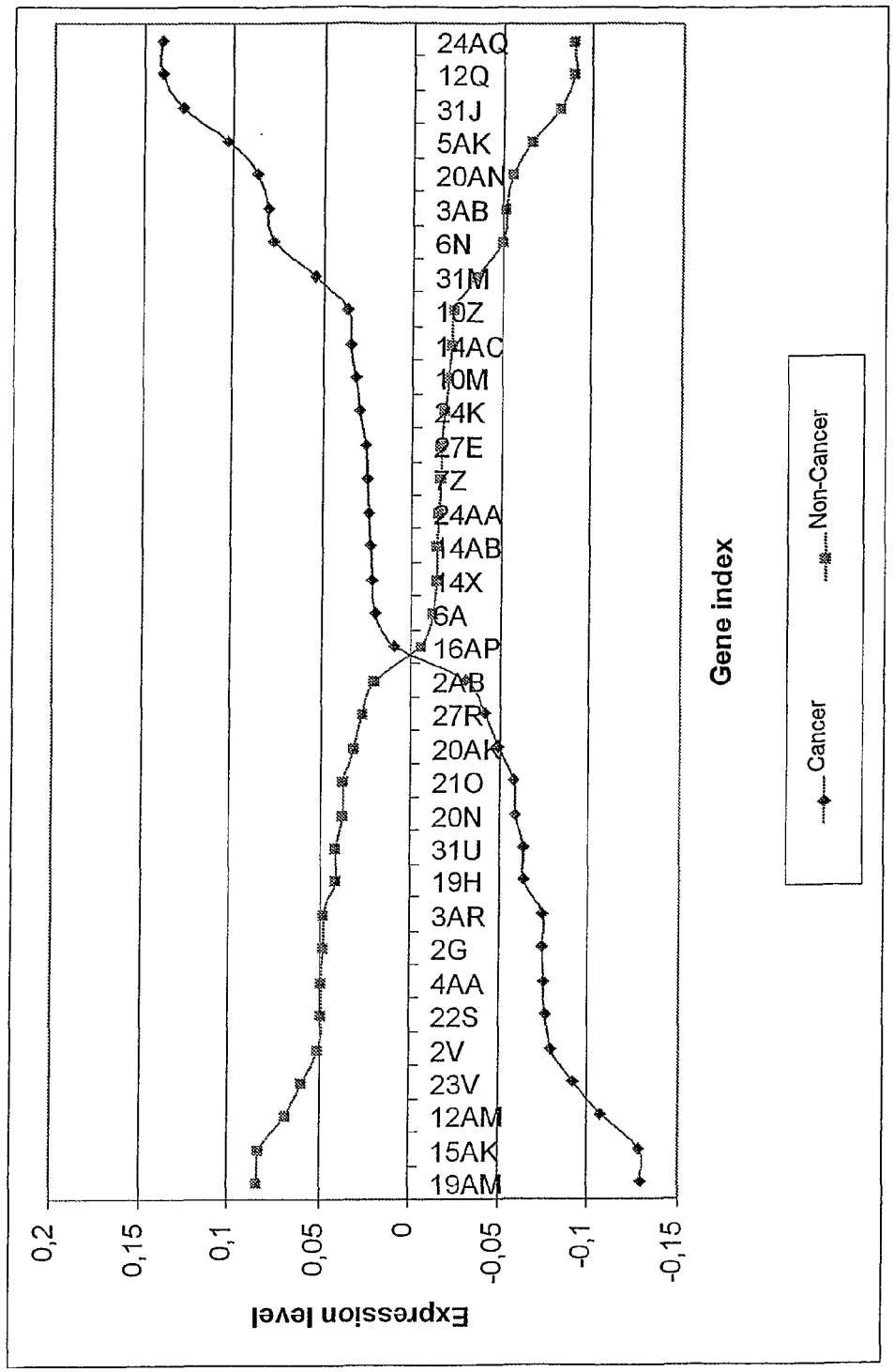
FIG. 4 shows the mean level of expression of the 35 genes used for prediction of breast cancer.

FIG. 4 shows the expression level of the 35 genes and it will be seen that some are over-expressed and others under-expressed relative to expression in normal patients.

EXAMPLE 2

Identification of Further Informative Probes and Use in Diagnosis of Breast Cancer Methods The methods of identification and analysis used were essentially as described in Example 1, except that instead of preparing a cDNA array, samples were analysed using a commercially available platform for large-scale gene expression analysis (Agilent 22K chip).

A larger number of samples comprising 122 in total (78 control and 44 with breast cancer) were analysed. The data was analysed using PLSR as described previously. The genes of interest were selected by a 10-fold cross validation approach. Thus, the data from 122 samples was divided into 10 sets, each set containing 12-13 samples. A calibration model was built on 9 sets leaving out one set. Significant genes were identified by the Jackknife technique on the built-in model. These steps were repeated for all 10 sets, in which each set was kept out at least once. Informative genes were then identified based on the frequency of occurrence criterion. 109 genes were found to informative in all 10 calibration models.

Results

The above described 109 genes and 3 further genes were used to predict the classification of 122 of the samples used. The results are shown in the table below.

| SAMPLE | Number | Correctly predicted | Incorrectly predicted | Error rate |
|---|---|---|---|---|
| Control | 78 | 67 | 11 | 0.14 |
| Breast cancer | 44 | 26 | 18 | 0.41 |

The 109 informative genes may be divided into three categories, namely those falling into families (i) and (ii) as described herein and other genes. Table 3 provides details of the informative probes whose corresponding genes fall into families (i) and (ii) and provides the number assigned by Agilent to that probe. Table 4 similarly provides details of the informative probes whose corresponding genes do not appear to fall within families (i) and (ii). Tables 5 and 6 provide details of the genes to which the probes in Tables 3 and 4, respectively, show sequence similarity, their putative biological function where known and the accession numbers for those genes.

APPENDIX A

Partial Least Squares Regression (PLSR)

Let a multivariate regression model be defined as:

$$Y = XB + F$$

where
X a N×P matrix with N predictor variables (genes);
Y (N×J) being the J predicted variables. In our case Y represents a matrix containing dummy variables;
B is a matrix of regression coefficients; and
F is a N×J matrix of residuals.

The structure of the PLSR model can be written as:

$$X = TP^T + E_A, \text{ and}$$

$$Y = TQ^T + F_A, \text{ where}$$

where
T (N×A) is a matrix of score vectors which are linear combinations of the x-variables;
P(P×A) is a matrix with the x-loading vectors $p_a$ as columns;
Q(J×A) is a matrix with the y-loading vectors $q_a$ as columns;
$E_A$(N×P) is the matrix for X after A factors; and
$F_A$(N×J) is the matrix for Y after A factors.

The criterion in PLSR is to maximize the explained covariance of [X,Y]. This is achieved by the loading weights vector $w_{a+1}$, which is the first eigenvector of $E_a^T F_a F_a^T E_a$ ($E_a$ and $F_a$ are the deflated X and Y after a factors or PLS components).

The regression coefficients are given by:

$$B = W(P^T W)^{-1} Q^T$$

A PLSR model with full rank, i.e. maximum number of components, is equivalent to the MLR solutions. Further details on PLSR can be found in Marteus & Naes, 1989, Multivariate Calibration, John Wiley & Sons, Inc., USA and Kowalski & Seasholtz, 1991, supra.

Nucleotide Sequences of 34/35 Genes Selected by Jackknife

```
Clone Ids and their sequences
I-30
                                      (SEQ ID NO: 113)
CTTTTCCTCCCGCTGTCCCCCACGGAGGGGACTGCTCTCCCCCGCTGCAT

CCTTTCTGTGAGGTACCTTACCCACCTCAGCACCTGAGAGGGTGAAATAG

AATTCTAACCTCGACATTCGGGAAGTGTTTTTGAGAAGTCTCGGTCGGTA

AGGGAAGTCTTCCAAGTCCGTGCAGCACTAACGTATTGGCACCTGCCTCC

TCTTCGGCCACCCCCCAGATGAGGCAGCTGTGACTGTGTCAAGGGAAGCC

ACGACTCTGACCATAGTCTTCTCTCAGCTTCCACTGCCGTCTCCACAGGA

AACCCAGAAGTTCTGTGAACAAGTCCATGCTGCCATCAAGGCATTTATTG

CAGTGTACTATTTGCTTCCAAAGGATCAGGCCCTGAGAACAATGACCTTA

TTTCCTACAACAGTGTCTGGGTTGCGTGCCAGCAGATGCCTCAGATACCA

AGAGATAACAAAGCTGCAGCTCTTTTGATGCTGACCAAGAATGTGGATTT

TGTGAAGGATGCACATGAAGAAATGGAGCAGGCTGTGGAAGAATGTGACC

CTTACTCTGGCCTCTTGAATGATACTGAGGAGAACAACTCTGACAACCAC

AATCATGAGGATGATGTGTTGGGGTTTCCCAGCAATCAGGACTTGTATTG

GTCAGAGGACGATCAAGAGCTCATAATCCCATGCCTTGCGCTGGTGAGAG

CATCCAAAGCCTGCCTGAAGAAAATTCGGATGTTAGTGGCAGAGAATGGG
```

-continued

AAGAAGGATCAGGTGGCACAGCTGGATGACATTGTGGATATTTCTGATGA

AATCAGCCCTAGTGTGGATGATTTGGCTCTGAGCATATATCCACCTATGT

GTCACCTGACCGTGCGAATCAATTCTGCGAAACTTGTATCTGTTTTAAAG

AAGGCACTTGAAATTACAAAAGCAAGTCATGTGACCCCTCAGCCAGAAGA

TAGTTGGATCCCTTTACTTATTAATGCCATTGATCATTGCATGAATAGAA

TCAAGGAGCTCACTCAGAGTGAACTTGAATTATGACTTTTCAGGCTCATT

TGTACTCTCTTCCCCTCTCATCGTCATGGTCAGGCTCTGATACCTGCTTT

TAAAATGGAGCTAGAATGCTTGCTGGATTGAAAGGGAGTGCCTATCTATA

TTTAGCAAGAGACACTATTACCAAAGATTGTTGGTTAGGCCAGATTGACA

CCTATTTATAAACCATATGCGTATATTTTTCTGTGCTATATATGAAAAAT

AATTGCATGATTTCTCATTCCTGAGTCATTTCTCAGAGATTCCTAGGAAA

GCTGCCTTATTCTCTTTTTGCAGTAAAGTATGTTGTTTTCATTGTAAAGA

TGTTGATGGTCTCAATAAAATGCTAACTTGCCAGTGAAAAAAAAAAAAAA

III-02
(SEQ ID NO: 114)
AGGATCTAAGACCAGCCTGGCAGCCACCAGATGGTGATTCTAGTCCTGGC

TCAGTCAGTAATAGGTCACTGACCCCAGAGAAATCAATTCAGCCTCCCCA

GGTCCTTGGATTTCTTTCTGTGAAAATGAAAGCATAGGTAGGAATTTCCC

ATGGAACAGCTAGCAGAGGAGAAATATTAAAAGTCAGGAGACTCATGCTA

TAGTTTTCATACTTCATTACAACAATGTTGTTTAGGACAAGTGAGTTAAC

CTGTTAGCTTCCTCTATATAAAATGGAAAGTCATTAAAAACCTACATAGC

AGGGTTCTTGTGAAGATCAAGTGATAATGTAGGAAGCATGTACAAATGTC

ACATTCTGCCGTCACGTAATGGTCCTCACAGCTTGAGGTAGCATTTAGCA

TGTGTCATGATTTAGTACAAGGGTTGGCAAACTGTTGCTCTTGGATTAAG

TCTGGCTCATTGCCTGTTTTTCAAAGAAAAAAATTGTATATGTGTGTATA

TATGTTATATATAGGTACACACACATATGTGCTATATATAGCATATATAC

ACACATAATATATAAACATGTACATATATAGCATTATATATATACGTGTA

TAATATCTCCAGTCCTCATGACCAGCCATGCTTGTTCATTTACATTTGCA

TACTCTATGATTGCTTTCATGCAACAATGGCAGAGTTGAGTGATTGTTTT

GCAACAGAGACTGTATGGCCCACTAAACCTAAAATATTTAGTCTCTGACC

CTGAAATGTAAGATTGATAGCCCAGGACCAGGCGTGGTGGCTCACACTTG

TAATCCTAGCACTTTGGCAGGCCAAGGAGGGTGGATCACCTGAGGTCAGG

AGTTAAAGACCAGCCTGGCCAACATGGTGAAACCCTGACTCTACTAAAAA

TACAGAAATTAGCTGGGCGTGGTAATGGGTGCCTGCAATCCAAGCTACTC

TGGAGGCTGAGGCAGGAGAATCACTTGAACCCAGGAGGCAGAAGTTACAG

TGAGCTGAGATGGTGCCACTGCACTCCAGCCTGGACGACAGAGTGAGACT

CCATCTCAAAAA

III-27
(SEQ ID NO: 115)
CCATTCTCCTGCCTCAGCCTCTCAAGTAGCTGGGACTACAGGCGCCCACA

ACCACGCCCGGCTAATGTTTTGGTATTTTTCGTAGAGACGGGGTTTCAC

CTTGTTAGCCAGGATGGTCTTGATCTCCTGACCTCGTGATCTGCCTGCCT

CGGCCTCCCAAAGTGTTGGGATTACAGGCACATTTTTCACAATTTTTTAA

CACTTAAGAATGACTTAACTGAATCATGCCTTTAGAAGAAACTTTCTGTT

TAAAAAAAAAAAAAAA

III-60
(SEQ ID NO: 116)
CTGCCGCCGCCCCCAGCTCCCCCGCCTCGGGGAGGGCACCAGGTCACTGC

AGCCAGAGGGGTCCAGAAGAGAGAGGAGGCACTGCCTCCACTACAGCAAC

TGCACCCACGATGCAGAGCATCAAGTGCGTGGTGGTGGGTGATGGGGCTG

TGGGCAAGACGTGCCTGCTCATCTGCTACACAACTAACGCTTTCCCCAAA

GAGTACATCCCCACCGTGTTCGACAATTACAGCGCGCAGAGCGCAGTTGA

CGGGCGCACAGTGAACCTGAACCTGTGGGACACTGCGGGCCAGGAGGAGT

ATGACCGCCTCCGTACACTCTCCTACCCTCAGACCAACGTTTTCGTCATC

TGTTTCTCCATTGCCAGTCCGCCGTCCTATGAGAACGTGCGGCACAAGTG

GCATCCAGAGGTGTGCCACCACTGCCCTGATGTGCCCATCCTGCTGGTGG

GCACCAAGAAGGACCTGAGAGCCCAGCCTGACACCCTACGGCGCCTCAAG

GAGCAGGGCCAGGCGCCCATCACACCGCAGCAGGGCCAGGCACTGGCCAA

GCAGATCCACGCTGTGCGCTACCTCGAATGCTCAGCCCTGCAACAGGATG

GTGTCAAGGAAGTGTTCGCCGAGGCTGTCCGGGCTGTGCTCAACCCCACG

CCGATCAAGCGTGGGCGGTCCTGCATCCTCTTGTGACCCTGGCACTTGGC

TTGGAGGCTGCCCCTGCCCTCCCCCCACCAGTTGTGCCTTGGTGCCTTGT

CCGCCTCAGCTGTGCCTTAAGGACTAATTCTGGCACCCCTTTCCAGGGGG

TTCCCTGAATGCCTTTTTCTCTGAGTGCCTTTTTCTCCTTAAGGAGGCCT

GCAGAGAAAGGGCTTTGGGCTCTGCCCCCCTCTGCTTGGGAACACTGGGT

ATTCTCATGAGCTCATCCAAGCCAAGGTTGGACCCCTCCCCAAGAGGCCA

ACCCAGTGCCCCCTCCCATTTTCCGTACTGACCAGTTCATCCAGCTTTCC

ACACAGTTGTTGCTGCCTATTGTGGTGCCGCCTCAGGTTAGGGGCTCTCA

GCCATCTCTAACCTCTGCCCTCGCTGCTCTTGGAATTGCGCCCCCAAGAT

GCTCTCTCCCTTCTCCAATGAGGGAGCCACAGAATCCTGAGAGTGAATGT

GCCCTAACCTGCTCCTCTGTGCCTAGGCCTTACGCATTTGCTGACTGACT

CAGCCCCCATGCTTCTGGGGACCTTTCCTACCCCCATCAGCATCAATAAA

ACCTCCTGTCTCCAGTGA

IV-26
(SEQ ID NO: 117)
CAGCCCTCCGTCACCTCTTCACCGCACCCTCGGACTGCCCCAAGGCCCCC

GCCGCCGCTCCAGCGCCGCGCAGCCACCGCCGCCGCCGCCGCCTCTCCTT

AGTCGCCGCCATGACGACCGCGTCCACCTCGCAGGTGCGCCAGAACTACC

ACCAGGACTCAGAGGCCGCCATCAACCGCCAGATCAACCTGGAGCTCTAC

GCCTCCTACGTTTACCTGTCCATGTCTTACTACTTTGACCGCGATGATGT

GGCTTTGAAGAACTTTGCCAAATACTTTCTTCACCAATCTCATGAGGAGA

GGGAACATGCTGAGAAACTGATGAAGCTGCAGAACCAACGAGGTGGCCGA

ATCTTCCTTCAGGATATCAAGAAACCAGACTGTGATGACTGGGAGAGCGG

GCTGAATGCAATGGAGTGTGCATTACATTTGGAAAAAAATGTGAATCAGT

CACTACTGGAACTGCACAAACTGGCCACTGACAAAAATGACCCCCATTTG

-continued

TGTGACTTCATTGAGACACATTACCTGAATGAGCAGGTGAAAGCCATCAA

AGAATTGGGTGACCACGTGACCAACTTGCGCAAGATGGGAGCGCCCGAAT

CTGGCTTGGCGGAATATCTCTTTGACAAGCACACCCTGGGAGACAGTGAT

AATGAAAGCTAAGCCTCGGGCTAATTTCCCCATAGCCGTGGGGTGACTTC

CCTGGTCACCAAGGCAGTGCATGCATGTTGGGGTTTCCTTTACCTTTTCT

ATAAGTTGTACCAAAACATCCACTTAAGTTCTTTGATTTGTACCATTCCT

TCAAATAAAGAAATTTGGTACCCAAAAAAAA

IV-41

(SEQ ID NO: 118)
GCCATTTCTAAGACCTACAGCTACCTGACCCCCGACCTCTGGAAGGAGAC

TGTATTCACCAAGTCTCCCTATCAGGAGTTCACTGACCACCTCGTCAAGA

CCCACACCAGAGTCTCCGTGCAGCGGACTCAGGCTCCAGCTGTGGCTACA

ACATAGGGTTTTTATACAAGAAAAATAAAGTGAATTAAGCGTGAAAA

IV-51

(SEQ ID NO: 119)
ATTTCTGTGGATACAGTGCCCACCGCCCTCCTCCACTTGGAAACGGTATC

CTCCCTGCCCATCCGTCTGTCTGTCGCCCTTCTCCCGGCCCTCACTAAGC

CCCGGCACTTCTAGTGGTCTCACCTGGAGGCAAGAGGGAGGGGACAGAGG

CCCTGCCACGTCCCGCTGCCTCCTGCTCTCTGGAGGTACTGAGACAGGGT

GCTGATGGGAAGGAGGGGAGCCTTTGGGGGGCCACCCGGGGCCTGGACCT

ATGCAGGGAGGCCACGTCCCACCCCACCTCTTGTTTCTGGGTCCCTGCTC

CCCTTTGGGGGTGTGTGTGTGTGTTTTAATTTTCTTTATGGAAAAATTGA

CAAAAAAAAATAGAGAGAGAGGTATTTAACTGCAATAAACTGGCCCCATG

TGGCCCCCGCCTTGTCAAAAAAAAA

V-09

(SEQ ID NO: 120)
TGGATTCCCGTCGTAACTTAAAGGGAAACTTTCACAATGTCCGGAGCCCT

TGATGTCCTGCAAATGAAGGAGGAGGATGTCCTTAAGTTCCTTGCAGCAG

GAACCCACTTAGGTGGCACCAATCTTGACTTCCAGATGGAACAGTACATC

TATAAAAAAGGAAAAGTGATGGCATCTATATCATAAATCTCAAGAGGACC

TGGGAGAAGCTTCTGCTGGCAGCTCGTGCAATTGTTGCCATTGAAAACCC

TGCTGATGTCAGTGTTATATCCTCCAGGAATACTGGCCAGAGGGCTGTGC

TGAAGTTTGCTGCTGCCACTGGAGCCACTCCAATTGCTGGCCGCTTCACT

CCTGGAACCTTCACTAACCAGATCCAGGCAGCCTTCCGGGAGCCACGGCT

TCTTGTGGTTACTGACCCCAGGGCTGACCACCAGCCTCTCACGGAGGCAT

CTTATGTTAACCTACCTACCATTGCGCTGTGTAACACAGATTCTCCTCTG

CGCTATGTGGACATTGCCATCCCATGCAACAACAAGGGAGCTCACTCAGT

GGGTTTAATGTGGTGGATGCTGGCTCGGGAAGTTCTGCGCATGCGTGGCA

CCATTTCCCGTGAACACCCATGGGAGGTCATGCCTGATCTGTACTTCTAC

AGAGATCCTGAAGAGATTGAAAAGAAGAGCAGGCTGCTGCTGAGAAGGC

AGTGACCAAGGAGGAATTTCAGGGTGAATGGACTGCTCCCGCTCCTGAGT

TCACTGCTACTCAGCCTGAGGTTGCAGACTGGTCTGAAGGTGTACAGGTG

CCCTCTGTGCCTATTCAGCAATTCCCTACTGAAGACTGGAGCGCTCAGCC

TGCCACGGAAGACTGGTCTGCAGCTCCCACTGCTCAGGCCACTGAATGGG

TAGGAGCAACCACTGACTGGTCTTAAGCTGTTCTTGCATAGGCTCTTAAG

CAGCATGGAAAAATGGTTGATGGAAAATAAACATCAGTTTCT

V-38

(SEQ ID NO: 121)
GTTTAAATTTGACAAACTAAAGCTAATTACTGCTATAAGAGTAATAACTG

CTCATTTTCCATAACTCATTCTTAAAGTTTTAGTAATGTAAAAGTTATTT

TTTTGCAGTAAGTTATAATGATAGAAGCTTACATGTTTTTTCATGCCTCA

TCTGTTTCCCCTTAAAACTATAATTATCAGTAAAGTCCTGTGGTATTTTT

CAATTTGTAAGAAACTAGGCTATATATACATTGGGAAAAACAGCCTTCAT

TTGTCAATGCACTAGTGTTCCAAAGGTTTCTGGTAATTGTGTGCTATTGC

TTTTTGTTGACTTGCAAAAAAAAAAAAAAAAAATTACTATGACTTGTGG

TAGCCCTGCAACCTTCGGAAGTGCTTAGCCCAGTCTGACCATACATTTAT

ATTTAGAATGCTTAGGTAAATAAATAATATGCCTAAACCCAATGCTATAA

GATACTATATAATATCTCATAATTTTAAAAATCACTGTTTTGTATAATAA

TAAAACAAGGCAGGCAAGCTGTTCTACAATGACTGTTGGTAAGGGTGCTG

AGGAAGAAAAACAAACAATCTTGATTCAGGGATAGTGAATAGACAAAAAA

TGTCCTAATCAATGAAGCTGTGTGATGATTCTGATTGACAGAGAGTGCTG

CCACAAGATTCTTAGGCTACACTCAAATCAGCAGAAAAAGTGCTACAATA

AATTAGAAGTGACTATTACAGGTGCAGATGAGGGTTGGTAGTACCTGTTT

GCCATTTCTCTTCTAATCTTATATTTTCTGACCCTCCTACTGTAAGTCGC

GCGGAGGCGGAGGCTTGGGTGCGTTCAAGATTCAACTTCACCCGTAACCC

ACCGCCATGGCCGAGGAAGGCATTGCTGCTGGAGGTGTAATGGACGTTAA

TACTGCTTTACAAGAGGTTCTGAAGACTGCCCTCATCCACGATGGCCTAG

CACGTGGAATTCGCGAAGCTGCCAAAGCCTTAGACAAGCGCCAAGCCCAT

CTTTGTGTGCTTGCATCCAACTGTGATGAGCCTATGTATGTCAAGTTGGT

GGAGGCCCTTTGTGCTGAACACCAAATCAACCTAATTAAGGTTGATGACA

ACAAGAAACTAGGAGAATGGGTAGGCCTTTGTAAAATTGACAGAGAGGGG

AAACCCCGTAAAGTGGTTGGTTGCAGTTGTGTAGTAGTTAAGGACTATGG

CAAGGAGTCTCAGGCCAAGGATGTCATTGAAGAGTATTTCAAATGCAAGA

AATGAAGAAATAAATCTTTGGCTCACAAA

VI-44

(SEQ ID NO: 122)
GAGAATGGCTTGAACCCAGTAGGCAGAGGTTGTAGTGAGCCGAGATTGGG

CCACTGCACTTTAGCCTGGGTGACAGAGTGAGACTCTGTCTCAAAAAAAA

AAAAAAAAATTTAAATAAAATAAAAAACCTTTACTTATTTTTAAATTGG

GTTGTCTTTTTGGTATTGAGTTGTTAAAGTTCTTTATATATTTTAGGTAC

AAATCCCTTATGAGATACGTGATTTGAAAATATTTTCTCCCATTCTGTGG

GTTGCTTTTTCACTTTCTTGGTTGTATCCTTTGAAGCACAGAAGTTTTAA

ATTTTGATGAAGTCCAGTTTATTTATTTTTTTGCTGTTGTTTCTGCTCAT

ACTTTTGAGGTCATGTCTGAGAAACCATTGTCAAATCCAAGGTCGTGATG

ACTTACCCCTGTGTTTTCTTCTAAGAGTTTTAAAGGCATCTGAAGCTTAA

TGTGCACTAGATGGATTCTAAATATCATCTCATCCAAAACCTGCTATATA

-continued

TACTACCTTCCTCATCTCAGTTGAAGGCAAGTCCATTGTTTCAATTGCCT

GGGCAAAAAATATTCTAAATAATTCATAATTTTTCCTCAACTCCACATCT

ATTGGTAAATCCTGTGGGTTCTCCTTTTAAAACATATCCAAAATAGAATC

ATTTCTCACTATCATTCCACTGCAGGCACCAAGTCTCAATAGTCTCCTAG

CAGATAATCATGTCTACATTTATTCTCAATGTAGCAGCTAGAGAGCTTTT

TTG

VI-49

(SEQ ID NO: 123)
GCGGTCGTAAGGGCTGAGGATTTTTGGTCCGCACGCTCCTGCTCCTGACT

CACCGCTGTTCGCTCTCGCCGAGGAACAAGTCGGTCAGGAAGCCCGCGCG

CAACAGCCATGGCTTTTAAGGATACCGGAAAAACACCCGTGGGAGCCGGAG

GTGGCAATTCACCGAATTCGAATCACCCTAACAAGCCGCAACGTAAAATC

CTTGGAAAAGGTGTGTGCTGACTTGATAAGAGGCGCAAAAGAAAAGAATC

TCAAAGTGAAAGGACCAGTTCGAATGCCTACCAAGACTTTGAGAATCACT

ACAAGAAAAACTCCTTGTGGTGAAGGTTCTAAGACGTGGGATCGTTTCCA

GATGAGAATTCACAAGCGACTCATTGACTTGCACAGTCCTTCTGAGATTG

TTAAGCAGATTACTTCCATCAGTATTGAGCCAGGAGTTGAGGTGGAAGTC

ACCATTGCAGATGCTTAAGTCAACTATTTTAATAAATTGATGACCAGTTG

TTAAAAAAAAAAAAAA

VI-52

(SEQ ID NO: 124)
GAAAGGGNTNGCNCCCAANGGGCAGAGGTTGGGCTGATGCCGATATTGGG

CCNCTGCNCTNCANACCTGGGTGACATGAATGAAACTCTGTCTCACATAA

AAACCCAAAAAANCTAAATGAAATAAAAGACCTTTGCTTATTNCTAANTT

GGGTACGC

VII-15

(SEQ ID NO: 125)
CCCATCCCCTCGACCGCTCGCGTCGCATTTGGCCGCCTCCCTACCGCTCC

AAGCCCAGCCCTCAGCCATGGCATGCCCCCTGGATCAGGCCATTGGCCTC

CTCGTGGCCATCTTCCACAAGTACTCCGGCAGGGAGGGTGACAAGCACAC

CCTGAGCAAGAAGGAGCTGAAGGAGCTGATCCAGAAGGAGCTCACCATTG

GCTCGAAGCTGCAGGATGCTGAAATTGCAAGGCTGATGGAAGACTTGGAC

CGGAACAAGGACCAGGAGGTGAACTTCCAGGAGTATGTCACCTTCCTGGG

GGCCTTGGCTTTGAT

VII-32

(SEQ ID NO: 126)
AATTAGAGAGGTGAGGATCTGGTATTTCCTGGACTAAATTCCCCTTGGGG

AAGACGAAGGGATGCTGCAGTTCCAAAAGAGAAGGACTCTTCCAGAGTCA

TCTACCTGAGTCCCAAAGCTCCCTGTCCTGAAAGCCACAGACAATATGGT

CCCAAATGACTGACTGCACCTTCTGTGCCTCAGCCGTTYTTGACATCAAG

AATCTTCTGTTCCACATCCACACAGCCAATACAATTAGTCAAACCACTGT

TATTAACAGATGTAGCAACATGAGAAACGCTTATGTTACAGGTTACATGA

GAGCAATCATGTAAGTCTATATGACTTCAGAAATGTTAAAATAGACTAAC

CTCTAACAACAAATTAAAAGTGATTGTTTCAAGGTGATGCAATTATTGAT

GACCTATTTTATTTTTCTATAATGATCATATATTACCTTTGTAATAAAAC

ATTATAACCAAAAAAAAAAAAAAAAAAAAAAAAAAAAAAAAA

VII-48

(SEQ ID NO: 127)
CTTAAGTATGCCCTGACAGGAGATGAAGTAAAGAAGATTTGCATGCAGCG

GTTCATTAAAATCGATGGCAAGGTCCGAACTGATATAACCTACCCTGCTG

GATTCATGGATGTCATCAGCATTGACAAGACGGGAGAGAATTTCCGTCTG

ATCTATGACACCAAGGGTCGCTTTGCTGTACATCGTATTACACCTGAGGA

GGCCAAGTACAAGTTGTGCAAAGTGAGAAAGATCTTTGTGGGCACAAAAG

GAATCCCTCATCTGGTGACTCATGATGCCCGCACCATCCGCTACCCCGAT

CCCCTCATCAAGGTGAATGATACCATTCAGATTGATTTAGAGACTGGCAA

GATTACTGATTTCATCAAGTTCGACACTGGTAACCTGTGTATGGTGACTG

GAGGTGCTAACCTAGGAAGAATTGGTGTGATCACCAACAGAGAGAGGCAC

CCTGGATCTTTTGACGTGGTTCACGTGAAAGATGCCAATGGCAACAGCTT

TGCCACTCGACTTTCCAACATTTTTGTTATTGGCAAGGGCAACAAACCAT

GGATTTCTCTTCCCCGAGGAAAGGGTATCCGCCTCACCATTGCTGAAGAG

AGAGACAAAAGACTGGCGGCCAAACAGAGCAGTGGGTGAAATGGGTCCCT

GGGTGACATGTCAGATCTTTGTACGTAATTAAAAATATTGTGGCAGGATT

AATAGCC

VII-76

(SEQ ID NO: 128)
AGACACACGAGCATATTTCACCTCCGCTACCATAATCATCGCTATCCCCA

CCGGCGTCAAAGTATTTAGCTGACTCGCCACACTCCACGGAAGCAATATG

AAATGATCTGCTGCAGTGCTCTGAGCCCTAGGATTCATCTTTCTTTTCAC

CGTAGGTGGCCTGACTGGCATTGTATTAGCAAACTCATCACTAGACATCG

TACTACACGACACGTACTACGTTGTAGCCCACTTCCACTATGTCCTATCA

ATAGGAGCTGTATTTGCCATCATAGGAGGCTTCATTCACTGATTTCCCCT

ATTCTCAGGCTACACCCTAGACCAAACCTACGCCAAAATCCATTTCACTA

TCATATTCATCGGCGTAAATCTAACTTTCTTCCCACAACACTTTCTCGGC

CTATCCGGAATGCCCCGACGTTACTCGGACTACCCCGATGCATACACCAC

ATGAAACATCCTATCATCTGTAGGCTCATTCATTTCTCTAACAGCAGTAA

TATTAATAATTTTCATGATTTGAGAAGCCTTCGCTTCGAAGCGAAAAGTC

CTAATAGTAGAAGAACCCTCCATAAACCTGGAGTGACTATATGGATGCCC

CCCACCCTACCACACATTCGAAGAACCCGTATACAT

IX-24

(SEQ ID NO: 129)
AGAGTGCAAGACGATGACTTGCAAAATGTCGCAGCTGGAACGCAACATAG

AGACCATCATCAACACCTTCCACCAATACTCTGTGAAGCTGGGGCACCCA

GACACCCTGAACCAGGGGAATTCAAAGAGCTGGTGCGAAAAGATCTGCA

AAATTTTCTCAAGAAGGAGAATAAGAATGAAAAGGTCATAGAACACATCA

TGGAGGACCTGGACACAAATGCAGACAAGCAGCTGAGCTTCGAGGAGTTC

ATCATGCTGATGGCGAGGCTAACCTGGGCCTCCCACGAGAAGATGCACGA

GGGTGACGAGGGCCCTGGCCACCACCATAAGCCAGGCCTCGGGGAGGGCA

CCCCCTAAGACCACAGTGGCCAAGATCACAGTGGCCACGGCCACGGCCAC

-continued

AGTCATGGTGGCCACGGCCACAGCCACTAATCAGGAGGCCAGGCCACCCT
GCCTCTACCCAACCAGGGCCCCGGGGCCTGTTATGTCAAACTGTCTTGGC
TGTGGGGCTAGGGGCTGGGGCCAAATAAAGTCTCTTCCTCCAAAAAAAA

IX-39
(SEQ ID NO: 130)
CTTGGCTCCTGTGGAGGCCTGCTGGGAACGGGACTTCTAAAAGGAACTAT
GTCTGGAAGGCTGTGGTCCAAGGCCATTTTTGCTGGCTATAAGCGGGTC
TCCGGAACCAAAGGGAGCACACAGCTCTTCTTAAAATTGAGTGTTTACGC
CCAGATGAAACAGAATTCTATTTGGGCAAGAGATGCGCTTATGTATATAA
AGCAAAGAACAACACAGTCACTCCTGGCGGCAAACCAAACAAAACCAGAG
TCATCTGGGGGAAAAGTAACTCGGGCCCATGGAAACAGTGGCATGGTTCG
TGCCAAATTCCGAAGCAATCTTCCTGCTAAGGCCATTGGACACAGAATCC
GAGTGATGCTGTACCCCTCAAGGATTTAAACTAACGAAAAATCAATAAAT
AAATGTGGATTTGTGCTCTTGTA

IX-46
(SEQ ID NO: 131)
ACGCGAGATGGCAGTGCAAATATCCAAGAAGAGGAAGTTTGTCGCTGATG
GCATCTTCAAAGCTGAACTGAATGAGTTTCTTACTCGGGAGCTGGCTGAA
GATGGCTACTCTGGAGTTGAGGTGCGAGTTACACCAACCAGGACAGAAAT
CATTATCTTAGCCACCAGAACACAGAATGTTCTTGGTGAGAAGGCCGGCG
GATTCGGGAACTGACTGCTGTAGTTCAGAAGAGGTTTGGCTTTCCAGAGG
GCAGTGTAGAGCTTTATGCTGAAAAGGTGGCCACTAGAGGTCTGTGTGCC
ATTGCCCAGGCAGAGTCTCTGCGTTACAAACTCCTAGGAGGGCTTGCTGT
GCGGAGGGCCTGCTATGGTGTGCTGCGGTTCATCATGGAGAGTGGGGCCA
AAGGCTGCGAGGTTGTGGTGTCTGGGAAACTCCGAGGACAGAGGGCTAAA
TCCATGAAGTTTGTGGATGGCCTGATGATCCACAGCGGAGACCCTGTTAA
CTACTACGTTGACACTGCTGTGCGCCACGTGTTGCTCAGACAGGGTGTGC
TGGGCATCAAGGTGAAGATCATGCTGCCCTGGGACCCAACTGGTAAGATT
GGCCCTAAGAAGCCCCTGCCTGACCACGTGAGCATTGTGCCCAAAGATG
AGATACTGCCCACCACCCCATCTCAGAACAGGGTGGGAAGCCAGAGCCG
CCTGCCATGCCCCAGCCAGTCCCCACAGCATAACAGGGTCTCCTTGGCAG
CTGTATTCTGGAGTCTGGATGTTGCTCTCTAAAGACCTTTAATAAAATTT
TGT

IX-50
(SEQ ID NO: 132)
GTCCATCCTGCAGGCCACAAGCTCTGGATGAGGAACTTGAGGCAAGTCAC
CAGCCCCTGATCATTTCGCCTAAAAGAGCAAGGACTAGAGTTCCTGACCT
CCAGGCCAGTCCCTGATCCCTGACCTAATGTTATCGCGGAATGATGATAT
ATGTATCTACGGGGGCCTGGGGCTGGGCGGGCTCCTGCTTCTGGCAGTGG
TCCTTCTGTCCGCCTGCCTGTGTTGGCTGCATCGAAGAGTAAAGAGGCTG
GAGAGGAGCTGGGCCCAGGGCTCCTCAGAGCAGGAACTCCACTATGCATC
TCTGCAGAGGCTGCCAGTGCCCAGCAGTGAGGGACCTGACCTCAGGGCA
GAGACAAGAGAGGCACCAAGGAGGATCCAAGAGCTGACTATGCCTGCATT
GCTGAGAACAAACCCACCTGAGCACCCCAGACACCTTCCTCAACCCAGGC
GGGTGGACAGGGTCCCCCTGTGGTCCAGCCAGTAAAAACCATGGTCCCCC
CACTTCTGTGTCTCAGTCCTCTCAGTCCATCTCGAGCCTCCGTTCAAAAT
GATCATCATCAAAACTTATGTGGCTTTTTGACCTTTGAATAGGGAATTTT
TTAAATTTTTTAAAAATTAAAATAAAAAAACACATGGCTCACCCTTCCA
CCCAAAAAAAAA

X-77
(SEQ ID NO: 133)
CCTCCCGGGCTCTTAAGCCCCTCTCTTTCTCTAACAGAAAAAGCGGATGG
TGGTTCCTGCTGCCCTCAAGGTCGTGCGTCTGAAGCCTACAAGAAAGTTT
GCCTATCTGGGCGCCTGGCTCACGAGGTTGGCTGGAAGTACCAGGCAGT
GACAGCCACCCTGGAGGAGAAGAGGAAAGAGAAAGCCAAGATCCACTACC
GGAAGAAGAAACAGCTCATGAGGCTACGGAAACAGGCCGAGAAGAACGTG
GAGAAGAAAATTGACAAATACACAGAGGTCCTCAAGACCCACGGACTCCT
GGTCTGAGCCCAATAAAGACTGTTAATTCCTCATGCGTTGCCTGCCCTTC
CTCCATTGTTGCCCTGGAATGTACGGACCCAGGGCAGCAGCAGTCCAGG
TGCCACAGGCAGCCCTGGGACATAGGAAGCTGGGAGCAAGGAAAGGGTCT
TAGTCACTGCCTCCCGAAGTTGCTTGAAAGCACTCGGAGAATTGTGCAGG
TGTCATTTATCTATGACCAATAGGAAGCAACCAGTTACTATGAGTGAAAG
GGAGCCAGAAGACTGATTGGAGGGCCCTATCTTGTGAGTGGGGCATCTGT
TGGACTTTCCACCTGGTCATATACTCTGCAGCTGTTAGAATGTGCAAGCA
CTTGGGGACAGCATGAGCTTGCTGTTGTACACAGGGTATT

XI-13
(SEQ ID NO: 134)
CTGCCAACATGGTGTTCAGGCGCTTCGTGGAGGTTGGCCGGGTGGCCTAT
GTCTCCTTTGGACCTCATGCCGGAAAATTGGTCGCGATTGTAGATGTTAT
TGATCAGAACAGGGCTTTGGTCGATGGACCTTGCACTCAAGTGAGGAGAC
AGGCCATGCCTTTCAAGTGCATGCAGCTCACTGATTTCATCCTCAAGTTT
CCGCACAGTGCCCACCAGAAGTATGTCCGACAAGCCTGGCAGAAGGCAGA
CATCAATACAAAATGGGCAGCCACACGATGGGCCAAGAAGATTGAAGCCA
GAGAAAGGAAAGCCAAGATGACAGATTTTGATCGTTTTAAAGTTATGAAG
GCAAAGAAAATGAACAGAATAATCAAGAATGAAGTTAAGAAGCTTCAAAA
GGCAGCTCTCCTGAAAGCTTCTCCCAAAAAAGCACCTGGTACTAAGGGTA
CTGCTGCTGCTGCTGCTGCTGCTGCTGCTGCTGCTGCTGCTGCTGCT
AAAGTTCCAGCAAAAAAGATCACCGCCGCGAGTAAAAAGGCTCCAGCCCA
GAAGGTTCCTGCCCAGAAAGCCACAGGCCAGAAAGCAGCGCCTGCTCCAA
AAGCTCAGAAGGGTCAAAAAGCTCCAGCCCAGAAAGCACCTGCTCCAAAG
GCATCTGGCAAGAAAGCATAAGTGGCAATCATAAAAAGTAATAAAGGTTC
TTTTTGACCTGTTAAAAAA

XI-49
(SEQ ID NO: 135)
GATCAACCTGGAGCTCTACGCCTCCTACGTTTACCTGTCCATGTCTTACT
ACTTTGACCGCGATGATGTGGCTTTGAAGAACTTTGCCAAATACTTTCTT
CACCAATCTCATGAGGAGAGGGAACATGCTGAGAAACTGATGAAGCTGCA

-continued

GAACCAACGAGGTGGCCGAATCTTCCTTCAGGATATCAAGAAACCAGACT

GTGATGACTGGGAGAGCGGGCTGAATGCAATGGAGTGTGCATTACATTTG

GAAAAAAATGTGAATCAGTCACTACTGGAACTGCACAAACTGGCCACTGA

CAAAAATGACCCCCATTTGTGTGACTTCATTGAGACACATTACCTGAATG

AGCAGGTGAAAGCCATCAAAGAATTGGGTGACCACGTGACCAACTTGCGC

AAGATGGGAGCGCCCGAATCTGGCTTGGCGGAATATCTCTTTGACAAGCA

CACCCTGGGAGACAGTGATAATGAAAGCTAAGCCTCGGGCTAATTTCCCC

ATAGCCGTGGGGTGACTTCCCTGGTCACCAAGGCAGTGCATGCATGTTGG

GGTTTCCTTTACCTTTTCTATAAGTTGTACCAAAACATCCACTTAGTTCT

TTGATTTGTACCATTCCTTCAAATAAAGAAATTTGGTACCC

XI-81
(SEQ ID NO: 136)
AGAGCAGCAGCCATGGCCCTACGCTACCCTATGGCCGTGGGCCTCAACAA

GGGCCACAAAGTGACCAAGAACGTGAGCAAGCCCAGGCACAGCCGACGCC

GCGGGCGTCTGACCAAACACACCAAGTTCGTGCGGGACATGATTCGGGAG

GTGTGTGGCTTTGCCCCGTACGAGCGGCGCGCCATGGAGTTACTGAAGGT

CTCCAAGGACAAACGGGCCCTCAAATTTATCAAGAAAAGGGTGGGGACGC

ACATCCGCGCCAAGAGGAAGCGGGAGGAGCTGAGCAACGTACTGGCCGCC

ATGAGGAAAGCTGCTGCCAAGAAAGACTGAGCCCCTCCCCTGCCCTCTCC

CTGAAATAAA

XII-35
(SEQ ID NO: 137)
CTCTCCTGTCAACAGCGGCCAGCCTCCCAACTACGAGATGCTCAGGAGGA

GCAGGAAGTGGCTATGCTGGGGGCGCCCCACAACCCTGCTCCCCCGACGT

CCACCGTGATCCACATCCGCAGCGAGACCTCCGTGCCCGACCATGTCGTC

TGGTCCCTGTTCAACACCCTCTTCATGAACACCTGCTGCCTGGGCTTCAT

AGCATTCGCCTACTCCGTGAAGTCTAGGGACAGGAAGATGGTTGGCGACG

TGACCGGGGCCCAGGCCTATGCCTCCACCGCCAAGTGCCTGAACATCTGG

GCCCTGATTTTGGGCATCTTCATGACCATTCTGCTCGTCATCATCCCAGT

GTTGGTCGTCCAGGCCCAGCGATAGATCAGGAGGCATCATTGAGGCCAGG

AGCTCTGCCCGTGACCTGTATCCCACGTACTCTATCTTCCATTCCTCGCC

CTGCCCCCAGAGGCCAGGAGCTCTGCCCTTGACCTGTATTCCACTTACTC

CACCTTCCATTCCTCGCCCTGTCCCCACAGCCGAGTCCTGCATCAGCCCT

TTATCCTCACACGCTTTTCTACAATGGCATTCAATAAAGTGTATATGTTT

CTGGTGCTGCTGTGACTTCAA

XII-77
(SEQ ID NO: 138)
GTAAGAAAGCCCTTAAATAAAGAAGGTAAGAAACCTAGGACCAAAGCACC

CAAGATTCAGCGTCTTGTTACTCCACGTGTCCTGCAGCACAAACGGCGGC

GTATTGCTCTGAAGAAGCAGCGTACCAAGAAAAATAAAGAAGAGGCTGCA

GAATATGCTAAACTTTTGGCCAAGAGAATGAAGGAGGCTAAGGAGAAGCG

CCAGGAACAAATTGCGAAGAGACGCAGACTTTCCTCTCTGCGAGCTTCTA

CTTCTAAGTCTGAATCCAGTCAGAAATAAGATTTTTTGAGTAACAAATAA

ATAAGATCAGACTCTGAAAAAAAAAAAAAAAAAAAAAAAAAAAAAAAA

AAAAAAAAAAAAAAAAAAAAA

XIII-29
(SEQ ID NO: 139)
CTCGCTCACGCAGCACTCGTGGCAGTCCCTGAAGGACCGCTACCTCAAGC

ACCTGCGGGCCAGGAGCATAAGTACCTGCTGGGGGACGCGCCGGTGAGC

CCCTCCTCCCAGAAGCTCAAGCGGAAGGCGGAGGAGGACCCGGAGGCCGC

GGATAGCGGGGAACCACAGAATAAGAGAACTCCAGATTTGCCTGAAGAAG

AGTATGTGAAGGAAGAAATCCAGGAGAATGAAGAAGCAGTCAAAAAGATG

CTTGTGGAAGCCACCCGGGAGTTTGAGGAGGTTGTGGTGGATGAGAGCCC

TCCTGATTTTGAAATACATATAACTATGTGTGATGATGATCCACCCACAC

CTGAGGAAGACTCAGAAACACAGCCTGATGAGGAGGAAGAAGAAGAAGAA

GAAAAAGTTTCTCAACCAGAGGTGGGAGCTGCCATTAAGATCATTCGGCA

GTTAATGGAGAAGTTTAACTTGGATCTATCAACAGTTACACAGGCCTTCC

TAAAAAATAGTGGTGAGCTGGAGGCTACTTCCGCCTTCTTAGCGTCTGGT

CAGAGAGCTGATGGATATCCCATTTGGTCCCGACAAGATGACATAGATTT

GCAAAAAGATGATGAGGATACCAGAGAGGCATTGGTCAAAAAATTTGGTG

CTCAGAATGTAGCTCGGAGGATTGAATTTCGAAAGAAATAATTGGCAAGA

TAATGAGAAAAGAAAAAAGTCATGGTAGGTGAGGTGGTTAAAAAAAATTG

TGACCAATGAACTTTAGAGAGTTCTTGCATTGGAACTGGCACTTATTTTC

TGACCATCGCTGCTGTTGCTCTGTGAGTCCTAGATT

XIII-84
(SEQ ID NO: 140)
ATTATCCTCAGTTCCCAAGAGCAATCATACTTTTCCACACATACCGTGTG

TCTCATGTTAGGTAAATGTATTTTTACAATGAGCACCACTTCTGTGGAAA

AAGTTCCCTGCACGGGGAGGTCCAGCTTCCAGACTGCTCCATCGCATAAG

GACTTCCCCATTCCCCTAAATGCTGCTCTGTCAGAACCTGCCCAGGTAAT

GGTAATGACCCTAGAGAGATGATTTCTGAACCGCAATTTTGAGCCCATTA

GAAGGTGTGTGGTGGGCATTTATTTCATCCTGATGCTCTGGTGAGAATCT

TTGCAGACGCACTAGATCCAGAAGCTGTTAATCTTGGTGCATTTATTTTC

CTACCTAAAAGAACCAAGCAGCTCAGAGGCAGTGACTGTACAGGATGCAG

TGTTTATAATAATGCTGAGCTTGCTGGTCTGGAACCCCACACTTCAGCAA

TCCCAGCATTGTTCCTGTTTATGAAGTTGACAAAGTGACCAGGGCAAGGG

GGTATTATCATTAAATACACTCTAGGAGAGGCAGAACACATGAGGGCAAT

GTTTTTCAGAGGTCTTTAGGCCACCGCATCAGATTCTCCTGGAGCATAAA

GCAAATGCTTTATGAGTCCAGGGCCCCTGCAGACCTACTGTATACTAGTA

TACAGCTCCCTCTTAGTGGATCTCAAGCTTGTTTCCAAAAAGTCATTACA

CTCCTTACCAAAGCCCATGACACATTCATACAGATTCATCCAGACATAAC

CCACTGCATGGTCCAGTGCATGCTTGTGTGCTTAACTTATTATAGATCAA

GTGTTATTTAAGTCCAACATATTAAACGTGACTGAATATT

XV-49
(SEQ ID NO: 141)
AAGTCTGCCCAGAAAGCTCAGAAGGCTAAATGAATATTATCCCTAATACC

TGCCACCCCACTCTTAATCAGTGGTGGAAGAACGGTCTCAGAACTGTTTG

```
TTTCAATTGGCCATTTAAGTTTAGTAGTAAAAGACTGGTTAATGATAACA

ATGCATCGTAAAACCTTCAGAAGGAAAGGAGAATGTTTTGTGGACCACTT

TGGTTTTCTTTTTTGCGTGTGGCAGTTTTAAGTTATTAGTTTTTAAAATC

AGTACTTTTTAATGGAAACAACTTGACCAAAAATTTGTCACAGAATTTTG

AGACCCATTAAAAAAGTTAAATGAG

XV-54
                                         (SEQ ID NO: 142)
AAGAGCAGGTCTCTGGAGGCTGAGTTGCATGGGGCCTAGTAACACCAAGC

CAGTGAGCCTCTAATGCTACTGCGCCCTGGGGGCTCCCAGGGCCTGGGCA

ACTTAGCTGCAACTGGCAAAGGAGAAGGGTAGTTTGAGGTGTGACACCAG

TTTGCTCCAGAAAGTTTAAGGGGTCTGTTTCTCATCTCCATGGACATCTT

CAACAGCTTCACCTGACAACGACTGTTCCTATGAAGAAGCCACTTGTGTT

TTAAGCAGAGGCAACCTCTCTCTTCTCCTCTGTTTCGTGAAGGCAGGGGA

CACAGATGGGAGAGATTGAGCCAAGTCAGCCTTCTGTTGGTTAATATGGT

ATAATGCATGGCTTTGTGCACAGCCCAGTGTGGGATTACAGCTTTGGGAT

GACCGCTTACAAAGTTCTGTTTGGTTAGTATTGGCATAGTTTTTCTATAT

AGCCATAAATGCGTATATATACCCATAGGGCTAGATCTGTATCTTAGTGT

AGCGATGTATACATATACACATCCACCTACATGTTGAAGGGCCTAACCAG

CCTTGGGAGTATTGACTGGTCCCTTACCTCTTATGGCTAAGTCTTTGACT

GTGTTCATTTACCAAGTTGACCCAGTTTGTCTTTTAGGTTAAGTAAGACT

CGAGAGTAAAGGCAAGGAGGGGGGCCAGCCTCTGAATGCGGCCACGGATG

CCTTGCTGCTGCAACCCTTTCCCCAGCTGTCCACTGAAACGTGAAGTCCT

GTTTTGAATGCCAAACCCACCATTCACTGGTGCTGACTACATAGAATGGG

GTTGAGAGAAGATCAGTTTGGGCTTCACAGTGTCATTTGAAAACGTTTTT

TGTTTTGTTTTGTAATTATTGTGGAAAACTTTCAAGTGAACAGAAGGATG

GTGTCCTACTGTGGATGAGGGATGTAACAAGGGGATGGCTTTGATCCAAT

GGAGCCTGGGAGGTGTGCCCAGAAAGCTTGTCTGTAGCGGGTTTTGTGAG

AGTGAACACTTTCCACTTTTTGACACCTTATCCTGATGTATGGTTCCAGG

ATTTGGATTTTGATTTTCCAAATGTAGCTTGAAATTTCAATAAACTTTGC

TCTGTTTTTCTAAAAATAAAAAAAAAAAAAAAAAAAAAAAAA

XV-75
                                         (SEQ ID NO: 143)
AGCAGATGACCCTTCGTGGCACCCTCAAGGGCCACAACGGCTGGGTAACC

CAGATCGCTACTACCCCGCAGTTCCCGGACATGATCCTCTCCGCCTCTCG

AGATAAGACCATCATCATGTGGAAACTGACCAGGGATGAGACCAACTATG

GAATTCCACAGCGTGCTCTGCGGGTCACTCCCACTTTGTTAGTGATGTG

GTTATCTCCTCAGATGGCCAGTTTGCCCTCTCAGGCTCCTGGGATGGAAC

CCTGCGCCTCTGGGATCTCACAACGGGCACCACCACGAGGCGATTTGTGG

GCCATACCAAGGATGTGCTGAGTGTGGCCTTCTCCTCTGACAACCGGCAG

ATTGTCTCTGGATCTCGAGATAAAACCATCAAGCTATGGAATACCCTGGG

TGTGTGCAAATACACTGTCCAGGATGAGAGCCACTCAGAGTGGGTGTCTT

GTGTCCGCTTCTCGCCCAACAGCAGCAACCCTATCATCGTCTCCTGTGGC

TGGGACAAGCTGGTCAAGGTATGGAACCTGGCTAACTGCAAGCTGAAGAC

CAACCACATTGGCCACACAGGCTATCTGAACACGGTGACTGTCTCTCCAG

ATGGATCCCTCTGTGCTTCTGGAGGCAAGGATGGCCAGGCCATGTTATGG

GATCTCAACGAAGGCAAACACCTTTACACGCTAGATGGTGGGGACATCAT

CAACGCCCTGTGCTTCAGCCCTAACCGCTACTGGCTGTGTGCTGCCACAG

GCCCCAGCATCAAGATCTGGGATTTAGAGGGAAAGATCATTGTAGATGAA

CTGAAGCAAGAAGTTATCAGTACCAGCAGCAAGGCAGAACCACCCCAGTG

CACCTCCCTGGCCTGGTCTGCTGATGGCCAGACTCTGTTTGCTGGCTACA

CGGACAACCTGGTGCGAGTGTGGCAGGTGACCATTGGCACACGCTAGAAG

TTTATGGCAGAGCTTTACAAATAAAAAAAAAAACTGGCTTTTCTGACAAAA

AAAAAA

XV-86
                                         (SEQ ID NO: 144)
GCAAAATGTCGCAGCTGGAACGCAACATAGAGACCATCATCAACACCTTC

CACCAATACTCTGTGAAGCTGGGGCACCCAGACACCCTGAACCAGGGGGA

ATTCAAAGAGCTGGTGCGAAAAGATCTGCAAAATTTTCTCAAGAAGGAGA

ATAAGAATGAAAAGGTCATAGAACACATCATGGAGGACCTGGACACAAAT

GCAGACAAGCAGCTGAGCTTCGAGGAGTTCATCATGCTGATGGCGAGGCT

AACCTGGGCCTCCCACGAGAAGATGCACGAGGGTGACGAGGGCCCTGGCC

ACCACCATAAGCCAGGCCTCGGGGAGGGCACCCCCTAAGACCACAGTGGC

CAAGATCACAGTGGCCACGGCCACGCCACAGTCATGGTGGCCACGGCCA

CAGCCACTAATCAGGAGGCCAGGCCACCCTGCCTCTACCCAACCAGGGCC

CCGGGGCCTGTTATGTCAAACTGTCTTGGCTGTGGGGCTAGGGGCTGGGG

CCAAATAAAGTCTCTTCCTCCAAAAAAAAAAAAAAAAAAAAAAAAAAAAA

AAAAAAAAAAA

XVI-74
                                         (SEQ ID NO: 145)
CGCCGCCGCGCCGCCGTCGCTCTCCAACGCCAGCGCCGCCTCTCGCTCGC

CGAGCTCCAGCCGAAGGAGAAGGGGGGTAAGTAAGGAGGTCTCTGTACCA

TGGCTCGTACAAAGCAGACTGCCCGCAAATCGACCGGTGGTAAAGCACCC

AGGAAGCAACTGGCTACAAAAGCCGCTCGCAAGAGTGCGCCCTCTACTGG

AGGGGTGAAGAAACCTCATCGTTACAGGCCTGGTACTGTGGCGCTCCGTG

AAATTAGACGTTATCAGAAGTCCACTGAACTTCTGATTCGCAAACTTCCC

TTCCAGCGTCTGGTGCGAGAAATTGCTCAGGACTTTAAAACAGATCTGCG

CTTCCAGAGCGCAGCTATCGGTGCTTTGCAGGAGGCAAGTGAGGCCTATC

TGGTTGGCCTTTTTGAAGACACCAACCTGTGTGCTATCCATGCCAAACGT

GTAACAATTATGCCAAAAGACATCCAGCTAGCACGCCGCATACGTGGAGA

ACGTGCTTAAGAATCCACTATGATGGGAAACATTTCATTCTCAAAAAAAA

AAAAAAAAAATTTCTCTTCTTCCTGTTATTGGTAGTTCTGAACGTTAGAT

ATTTTTTTTCCATGGGGTCAAAAGGTACCTAAGTATATGATTGCGAGTGG

AAAAATAGGGGACAGAAATCAGGTATTGGCAGTTTTTCCATTTTCATTTG

TGTGTGAATTTTTAATATAAATGCGGAGACGTAAAGCATTAATGCAAGTT

AAAATGTTTCAGTGAACAAGTTTCAGCGGTTCAACTTTATAATAATTATA
```

```
AATAAACCTGTTAAATTTTTCTGGACAATGCCAGCATTTGGATTTTTTA

AAACAAGTAAATTTCTTATTGATGGCAACTAAATGGTGTTTGTAGCATTT

TTATCATACAGTAGATTCCATCCATTCACTATACTTTTCTAACTGAGTTG

TCCTACATGCAAGTACATGTTTTTAATGTTGTCTGTCTTCTGTGCTGTTC

CTGTAAGTTTGCTATTAAAATACATTAAACTATAAAAAAAAAAAAAAAAA

AA

XVII-77
                                        (SEQ ID NO: 146)
CAGACACCCTGAACCAGGGGGAATTCAAAGAGCTGGTGCGAAAAGATCTG

CAAAATTTTCTCAAGAAGGAGAATAAGAATGAAAAGGTCATAGAACACAT

CATGGAGGACCTGGACACAAATGCAGACAAGCAGCTGAGCTTCGAGGAGT

TCATCATGCTGATGGCGAGGCTAACCTGGGCCTCCCACGAGAAGATGCAC
```

```
GAGGGTGACGAGGGCCCTGGCCACCACCATAAGCCAGGCCTCGGGGAGGG

CACCCCCTAAGACCACAGTGGCCAAGATCACAGTGGCCACGGCCACGGCC

ACAGTCATGGTGGCCACGGCCACAGCCACTAATCAGGAGGCCAGGCCACC

CTGCCTCTACCCAACCAGGGCCCCGGGGCCTGTTATGTCAAACTGTCTTG

GCTGTGGGCTAGGGGCTGGGGCCAAATAAAGTCTCTTCCTCCAAAAAAA
```

XII-78
no sequence available

Table 1. Sample detail. Stage 0, in situ carcinoma; Stage I, invasive carcinoma with tumour size <20 mm; Stage II, invasive carcinoma with tumour size >20-50 mm; Stage III, invasive carcinoma with tumour size >50 mm. Stage IV, cancer spread to distant parts. IDC, invasive ductal carcinoma; DCIS, ductal carcinoma in situ; ILC, invasive lobular carcinoma. n.a., not available. ND, non-decision. *, Blood samples taken at five consecutive weeks from the same female

TABLE 1

Sample detail.

| Female ID | Age | Stage | Histology | Grade | Size (mm) | Nodes | Other disease if present/comments | Times assayed | Final prediction |
|---|---|---|---|---|---|---|---|---|---|
| 1 | 51 | II | IDC | 3 | 20 | 1/7 | — | 2 | + |
| 2 | 84 | II | IDC | 1 | 22 | 2/2 | — | 2 | + |
| 3 | 50 | I | IDC (multifocal) | 1 | 5 × 14 | 0 | — | 1 | + |
| 4 | 66 | I | IDC | 2 | 15 | 0 | Rheumatic disease | 3 | + |
| 5 | 66 | II | IDC | 1 | 26 | 0 | Epilepsy | 1 | + |
| 6 | 47 | I | IDC | 2 | 15 | 0 | — | 2 | ND |
| 7 | 69 | III | ILC + tubular adenocarcinoma | 2 + 1 | 50 + 3 | 2/19 | — | 2 | ND |
| 8 | 50 | II | IDC | 2 | 24 | 0 | — | 2 | + |
| 9 | 65 | I | IDC | 1 | 15 | 0 | — | 1 | − |
| 10 | 63 | II | IDC | 3 | 23 | 0 | — | 1 | + |
| 11 | 65 | IV | | | | Metastases in supre and infraclavicular nodes | — | 1 | − |
| 12 | 52 | I | IDC | 1 | 3 | 0 | — | 2 | + |
| 13 | 60 | II | IDC | 2 | 23 | 0 | — | 2 | + |
| 14 | 54 | I | IDC | 1 | 11 | 0 | — | 2 | + |
| 15 | 67 | 0 | DCIS | 2 | 20 | 0 | — | 3 | + |
| 16 | n.a. | 0 | DCIS | 2 | 9 | 0 | — | 1 | − |
| 17 | 48 | I | IDC | 2 | 4 | 0 | — | 2 | + |
| 18 | n.a. | I | IDC | 2 | 14 | 0 | Psoriasis | 1 | + |
| 19 | 68 | I | IDC | 1 | 7 | 0 | — | 1 | + |
| 20 | 63 | I | IDC | 1 | 10 | 0 | — | 2 | + |
| 21 | 65 | I | IDC | 1 | 11 | 0 | Type II Diabetes | 3 | + |
| 22 | 44 | II | IDC | 2 | 25 | 0 | — | 1 | + |
| 23 | 55 | III | IDC | 1 | 35 | 0 | — | 1 | + |
| 24 | 71 | I | IDC | 1 | 8 | 0 | — | 1 | + |

Stage 0, in situ carcinoma;
Stage I, invasive carcinoma with tumour size <20 mm;
Stage II, invasive carcinoma with tumour size >20-50 mm;
Stage III, invasive carcinoma with tumour size >50 mm.
Stage IV, cancer spread to distant parts.
IDC, invasive ductal carcinoma ;
DCIS, ductal carcinoma in situ;
ILC, invasive lobular carcinoma.
n.a., not available.
ND, non-decision.
*, Blood samples taken at five consecutive weeks from the same female

| Subgroup A2: Women with abnormal first mammography | | | | | |
|---|---|---|---|---|---|
| Female ID | Age | Breast abnormality | Other disease if present/comments | Times assayed | Final prediction |
| 25 | 44 | Benign density | — | 2 | + |
| 26 | 46 | Benign density | — | 2 | + |
| 27 | 53 | Benign microcacifications | Encapsulated cyst in left knee | 2 | + |
| 28 | 52 | Benign microcacifications | Cancer, large intestine, 1992 | 1 | ND |
| 29 | 45 | Benign density | — | 2 | + |
| 30 | 59 | Benign tumour, Fibroadenoma | — | 2 | + |
| 31 | 46 | Benign density | — | 2 | + |
| 32 | 46 | Benign density | Ulcerative colitis since 1983 | 2 | ND |
| 33 | 50 | Benign density | Type 1 Diabetes | 2 | + |
| 34 | 47 | Benign microcacifications | — | 2 | + |
| 35 | 46 | Benign density, cyst | Crohn's disease | 2 | + |
| 36 | n.a. | Benign density | Rheumatic disease | 1 | + |
| 37 | 44 | Benign microcacifications | — | 2 | + |
| 38 | 47 | Benign Density | — | 2 | + |
| 39 | 50 | Fibrosis, benign | Size histology 60 mm | 1 | + |
| 40 | 45 | Benign density | Type II Diabetes | 2 | + |
| 41 | 63 | Benign density, cyst. | Fibromyalgi | 2 | + |
| 42 | 44 | Benign density | — | 2 | + |
| 43 | 51 | Radial scar | Size histology 10 mm | 1 | + |

| Subgroup A3: Women with no breast abnormality | | | | |
|---|---|---|---|---|
| Female ID | Age | Comments | Times assayed | Predictiom |
| 44 | 22 | — | 2 | + |
| 45 | 34 | Pregnant, 8 months | 3 | + |
| 46 | 27 | Pregnant, 6 months | 1 | + |
| 47* | 18 | Week 1 | 2 | + |
|  |  | Week 2 | 1 | + |
|  |  | Week 3 | 1 | + |
|  |  | Week 4 | 2 | + |
|  |  | Week 1 | 1 | + |
| 48 | 29 | Pregnant, 9 months | 1 | − |
| 49 | 30 | Breast feeding | 2 | + |
| 50 | 26 | — | 1 | + |
| 51 | 43 | — | 1 | + |
| 52 | 42 | — | 3 | + |
| 53 | 43 | — | 2 | + |
| 54 | 34 | Breast feeding | 3 | + |
| 55 |  | — | 1 | + |
| 56 | 51 | Acute bacterial infection in adddition to chronic EBV infection | 1 | + |

TABLE 2

Details of the 35 significant genes selected by Jackknife. Their position in the array, clone ID is shown as well as the accession number of sequences in public databases that match them, and their known or putative cellular function.

| Clone ID | Position ID | Accession number | Gene similarity | Putative biological function |
|---|---|---|---|---|
| UPREGULATED GENES | | | | |
| III-2 | 6A | no hit | — | — |
| III-27 | 10M | AC096970 | Chromosome 3 clone RP11-321A23; From sequence no. 135183-135446 | — |
| III-60 | 14AC | NM_001665 | Ras homolog gene family, member G (rho G) | Signal transduction, Kinase inhibitor? (RhoH has been described as a kinase inhibitor) |
| IV-26 | 6N | BC016857 | Ferritin, heavy polypeptide 1 | Iron storage; defence against ROS |
| IV-51 | 10Z | BC042655 | Upstream transcription factor 2, USF2 | Transcriptional regulator |
| VI-44 | 14X | AC087441 | Chromosome 11, From sequence no. 116068-116692 | — |
| VI-52 | 14AB | no hit | — | — |
| VII-15 | 27E | BC001431 | S100 calcium binding protein A6 (calcyclin) | Defence; inhibition of caseine kinase II |
| VII-32 | 31M | M28697 | Human low-affinity IgG Fc receptor (alpha-Fc-gamma-RII) | Immune response |
| IX-24 | 31J | BC047681 | S100 calcium binding protein A9 (calgranulin B) | Defence; inhibition of caseine kinase II |

TABLE 2-continued

Details of the 35 significant genes selected by Jackknife. Their position in the array, clone ID is shown as well as the accession number of sequences in public databases that match them, and their known or putative cellular function.

| Clone ID | Position ID | Accession number | Gene similarity | Putative biological function |
|---|---|---|---|---|
| IX-50 | 7Z | NM_007161 | Leukocyte-specific transcript 1 | Defence-related |
| XI-49 | 3AB | BC016857 | Ferritin, heavy polypeptide 1, mRNA | Iron storage; defence against ROS |
| XII-35 | 12Q | BC009696 | Interferon induced transmembrane protein 2 | Immune response |
| XII-78 | 24K | — | — | — |
| XIII-84 | 16AP | AL391903 | From sequence number 75875-76710 | — |
| XV-54 | 24AA | BC018148 | Delta sleep inducing peptide, immunoreactor | Immune response? |
| XV-86 | 24AQ | BC047681 | S100 calcium binding protein A9 (calgranulin B) | Defence; inhibition of caseine kinase II |
| XVI-74 | 5AK | BC066901 | H3 histone, family 3B (H3.3B) | Chromatin-remodelling; |
| XVII-77 | 20AN | BC047681 | S100 calcium binding protein A9 (calgranulin B) | Defence; inhibition of caseine kinase II |

Downregulated genes

| Clone ID | Position ID | Accession number | Gene similarity | Putative biological function |
|---|---|---|---|---|
| I-30 | 21O | BC009689 | Cyclin D-type binding protein | E2F-mediated transcription |
| IV-41 | 2V | BC010165 | Ribosomal protein S2 | Ribosome production |
| V-09 | 2G | BC053370 | Ribosomal protein SA | Ribosome production |
| V-38 | 22S | NM_001016 | Ribosomal protein S12 | Ribosome production |
| VI-49 | 2AB | NM_001023 | Ribosomal protein S20 (RPS20) | |
| VII-48 | 31U | M22146 | Ribosomal protein S4 | Ribosome production s |
| VII-76 | 15AK | AY495316 | Cytochrome c oxidase subunit, COX 1 | Mitochondrial electron transport chain |
| IX-39 | 27R | BC001037 | Ribosomal protein L35a | Ribosome production |
| IX-46 | 23V | BC034149 | Ribosomal protein S3 | Ribosome production |
| X-77 | 19AM | BC000514 | Ribosomal protein L13a | Ribosome production |
| XI-13 | 19H | D87735 | Ribosomal protein L14 | Ribosome production |
| XI-81 | 3AR | AF077043 | 60S Ribosomal protein L36 | Ribosome production |
| XII-77 | 20AK | BC035447 | Ribosomal protein S6 | Ribosome production |
| XIII-29 | 20N | BC004465 | Telomeric repeat binding factor 2, interacting protein | Telomere length regulation |
| XV-49 | 4AA | BC018641 | Eukaryotic translation elongation factor 1 alpha 1, (EEF1A) | Protein translation |
| XV-75 | 12AM | BC019093 | Guanine nucleotide binding protein, beta polypeptide 2-like; RACKs (for 'receptors for activated C-kinase) | Protein translation |

TABLE 3

Informative probes for breast cancer - family (i) and (ii) genes

| Probe No. | Agilent ID | Oligonucleotide sequence | |
|---|---|---|---|
| 2 | A_23_P164011 | ACTCCAGACTGGGAAGACCTTTCCATTTTCA GGATCGACGCTTCACGTTGAGGGGAGGGC | (SEQ ID NO 2) |
| 3 | A_23_P94111 | TTACCAAACTCAAAGCTTATTTGAGTAGAAT GGGCTCATGGGCAATGTGATGTTCCCTGT | (SEQ ID NO 3) |
| 5 | A_23_P155009 | TGTTGGTTGGAGGACAAGTGGGCACTGAGAC CCTGGTGACCCATGGAAAGGGTGGGCCTG | (SEQ ID NO 5) |

TABLE 3-continued

Informative probes for breast cancer - family (i) and (ii) genes

| Probe No. | Agilent ID | Oligonucleotide sequence | |
|---|---|---|---|
| 6 | A_23_P84323 | TGGAGAAAGGACCCTGGACCTGTGGGTCCAT CGTCCGTTCCAGGAGCAGGCAGGCTGGGG | (SEQ ID NO 6) |
| 8 | A_23_P121716 | TGGACATTCGAACAGAGTTCAAGAAGCATTA TGGCTATTCCCTATATTCAGCAATTAAAT | (SEQ ID NO 8) |
| 10 | A_23_P111037 | ATCAGAAGTCCACTGAACTGCTTATTCGTAA ACTACCTTTCCAGCGCCTGGTGCGCGAGA | (SEQ ID NO 10) |
| 13 | A_23_P75830 | TTTGTGGAAACTGTGTGTTATACTTTGTGGT ATAGACTGCCTGTTTAGTATGAAGGGGCG | (SEQ ID NO 13) |
| 16 | A_23_P149936 | CCTCCCAGCAGTTAAGTAACTTGTGTGAAGA TGGGACCCTTGTTCCTAATGGTTCTAGAA | (SEQ ID NO 16) |
| 17 | A_23_P134805 | CTGAATCTGTTTTGTCTTCCTAATCTATCAC AATTGCCACCCATCGGGTTTTGGGTGTGT | (SEQ ID NO 17) |
| 18 | A_23_P154235 | CCATGTTTCTGAATCTTCTTTGTTTCAAATG GTGCTGCATGTTTTCAACTACAATAAGTG | (SEQ ID NO 18) |
| 19 | A_23_P2616 | ATCATTCAGAATCTGAAAAGAAATTCTTCTT ATTTTCTGGGGCTGTCAGATCCAGGGGGT | (SEQ ID NO 19) |
| 20 | A_23_P333484 | CCACCGAGCTGCTGATCAGAAAGCTGCCTTT TCAGCGTCTGGTGCGTGAGATCGCGCAGG | (SEQ ID NO 20) |
| 24 | A_23_P259874 | TCTCAGAAGAATGTTGGCCATGAGACTATCA TTCAGAGGAGGAGGGGATTTCTCTCTTCA | (SEQ ID NO 24) |
| 26 | A_23_P206568 | AATCCTGTGATTCTGTGTGTGCCTGTGTGTG TATGCTGTTAATAAGATAAGGCTGCCCAT | (SEQ ID NO 26) |
| 27 | A_23_P115091 | GATGGCTGAAGGAGCTCTATGACCATGCTGA AGCCACGATCGTCGTCATGCTCGTGGGTA | (SEQ ID NO 27) |
| 28 | A_23_P46718 | TGCATGGGGAGTACATTCATCTGGAGGCTGC GTCCTGATGAATGTCCTGTCTGCTGGGGT | (SEQ ID NO 28) |
| 29 | A_23_P218456 | GTTTTTGAGTTTTTGCAGTTCAGTATCCCTC TGTCTATTCACACTTCGTGTTAGTGGTAA | (SEQ ID NO 29) |
| 31 | A_23_P76610 | CAGTTTATGGATGTCTGGGCAATCATAGCAC TTGCCATTTAAAAACATGCTACAGGGGCA | (SEQ ID NO 31) |
| 32 | A_23_P206396 | ATTATCAACTCACTGGTAACAACAGTATTCA TGCTCATCGTATCTGTGTTGGCACTGATA | (SEQ ID NO 32) |
| 34 | A_23_P56091 | GAAACCGGATCGCAAGCTTCCCAGGATTCCT CTTCGTGCTGCTGGGGGTGGGAAGCATGG | (SEQ ID NO 34) |
| 35 | A_23_P55184 | TCAATTTCAAGGCCTCCCTGCCTCTACTAGG CGCCTTAGCTCACTATGGGAACCACTTG | (SEQ ID NO 35) |
| 37 | A_23_P150974 | CAAAATAGCTACATCCCTGAACACAGTCCGG AATATTACGGCCGGACCAGGGAATCGGGA | (SEQ ID NO 37) |
| 40 | A_23_P111689 | TTAATTCTATTGGCTCTTAGTCACTTGGAAC TGATTAATTCTGACTTTCTGTCACTAAGC | (SEQ ID NO 40) |
| 41 | A_23_P58937 | GTCTCAAACAGCCGAAACCTGTCTTGCAATG GGGGAGGGGCGTTTCGCTTTCCTTCTT | (SEQ ID NO 41) |
| 42 | A_23_P74828 | TTGGCTTTTAGACATTATATATATTATCAGA GAAGTAGCCTAGTGGTCGTGGGGCACAGA | (SEQ ID NO 42) |
| 45 | A_23_P42168 | GGAACACTGTGAAAGTTACTTGGGGAGGGTG GGCCGGTGGGGCCGTAGCTCTCTACCTCT | (SEQ ID NO 45) |
| 47 | A_23_P81278 | TCAGACAGAGCTTGGTAAGTGACCCCTCTTA GAACTATTTCTCCTCAGGGCCGGGTCCAG | (SEQ ID NO 47) |
| 49 | A_23_P251695 | AGGTTGAACTCTTTTTTGTTGCTCAAGTTCT AGGAGTCCCTTTCCTGAATATATACTTGT | (SEQ ID NO 49) |

TABLE 3-continued

Informative probes for breast cancer - family (i) and (ii) genes

| Probe No. | Agilent ID | Oligonucleotide sequence | |
|---|---|---|---|
| 52 | A_23_P393645 | CTACTTTAGAGTCTTCTCCAATGTCCAAAAG GCTAGGGGGTTGGAGGTGGGGACTCTGGA | (SEQ ID NO 52) |
| 53 | A_23_P208683 | ATAGTCATGGGTGTCATGAAAAAATACCAAA TGTAAGAGAACCTCCAAGTCAGGGCGCAG | (SEQ ID NO 53) |
| 55 | A_23_P72016 | GACATTGAGAAGGAAAACCGGGAGGTGGGAG ACTGGCGCAAGAATATCGATGCACTAAGT | (SEQ ID NO 55) |
| 58 | A_23_P16915 | CATATTCCATTTTTAAGAAGAGGTGTTCCAG TTCTGCATCTGATACCGTCTCCTTTCCCT | (SEQ ID NO 58) |
| 60 | A_23_P37076 | GAAAATCCCTTGCTATGTCTTTCCTACTAGA AATGTTCTAGAATCGCTGGACGGTGGGGT | (SEQ ID NO 60) |
| 61 | A_23_P166408 | TGGTGGTGGATCCTGGAATTTTCTCACGCAG GAGCCATTGCTCTCCTAGAGGGGGTCTCA | (SEQ ID NO 61) |
| 63 | A_23_P94501 | GGCTCTTTGTGGAGGAAACTAAACATTCCCT TGATGGTCTCAAGCTATGATCAGAAGACT | (SEQ ID NO 63) |
| 67 | A_23_P94230 | TGAAGCTATTTCTGGGAGCCCAGAAGAAATG CTCTTTTGCTTGGAGTTTGTCATCCTACA | (SEQ ID NO 67) |
| 68 | A_23_P154037 | TTGGTTTCCTCTAGGGTGATATTCGTCATTA CTCTGTCTCTTCAATCCATCCAGCTAAAT | (SEQ ID NO 68) |
| 69 | A_23_P47938 | AAGAAAACACACCTCGGCGACAATGTCTTGC TGCTCGGATTAGGTGGGGGATGGGCGACA | (SEQ ID NO 69) |
| 70 | A_23_P90743 | CTGAGTTTGCCTTGTTAATCTTCAATAGTTT TACCTACCCCAGTCTTTGGAACCCTAAAT | (SEQ ID NO 70) |
| 71 | A_23_P171249 | AAAGTGTCAAGTGATTAAGTGTGTATTTGTA CCCTAGATGATATGAACCAGCAGTCTTGT | (SEQ ID NO 71) |
| 72 | A_23_P142675 | TGAGCTGTTCCCTTCTCTAAGCCATAATCTC TTAGTGGATTGAGCCCTCTTGGAAAGACT | (SEQ ID NO 72) |
| 73 | A_23_P153637 | TGTTATTGGCCTAGAGCTACACGTATATGGG TTTGTCCTGAGTCCGTTTTCAAATGACCT | (SEQ ID NO 73) |
| 76 | A_23_P76749 | CCTGTTCTGTTTTTGCTTTTCCTCTTCTTGA CCAAAGCATGTGCCACTAGCTGTCCTTGA | (SEQ ID NO 76) |
| 80 | A_23_P169061 | TTGAAGGCAAAGATCATCAATATCTGCATCT GGCTGCTGTCGTCATCTGTTGGCATCTCT | (SEQ ID NO 80) |
| 91 | A_23_P206253 | CGAATTGGGAGGCTTATATTTTTCAGCAAAG AAATTTTGGGGGGTTTTGTGTTGTTGGGC | (SEQ ID NO 91) |
| 95 | A_23_P151995 | AATAAACAACTTTGATGATGTAACTTGACCT TCCAGAGTTATGGAAATTTTGTCCCCATG | (SEQ ID NO 95) |
| 97 | A_23_P138011 | AGAGACCTGCAGGGGCCTCGGCCCCTCACAT CGTGTATGTCTCTCCTTGATTTGTGTTGT | (SEQ ID NO 97) |
| 100 | A_23_P35912 | GCCAAAGCTCAAATGCCCACCATAGAACGAC TGTCCATGACAAGATATTTCTACCTCTTT | (SEQ ID NO 100) |
| 101 | A_23_P99424 | TGGCTCCCCATCATGTATCCTCCCGATTATT GCGTATTCTAAAATAGGAAACAAGACTTT | (SEQ ID NO 101) |
| 105 | A_23_P418986 | GATGACACTGCCACCTCTGACTTCTGCCTC TGGCCTTCCACTCTCAGTAAGAAGAGCCAG | (SEQ ID NO 105) |

TABLE 4

Informative probes for breast cancer -
non-family (i) and (ii) genes

| Probe No. | Agilent ID | | |
|---|---|---|---|
| 1 | A_23_P366812 | TTTACTTCTACCTGCTCTTCCCCAACTCCCT GAGCCTGAGTGAGCGTGTGGCCATCATCA | (SEQ ID NO 1) |
| 4 | A_23_P389391 | TGGGCCTCAAAATGGAGATGGATCCCAGGTC TTGTGGGACCCTGGGATGTTTGGGGACTT | (SEQ ID NO 4) |
| 7 | A_23_P4096 | TAATATCCCCAAACCTGAGATGAGCACTACG ATGGCAGAGAGCAGCCTGTTGGACCTGCT | (SEQ ID NO 7) |
| 9 | A_23_P15450 | GACTGAAAAATCAGCTTTCTATTTACATGAA ACACTTTGGGGGTCATGGGAGTGCACAGC | (SEQ ID NO 9) |
| 11 | A_23_P379596 | AGGGATAATTCAAACTGACAACCTGTGCAGT CCCGTGGAGGGTAGGGGAGTGTGGGTGAT | (SEQ ID NO 11) |
| 12 | A_23_P391275 | TAAATTATGATTTACTCTGTGCTGTTTCCAA ATTGGGACCAGGAGAGAAATATGAACTTC | (SEQ ID NO 12) |
| 14 | A_23_P124661 | TCTATTATTTATAACTTCAGACTTGGGCCCC CTGTTCTTTCTTTCCCATTAACTTGAGTG | (SEQ ID NO 14) |
| 15 | A_23_P44257 | AACATTTTACTTCTGCGCTTCTATGTTTGGG AAACATTGCTCTGATAAAAAATAGCTGTC | (SEQ ID NO 15) |
| 21 | A_23_P128183 | CTGAGAGTTTTTGCAGAAATGGGGCAGAGGG ACACCCTTTGGGCGTGGCTTCCTGGTGAT | (SEQ ID NO 21) |
| 22 | A_23_P331211 | CGAGTGGCTCACTCAGAATTCTTCATTGATG GGGTAGGGACCCTACTCGTGGGGTCATGC | (SEQ ID NO 22) |
| 23 | A_23_P94932 | TCTGTTGATGACCTTGGATGCTGTAAAGTGA TTCGTCATAGTCTCTGGGGTACCCATGTA | (SEQ ID NO 23) |
| 25 | A_23_P102122 | AAGCGGCTGGCAACTGAAGGCTGGAACACTT GCTACTGGATAATCGTAGCTTTTAATGTT | (SEQ ID NO 25) |
| 30 | A_23_P407654 | GAGGAGCTCTTTTCTAGAGAGCCGGGAGTTG GGGAGGGGGTATTTATTTTGTTATTTATT | (SEQ ID NO 30) |
| 33 | A_23_P392457 | CCTCTGACTGCCTCCAACGTAAAAATGTAAA TATAAATTTGGTTGAGATCTGGAGGGGGG | (SEQ ID NO 33) |
| 36 | A_23_P406376 | GCCACACTGGCTTTAGGACCTGTTGACACGG AGGGGGGTTTTTAATTTGGTTTTTAACAA | (SEQ ID NO 36) |
| 38 | A_23_P22723 | AACAAACTACAGTTTTACCGTGTGTTGCCA TTTGAGCTGTGTGGTGGGCAGGGGCTGG | (SEQ ID NO 38) |
| 39 | A_23_P70258 | AGAGAGGATGGCTGTATTCCTATCCCAGCTC AAGCTGCCAGCAGCAATGTTGGCTGCCCA | (SEQ ID NO 39) |
| 43 | A_23_P104005 | AATTTTCAAGACTTCTTTTCACTCTTTGATT TGGATCTGGCAAATTGGGGAGGGGATGCT | (SEQ ID NO 43) |
| 44 | A_23_P119652 | TTGCCCAACTGACCGTGGGCTGAACACACGT TCTGCTTGACTCATTTAGGGGGAGGGAA | (SEQ ID NO 44) |
| 46 | A_23_P22957 | ATGAGGTGATCACTGTGTTCAGTGTTGTTGG AATGGATTCAGACTGGCTAATGGGGGAAA | (SEQ ID NO 46) |
| 48 | A_23_P8072 | GGGGGAGATCAGAATCGTCCAGCTGGGCTTC GACTTGGATGCCCATGGAATTATCTTCAC | (SEQ ID NO 48) |
| 50 | A_23_P23346 | AATCTTCTGAACGGCATAAGTCCTATTTTAG CCTTACCTCCTGCATTTGCAATACGTAAT | (SEQ ID NO 50) |
| 51 | A_23_P92342 | CGAACAAACAAAATACTTGGCGGGGCCCGAG AGGGCTCGTTTGGCCTATTCGTTGGGGAT | (SEQ ID NO 51) |
| 54 | A_23_P153183 | ACAGAAAACAGACTTGTAAAAAGCTTAGATC ATCAAGTGTTTTGGATTGGGGGCCTCCCA | (SEQ ID NO 54) |
| 56 | A_23_P157231 | TGCAGAATGCATAAGATGAACATTGCATGAC CGGATCATTTTAGTGTCTTTGCGTTAAAA | (SEQ ID NO 56) |

TABLE 4-continued

Informative probes for breast cancer - non-family (i) and (ii) genes

| Probe No. | Agilent ID | | |
|---|---|---|---|
| 57 | A_23_P103282 | TGAAGATCATGAAGAAGCAGGGCCTCTACCT ACAAAAGTGAATCTTGCTCATTCTGAAAT | (SEQ ID NO 57) |
| 59 | A_23_P109462 | CTGGATGTTTACCTGGAGACCGAGAGCCATG ACGACAGTGTGGAGGGGCCCAAGGAATTT | (SEQ ID NO 59) |
| 62 | A_23_P395460 | TTAATGCTTTATACTGCCGAGTCTGGGGGCT TGTTTTGGTTTGGGGGCAGCCATCCTCCA | (SEQ ID NO 62) |
| 64 | A_23_P418485 | TCTAGGACTAATTCACACTGCAACAAAGGGG CTGATTAGAGCTTTTGAAGATGGGGGGAT | (SEQ ID NO 64) |
| 65 | A_23_P215111 | GACTTAACCACGTCAGAGGAAGGACTTTGGC AAGTGATATTGTCTTCATGTGGGGTATTA | (SEQ ID NO 65) |
| 66 | A_23_P19543 | CTGTCAAATTGCCACGATCTCACTAAAGGAT TTCTATTTGCTGTCAGTTAAAAATAAAGC | (SEQ ID NO 66) |
| 74 | A_23_P18317 | TCATCTGCACTCAACATTTAATCGTGTCCTT GCTGTCTTTTTATTTTCCTTTTTGTTTGT | (SEQ ID NO 74) |
| 75 | A_23_P89369 | GCGGGAGGAGCGGCCGCTGATGGTGTTCAAC GTCAAGTAGCGCCCGCGCAGGGCGGGGCA | (SEQ ID NO 75) |
| 77 | A_23_P330561 | CTGTCTCCCTGTTTGTGTAAACATACTAGAG TATACTGCGGCGTGTTTTCTGTCTACCCA | (SEQ ID NO 77) |
| 78 | A_23_P206103 | GAGAGTTTCTTTTAAATAATCAGCGGGTGTT GGTGATTTGTAGCCCTTCTGCCCTTAAAT | (SEQ ID NO 78) |
| 79 | A_23_P98042 | ATACTTTGTGAGTTCACCTGTCTTTATACTC AAAAGTGTCCCTTAATAGTGTCCTTGCCC | (SEQ ID NO 79) |
| 81 | A_23_P166453 | ACCTTTGAATTTGCGGATGCTGAGGAGGATG ATGAGGTCAAGGTGTGAGGGGCTGGGGCA | (SEQ ID NO 81) |
| 82 | A_23_P432554 | TATTAGACTATGTCATCAATTTTTGCAAAGG TAAATTTGACTTCCTTGAACGGCTCTCAG | (SEQ ID NO 82) |
| 83 | A_23_P368028 | AAATACTGGGTGGCTTGGTTTAGAGCTAATT GTAGTGGAAGCCTGCAAGGTTGAGGGGTG | (SEQ ID NO 83) |
| 84 | A_23_P213334 | ACTCACTATGGCCAGAAAGCAATCTTGTTTC TCCCCCTGCCAGTCTCTTCTGATTAAAGA | (SEQ ID NO 84) |
| 85 | A_23_P102113 | AACAAATATTTATTTTGCACTCTCTTTGCGG CACTCTGGGGGCGGTGGGGTGCGTGGGGG | (SEQ ID NO 85) |
| 86 | A_23_P319682 | CAAGTTGTCACTGGAGATGCGCGCGGACTTG GCCCAAAACGTGCTTCTCTGCGGTGGGTC | (SEQ ID NO 86) |
| 87 | A_23_P104471 | GATTTCCCTGACCCAATTCAGAGATTCTTTA TGCAAAAGTGAGTTCAGTCCATCTCTATA | (SEQ ID NO 87) |
| 88 | A_23_P118749 | GAAGGACTCGGTGATACCCACTGGGATCTTT TATCCTTTGTTGCAAAAGTGTGGACACTT | (SEQ ID NO 88) |
| 89 | A_23_P420879 | CAGGGCAACTCAAAGAATGTTCTGCTGGCAT GTCCTATGAACATGTACCCGCATGGACGC | (SEQ ID NO 89) |
| 90 | A_23_P29816 | GAGAAAAGCAAAGCTCTTTCTTATTTTCCTC ATAATCAGCTACCCTGGAGGGGAGGGAGA | (SEQ ID NO 90) |
| 92 | A_23_P41992 | TGAAATGCTGGAAGGGTTCTTCTCCCACAAC CCCTGCCTCACGGAGGCCATTGCAGCTAA | (SEQ ID NO 92) |
| 93 | A_23_P75479 | AGACCTCGGTGATCACTGAGGGATTTCCGCG AGCTCGGCCTCACTTCTGCCCCGACTTGT | (SEQ ID NO 93) |
| 94 | A_23_P307940 | CTACAAGATTGGCAAAGAGATGCAGAATGCA TAAGATGAACATTGCATGACCGGATCATT | (SEQ ID NO 94) |

TABLE 4-continued

Informative probes for breast cancer - non-family (i) and (ii) genes

| Probe No. | Agilent ID | | |
|---|---|---|---|
| 96 | A_23_P98910 | AGGTTCTCAGAATGACCGTAAGATAGCTTAC ATTTCCTCTTTTTGCCTTTATCTCCCCAA | (SEQ ID NO 96) |
| 98 | A_23_P149736 | CCGTTTTGTTTCTGCTCAGTAATATAGTCAA GCAAGTTTGTTCCAAGTGACCCATTGAGC | (SEQ ID NO 98) |
| 99 | A_23_P320250 | AAATTGGCGCTGGAATTTGGGCTGGGAAAAA TCTTGTGGTTATTTCCTTTAAAAAGGAAC | (SEQ ID NO 99) |
| 102 | A_23_P55123 | TCACGTTAACATATAGACACTGTTGGAAGCA GTTCCTTCTAAAAGGGTAGCCCTGGACTT | (SEQ ID NO 102) |
| 103 | A_23_P251825 | CTATGACACCTTTAAGGAGGTTCTTGGATCA GGGATGCAGTACCCACTTGCAGTCAAAAT | (SEQ ID NO 103) |
| 104 | A_23_P109864 | TGTGGGTGTCCAGCATCTTCTTCTTCCTTCC TGTCTTCTGTCTCACGGTCCTCTACAGTC | (SEQ ID NO 104) |
| 106 | A_23_P428875 | GTCGCCTGGGATTTTCATCCCTCGCACAAGG ACTACGGGTTCACACGGTGAACTGGGGGA | (SEQ ID NO 106) |
| 107 | A_23_P73468 | GCCATAAGAAATTTGACAAGATGGTGGACAC TCCTGCCTCCGAGCCTGCCCAAGCCTCCA | (SEQ ID NO 107) |
| 108 | A_23_P106532 | AAGGCCTTTGAGGTTGTGACTGTGGCTGGTA TATCTGGCTGCCATTTTTCTGATGCATTT | (SEQ ID No 108) |
| 109 | A_23_P112251 | AGAATTCTTAACTTCACAAGTGTTTTACTTC GACGATGTGCCTTTGATTTAATTTGGGAC | (SEQ ID NO 109) |
| 110 | A_23_P313330 | TCATTAGACATCGGGGATTTCACTCTGCAGA GTAATCCTGGAACTACATTAAAGTGGGGG | (SEQ ID NO 110) |
| 111 | A_23_P27414 | TGCGGGAAGCCTTTCAGCCACCGTTGCAACC TCAACGAGCACCAGAAGCGGCACGGGGC | (SEQ ID NO 111) |
| 112 | A_23_P210981 | TTGTAGGACTTAATGGCTAAGAATTAGAACA TAGCAAGGGGCTCCTCTGTTGGAGTAAT | (SEQ ID NO 112) |

TABLE 5

Informative genes for breast cancer - family (i) and (ii) genes

| Probe No. | Accession No. 1 | Accession No. 2 | Gene similarity and putative biological function |
|---|---|---|---|
| | | | Transcription factors (family (i)) |
| 2 | NM_006942 | AB006867 | SRY (sex determining region Y)-box 20, a member of the SRY-related HMG box containing family of transcription factors |
| 3 | NM_002095 | X63469 | General transcription factor IIE 2 (34 kDa subunit), beta subunit of RNA polymerase II transcription factor TFIIE, required for transcription initiation, interacts with activators and DNA repair proteins, may play a role in transcription-coupled repair |
| 6 | NM_018942 | M99587 | H6 homeo box 1, a member of the homeodomain-containing family of DNA binding proteins, a transcriptional repressor that can antagonize mouse Nkx2-5 mediated transcriptional activation |
| 26 | | BC026031.1 | T-box 6, member of the T-box DNA binding domain family of transcription factors, may be involved in embryonic paraxial mesoderm formation and somitogenesis |
| 45 | NM_005586 | U78313 | MyoD family inhibitor, a putative transcriptional repressor that negatively regulates myogenesis |
| 69 | NM_014212 | AJ000041 | Homeobox C11, a homeodomain-containing transcription factor, may activate HNF1alpha (TCF1)-dependent transcription, may function in early development and differentiation of the intestine; NUP98-HOXC11 fusion protein is involved in myeloid malignancies |
| 105 | NM_004348 | | *Homo sapiens* runt-related transcription factor 2 (RUNX2), mRNA |
| | | | Defence-related genes (family (ii)) |
| 63 | NM_000700 | BC035993 | Annexin I, a calcium-dependent phospholipid-binding protein that inhibits phospholipase A2 and has anti-inflammatory activity, involved in the response to stress; associated with the early onset of tumorigenesis in esophageal and prostate carcinoma |
| 8 | NM_005139 | M63310 | Annexin A3 (lipocortin III), a member of the annexin family of calcium-dependent phospholipid-binding proteins, binds choline, helps regulate membrane fusion and permeability, and phagocytosis |

TABLE 5-continued

Informative genes for breast cancer - family (i) and (ii) genes

| Probe No. | Accession No. 1 | Accession No. 2 | Gene similarity and putative biological function |
|---|---|---|---|
| 13 | | BC007022.1 | Serum amyloid A1, an acute phase apolipoprotein that acts in leukocyte chemotaxis and induces matrix metalloproteases, may play a role in rheumatoid arthritis, atherosclerosis, reactive systemic AA amyloidosis, Alzheimers disease and multiple sclerosis |
| 18 | NM_004688 | BC001268 | N myc (and STAT) interactor, protein that interacts with N-myc (MYCN) and STAT proteins, augments IL2- and IFNgamma-responsive transcription by promoting association of CBP/p300 with STAT proteins, may aid BCRA1 to suppress breast cancer carcinogenesis |
| 19 | NM_203503 | AF325460 | C-type (calcium dependent, carbohydrate-recognition domain) lectin superfamily member 11, a dendritic cell glycoprotein that inhibits interferon alpha and beta induction and may mediate antigen capture for initiation of T cell-dependent immune responses |
| 27 | NM_020387 | AF274025 | Protein with high similarity to Ras p21-like small GTP-binding protein 11a (human RAB11A), which is a putative GTPase that is involved in phagocytosis and possibly vesicle transport, member of the Ras superfamily of GTP-binding proteins |
| 29 | NM_012218 | AJ271747 | Interleukin enhancer binding factor 3, a subunit of NF-AT, acts as a positive or negative transcriptional regulator, required for T-cell expression of IL2, possibly involved in mRNA processing, inhibition of translation, host defence and autoimmunity |
| 32 | NM_181640 | BC004380 | Chemokine-like factor 1, a secreted chemoattractant for leukocytes, neutrophils, monocytes and lymphocytes, stimulates inflammatory response and muscle stem cell proliferation and proliferation, plays a role in the regulation of myogenesis |
| 37 | NM_153633 | X07495 | Homeobox C4, a member of the homeobox family of DNA binding proteins, may play a role in the regulation of lymphocyte activation and lineage determination during hematopoiesis |
| 61 | NM_020530 | BC011589 | Oncostatin M, a member of the interleukin-6 cytokine family, produced by activated monocytes and T-lymphocytes, regulates cell growth and differentiation through activation of the JAK-STAT and MAPK pathways, regulates Kaposis sarcoma cell growth |
| 67 | NM_015364 | AB018549 | MD-2 protein, part of a lipopolysaccharide receptor complex, contributes to lipopolysaccharide and Toll-like receptor 4 (Tlr4) signalling, may play a role in the cellular defence response |
| 80 | NM_000912 | L37362 | Kappa opioid receptor 1, a G protein-coupled receptor that signals through an inhibitory G protein, may modulate sensory perception such as pain; altered expression is associated with Alzheimer disease; agonist stimulation may suppress HIV infections |
| 95 | NM_004049 | U29680 | BCL2-related protein A1, a member of the Bcl-2 family of apoptosis regulators, inhibits apoptosis, promotes tumorigenesis, and may play a protective role during inflammation |
| 17 | NM_003580 | BC041124 | Neutral sphingomyelinase (N-Smase) activation associated factor, mediates tumor necrosis factor receptor CD40 (TNFRSF5) induction of N-Smase, involved in TNF alpha mediated induction of apoptosis, binds to the TNF receptor TNF-R55 (TNFRSF1A) |
| 34 | NM_144615 | BC015655 | Protein containing an immunoglobulin (Ig) domain, which may be involved in protein-protein and protein-ligand interactions |
| | | | Chromatin remodelling (family (ii)) |
| 10 | NM_003529 | BC067491 | H3 histone family member A, a component of nucleosomes, along with core histones H2A, H2B, H4 and DNA |
| 20 | NM_003536 | BC062305 | *Homo sapiens* histone 1, H3h (HIST1H3H), mRNA |
| 31 | NM_018282 | AK090873 | Paraspeckle protein 1, a putative RNA-binding protein containing two RNA binding (RRM) domains, moves between the paraspeckle interchromatin space compartment and the nucleolus and interacts with the nucleolus in a transcription-dependent fashion |
| | | | Ribosomal biogenesis (family (i)) |
| 16 | | AK024156 | Protein of unknown function, has moderate similarity to a region of *S. cerevisiae* Bms1p, which is involved in rRNA processing and 40S ribosomal subunit biogenesis |
| | | | Protein metabolism (family (i)) |
| 52 | NM_139026 | AY358118 | *Homo sapiens* a disintegrin-like and metalloprotease (reprolysin type) with thrombospondin type 1 motif, 13 (ADAMTS13), transcript variant 1, mRNA |
| 72 | NM_012100 | AK001777 | Cytosolic aspartyl aminopeptidase, a member of the M18 family of metalloproteases, has a substrate preference for N-terminal aspartyl and glutamyl residues and may be involved in intracellular peptide metabolism |
| 100 | NM_001225 | U28979 | Caspase 4, a member of the ICE cysteine protease family that is involved in the induction of apoptosis; inhibition by the cowpox virus serpin CrmA may facilitate infection by inhibiting apoptosis |
| 101 | NM_003291 | AK097678 | Tripeptidyl peptidase II, a serine exopeptidase that may act in non-proteasomal protein turnover, neuropeptides and MHC class I antigens are substrates, acts in Shigella-activated apoptosis, upregulated in Burkitts lymphoma cells overexpressing MYC |
| 5 | NM_012265 | BC002705 | Member of the rhomboid family of integral membrane proteins, contains a UBA (ubiquitin associated) or TS-N domain |
| 55 | | M64247.1 | Protein with very strong similarity to cardiac troponin I (mouse Tnni3), which is the inhibitory subunit of troponin, member of the troponin family, which regulates calcium-induced muscle contraction |
| 76 | | BC036812 | Protein with high similarity to UDP-N-acetyl-alpha-D-galactosamine:polypeptide N-acetylgalactosaminyltransferase (human GALNT2), member of the glycosyl transferase family 2, contains 2 QXW (ricin B) lectin repeat domains |
| | | | Oxidative stress (family (ii)) |
| 58 | NM_012413 | X71125 | Glutaminyl-peptide cyclotransferase (glutaminyl cyclase), expressed in the pituitary, expression in lens epithelium is downregulated during oxidative stress |
| 68 | NM_001159 | L11005 | Aldehyde oxidase, a molybdenum-containing flavoenzyme involved in oxygen radical, xenobiotic, and drug metabolism; candidate gene for the cause of the autosomal recessive form of amyotrophic lateral sclerosis |
| 60 | NM_004873 | AK023145 | BCL2 associated athanogene 5, contains a BAG domain, predicted to regulate Hsc70/Hsp70 proteins by binding to their ATPase domains via its BAG domain |

TABLE 5-continued

Informative genes for breast cancer - family (i) and (ii) genes

| Probe No. | Accession No. 1 | Accession No. 2 | Gene similarity and putative biological function |
|---|---|---|---|
| | | | Protein secretion (Protein synthesis - family (i)) |
| 24 | NM_012430 | AF100749 | Sec22 homolog, a member of the SEC22 family of vesicle trafficking proteins, may be involved in protein trafficking from the endoplasmic reticulm to the Golgi apparatus |
| 28 | | M65199 | Endothelin 2, a member of a family of vasoactive peptide hormones, involved in blood pressure regulation, inhibits prolactin secretion, may act in cell growth related to heart development; locus amplification correlates with hypertension |
| 35 | NM_001661 | L38490 | ADP-ribosylation factor 4-like, a GTPase and member of the ADP-ribosylation factor family, may be involved in vesicular intracellular transport and protein secretion |
| 41 | | BC028121 | Protein with high similarity to translocating chain-associating membrane protein (human TRAM), which is a putative endoplasmic reticulum receptor that stimulates translocation of secretory proteins, member of the longevity-assurance protein (LAG1) family |
| 42 | NM_030772 | AF271261 | Member of the connexin family of gap junction channel proteins, which allow for intercellular passage of molecules, has moderate similarity to gap junction protein alpha 1 (connexin 43, human GJA1), which is associated with visceroatrial heterotaxia |
| 49 | NM_013248 | AK026360 | NTF2-like export protein 1, binds RAN, functions in the CRM1 (XPO1)-dependent nuclear export pathway |
| 53 | NM_012346 | | Nuclear pore glycoprotein p62, a component of the nuclear pore, may be involved in nucleocytoplasmic transport, targeted for degradation during poliovirus infection |
| 73 | NM_032139 | AL136784 | Protein containing a vacuolar sorting protein 9 (VPS9) domain and eight ankyrin (Ank) repeats, has a region of low similarity to a region of *C. elegans* UNC-44, which is required for axonal guidance and proper axon fasciculation |
| 91 | | AB010419.1 | Core-binding factor runt domain alpha subunit 2 translocated 3, member of the MTG8 (ETO/CDR) protein family, putative transcription factor; fusion of the corresponding gene to RUNX1 is seen in acute myeloid leukemia |
| 97 | | AL137537 | Protein with high similarity to aminophospholipid ATPase transporter (familial intrahepatic cholestasis 1, human ATP8B1), which is associated with familial intrahepatic cholestasis, member of the haloacid dehalogenase or epoxide hydrolase family |
| | | | B-cell morphogenesis (immune response, family (ii)) |
| 70 | NM_002909 | M27190 | Regenerating islet-derived 1 alpha (pancreatic stone protein), induces pancreatic beta cell regeneration, ameliorates diabetes in animals, aberrant expression is associated with chronic calcifying pancreatitis and colon carcinogenesis |
| 71 | NM_001551 | BC004137 | Immunoglobulin binding protein 1, may be involved in IgG receptor-mediated B cell signal transduction |
| 40 | | AC007032 | Pre-B cell colony-enhancing factor, a cytokine that synergizes the colony formation activity of stem cell factor (KITLG) and interleukin 7 (IL7) in early B-lineage cells; may play a role in infection-induced preterm birth and primary colorectal cancer |
| | | | Immune response (family (ii)) |
| 47 | NM_152547 | AK057097 | Protein with low similarity to B7 homolog 3 (human B7-H3), which is a costimulatory molecule for T-cells that positively regulates proliferation and interferon-gamma synthesis and is induced by inflammatory cytokines |

Accession numbers 1 and 2 provide alternative accession numbers for the gene. The relevant sequence may be identified in the NCBI database (www.ncbi.nlm.nih.gov).

TABLE 6

Informative genes for breast cancer - non-family (i) and (ii) genes

| Probe No. | Accession No. 1 | Accession No. 2 | Gene similarity and putative biological function |
|---|---|---|---|
| | | | Channels and pumps |
| 1 | NM_001651 | BC034356 | *Homo sapiens* aquaporin 5 (AQP5), mRNA |
| 4 | NM_005072 | AF054506 | *Homo sapiens* solute carrier family 12 (potassium/chloride transporters), member 4 (SLC12A4), mRNA |
| 11 | NM_004983 | U52152 | *Homo sapiens* potassium inwardly-rectifying channel, subfamily J, member 9 (KCNJ9), mRNA |
| 38 | | BC047580 | Plasma membrane Ca2+ transport ATPase 3, predicted to be involved in calcium transport, expressed predominantly in the brain |
| 107 | NM_174873 | AF260427 | Purinergic receptor P2X2, a cation channel gated by extracellular ATP that is involved in calcium ion transport and signal transduction |
| 65 | NM_130840 | AK055789 | ATPase (H+ transporting) lysosomal V0 subunit A isoform 4, non-catalytic accessory subunit 1B of the vacuolar proton pump |
| 44 | | AC004659 | Excitatory amino acid transporter 4 (solute carrier family 1 member 6), a high-affinity glutamate and aspartate transporter with ligand-gated chloride channel activity, likely regulates excitatory neurotransmission within the cerebellum |
| 74 | NM_017836 | AK000480 | Member of the divalent cation transporter family, which may transport Mg2+ or other divalent cations into the cell, has high similarity to uncharacterized human DKFZP434K0427 |
| | | | Putative kinase or kinase-interacting proteins |
| 48 | NM_032454 | L26260 | Serine threonine kinase 19, a manganese-dependent protein kinase that localizes mostly to the nucleus |
| 54 | | AK056549 | Membrane-associated guanylate kinase-interacting protein 1, protein with strong similarity to rat Maguin1, which contains SAM, PDZ, and PH domains and interacts with synaptic scaffolding kinases S-SCAM and PSD-95/SAP90 |

TABLE 6-continued

Informative genes for breast cancer - non-family (i) and (ii) genes

| Probe No. | Accession No. 1 | Accession No. 2 | Gene similarity and putative biological function |
|---|---|---|---|
| 66 | NM_003137 | BC038292 | Protein kinase for the serine- and arginine-rich (SR) family of RNA splicing factors, probably acts to control localization of the splicing factors within the nucleus; may play a role in determining sensitivity to cisplatin, a widely used anti-cancer agent |
| 78 | NM_015518 | BC056423 | Protein containing a protein kinase domain, has moderate similarity to a region of unc-51-like kinase 1 (mouse Ulk1), which is a protein kinase involved in the early steps of cerebellar granule cell neurite extension and may act in signaling cascades |
| 81 | NM_007061 | BC009356 | Marrow-stromal-endothelial serum constituent protein, contains a nonkinase CRIB (Cdc42/Rac interactive-binding) domain, binds CDC42 in a GTP-dependent manner, functions in cytoskeleton reorganization and possibly Rac protein signal transduction |
| 109 | NM_004125 | BC016319 | Guanine nucleotide-binding protein gamma subunit 10, putative component of heterotrimeric G protein complexes that are involved in signal transduction, interacts with G protein beta 1 (GNB1) and beta 2 (GNB2) and with murine kinase suppressor of Ras |
| | | | Metabolism |
| 7 | NM_000717 | M83670 | Carbonic anhydrase IV, catalyzes the reversible hydration of carbon dioxide to form bicarbonate and a proton, plays a role in pH regulation, may act in renal bicarbonate absorption, deficiency may be associated with pure proximal renal tubular acidosis |
| 22 | NM_153446 | AJ517771 | *Homo sapiens* beta 1,4 N-acetylgalactosaminyltransferase (GALGT2), mRNA |
| 102 | NM_001303 | U09466 | Heme A: farnesyltransferase, a farnesyltransferase required for the biosynthesis of heme A; deficiency or disruption of the gene may be associated with hereditary neuropathy with liability to pressure palsies and Charcot Marie Tooth disease type 1 |
| 108 | NM_130468 | BC023653 | Dermatan-4-sulfotransferase-1, catalyzes the transfer of a sulfate to the C-4 hydroxyl of N-acetylgalactosamine of dermatan in dermatan sulfate biosynthesis |
| | | | Cancer-related |
| 21 | NM_145897 | D89667 | Prefoldin 5, a component of the prefoldin chaperone complex involved in delivery of unfolded proteins to cytosolic chaperonin, interacts with and may repress activation of MYC; candidate tumor suppressor commonly substituted in cancer cells |
| 56 | NM_006136 | BC005338 | Capping protein Z-line (alpha 2), subunit of an actin-binding protein that may play a role in cell motility; corresponding gene is amplified in malignant gliomas and may be involved in tumorigenesis |
| 79 | NM_004728.1 | | DEAD-H (Asp-Glu-Ala-Asp/His) box polypeptide 21, an RNA helicase that is inhibited by the anticancer drug adriamycin, an RNA foldase that introduces an intramolecular secondary structure in ssRNA, an autoantigen in watermelon stomach disease |
| 83 | | AF010315 | *Homo sapiens* tumor protein p53 inducible protein 11 (TP53I11), mRNA |
| 84 | NM_033137 | X65779 | Fibroblast growth factor 1 (acidic), a mitogen and apoptosis inhibitor involved in cell migration, embryogenesis, organ development, and angiogenesis |
| 85 | NM_025216 | AK024363 | Wingless-type MMTV integration site family member 10a, member of the wnt family, may be involved in signal transduction and carcinogenesis; overproduced in some esophageal, gastric, and colorectal cancer |
| 93 | NM_021070 | AF318354 | Protein containing eight epidermal growth factor (EGF)-like domains and two TGF binding protein domains, has strong similarity to a region of latent transforming growth factor binding protein 3 (mouse Ltbp3) |
| 103 | NM_001550 | BC001272 | Protein with strong similarity to rat Rn.3723, which is induced by nerve growth factor (NGF), plays a role in muscle differentiation, and is expressed in proliferating and differentiating tissues |
| 104 | NM_198407 | U60179 | Growth hormone secretagogue receptor, a G protein-coupled receptor which binds ghrelin (GHRL) and synthetic growth hormone secretagogues, may regulate growth hormone secretion, elevated expression may be associated with endocrine tumors |
| 88 | NM_016041 | BC010890 | F-LAN-1, protein upregulated in hepatocarcinomas, involved in the positive regulation of cell proliferation |
| | | | Actin-related |
| 25 | NM_005731 | U50523 | Actin related protein 2/3 complex subunit 2, component of the Arp2/3 complex, which is involved in assembly of the actin cytoskeleton, interacts directly with ARPC4, possibly as an early intermediate in Arp2/3 complex formation |
| 98 | NM_006135 | BX648738 | Capping protein muscle Z-line alpha 1, an actin capping protein that regulates actin polymerization and may contribute to barbed-end actin capping, cell motility, sarcomere organization, and muscle function |
| 94 | NM_006136 | U03269 | *Homo sapiens* capping protein (actin filament) muscle Z-line, alpha 2 (CAPZA2), mRNA |
| | | | Cell differentiation |
| 39 | NM_001858 | U09279 | Alpha 1 subunit of type XIX collagen, member of the FACIT family of collagens, may be involved in cell differentiation; alternatively spliced in rhabdomyosarcoma cells |
| 50 | NM_006818 | AK056089 | ALL1-fused gene from chromosome 1q, protein expressed in thymus, hematopoietic and leukemic cell lines; corresponding gene is the site of chromosomal translocations involving MLL and resulting in acute myelomonocytic leukemia |
| 51 | NM_006168 | | NK homeobox family 6 A, a member of the homeodomain family of DNA binding proteins that regulate gene expression and participate in control of cell differentiation, contains highly conserved NK decapeptide and homeodomain regions |
| 92 | NM_001496 | AY359037 | GDNF family receptor alpha 3, a glycosylphosphatidylinositol (GPI)-linked orphan member of the GDNF/neurturin/persephin receptor family, highly expressed in the developing peripheral nervous system and in adult sensory and sympathetic ganglia |
| | | | Other functions |
| 46 | NM_016009 | AK001954 | SH3-domain GRB2-like endophilin B1, contains a Src homology 3 (SH3) domain in the C terminus and may act as a regulator of the BAX apoptotic signaling pathway |
| 89 | NM_021724 | M24898 | *Homo sapiens* nuclear receptor subfamily 1, group D, member 1 (NR1D1), mRNA |
| 96 | NM_006152 | U10485 | Lymphoid-restricted membrane protein, a membrane protein of the cytoplasmic side of the endoplasmic reticulum |

TABLE 6-continued

Informative genes for breast cancer - non-family (i) and (ii) genes

| Probe No. | Accession No. 1 | Accession No. 2 | Gene similarity and putative biological function |
|---|---|---|---|
| 90 | NM_016364 | BC009778 | Phosphatidylserine-specific phospholipase A1, hydrolyzes fatty acids at the sn-1 position of phosphatidylserine and 1-acyl-2-lysophosphatidylserine, plays a role in regulation of phosphatidylserine or lysophosphatidylserine-mediated functions |
| 87 | NM_015900 | BC047703 | Dual specificity phosphatase 13, may dephosphorylate phosphotyrosine, phosphoserine, and phosphothreonine residues, may play a role in regulation of meiosis and, or differentiation of testicular germ cells Unknown function |
| 9 | NM_018286 | AK095175 | Protein of unknown function |
| 12 | NM_013441 | AF176117 | Homo sapiens Down syndrome critical region gene 1-like 2 (DSCR1L2), mRNA |
| 14 | NM_148415 | | Protein with moderate similarity to SCA2 (Ataxin-2), which is associated with spinocerebellar ataxia type 2 |
| 15 | NM_017845 | BC015145 | Protein of unknown function, has high similarity to uncharacterized mouse D5Buc26e |
| 23 | NM_015702 | BC022859 | Protein of unknown function, has high similarity to uncharacterized mouse 2010311D03Rik |
| 30 | NM_173564 | AK124773 | Homo sapiens hypothetical protein FLJ37538 (FLJ37538), mRNA |
| 33 | NM_002336 | AK074543 | Homo sapiens low density lipoprotein receptor-related protein 6 (LRP6), mRNA |
| 36 | NM_152383 | BC036113 | Homo sapiens hypothetical protein MGC42174 (MGC42174), mRNA |
| 43 | NM_020141 | AF164793 | Protein of unknown function, has high similarity to uncharacterized C. elegans K07F5.15 |
| 57 | NM_004872 | BC016374 | Protein of unknown function, has strong similarity to uncharacterized mouse ORF18 |
| 59 | NM_003678 | AK025385 | Protein of unknown function, has very strong similarity to uncharacterized mouse Fmip |
| 62 | NM_004321 | BX537556 | Homo sapiens hypothetical protein BC009491 (LOC151568), mRNA |
| 64 | NM_152587 | BC029536 | Homo sapiens hypothetical protein MGC33948 (MGC33948), mRNA |
| 75 | | BC030200.1 | Protein of unknown function, has low similarity to uncharacterized mouse D430039N05Rik |
| 77 | NM_174918 | BC035847 | Homo sapiens hypothetical protein LOC199675 (LOC199675), mRNA |
| 82 | NM_174899 | BC033935 | Homo sapiens hypothetical protein LOC130888 (LOC130888), mRNA |
| 86 | NM_178525 | AY248901 | Homo sapiens hypothetical protein MGC33407 (MGC33407), mRNA |
| 99 | NM_025109 | AL133017 | Homo sapiens hypothetical protein FLJ22865 (FLJ22865), mRNA |
| 106 | NM_152362 | AK024161 | Homo sapiens hypothetical protein MGC17791 (MGC17791), mRNA |
| 110 | | XM_088567 | Unknown |
| 111 | NM_198458 | AK126727 | Unknown |
| 112 | | BC054888 | Unknown |

Accession numbers are as defined in Table 5

The invention claimed is:

1. A method of preparing a standard gene transcript pattern characteristic of breast cancer or a stage thereof in an organism comprising at least the steps of:
   a) isolating mRNA from the cells of a sample of one or more organisms having the cancer or stage thereof, which isolated mRNA may optionally be reverse transcribed to cDNA;
   b) hybridizing the mRNA or cDNA of step (a) to a set of oligonucleotide probes specific for breast cancer or a stage thereof in an organism and sample thereof corresponding to the organism and sample thereof under investigation, wherein said set comprises at least 10 oligonucleotides, but contains less than 1000 oligonucleotides, and wherein at least 10 oligonucleotides of said set are selected from:
   an oligonucleotide consisting of the sequence of any one of SEQ ID NOs: 113-146;
   an oligonucleotide consisting of a sequence entirely complementary to any one of SEQ ID NOs: 113-146;

an oligonucleotide listed in Table 3;
an oligonucleotide consisting of a sequence entirely complementary to an oligonucleotide listed in Table 3;
an oligonucleotide which consists of at least 20 consecutive nucleotides of any one of SEQ ID NOs: 113-146;
an oligonucleotide which consists of a sequence entirely complementary to at least 20 consecutive nucleotides of any one of SEQ ID NOs: 113-146;
an oligonucleotide which consists of at least 20 consecutive nucleotides of an oligonucleotide listed in Table 3; or
an oligonucleotide which consists of a sequence entirely complementary to at least 20 consecutive nucleotides of an oligonucleotide listed in Table 3;
an oligonucleotide which consists of a sequence which is at least 80% identical to any one of SEQ ID NOs. 113-146, or an oligonucleotide which consists of a sequence which is at least 80% identical to the sequence of at least 20 consecutive nucleotides of any one of SEQ ID NOs. 113-146;
an oligonucleotide which consists of a sequence which is at least 80% identical to the sequence entirely complementary to any one of SEQ ID NOs. 113-146, or an oligonucleotide which consists of a sequence which is at least 80% identical to the sequence entirely complementary to at least 20 consecutive nucleotides of any one of SEQ ID NOs. 113-146;
an oligonucleotide which consists of a sequence which is at least 80% identical to an oligonucleotide listed in Table 3, or an oligonucleotide which consists of a sequence which is at least 80% identical to the sequence of at least 20 consecutive nucleotides of an oligonucleotide listed in Table 3;
an oligonucleotide which consists of a sequence which is at least 80% identical to the sequence entirely complementary to an oligonucleotide listed in Table 3, or an oligonucleotide which consists of a sequence which is at least 80% identical to the sequence entirely complementary to the sequence of at least 20 consecutive nucleotides of an oligonucleotide listed in Table 3;

c) assessing the amount of mRNA or cDNA hybridizing to each of said probes to produce a characteristic pattern reflecting the level of gene expression of genes to which said oligonucleotides bind, in the sample with breast cancer or a stage thereof, thereby obtaining a standard gene transcript pattern characteristic of breast cancer or a stage thereof in an organism.

2. A method of preparing a test gene transcript pattern comprising at least the steps of:
a) isolating mRNA from the cells of a sample of said test organism, which isolated mRNA may optionally be reverse transcribed to cDNA;
b) hybridizing the mRNA or cDNA of step (a) to a set of oligonucleotides as defined in claim 1 specific for breast cancer or a stage thereof in an organism and sample thereof corresponding to the organism and sample thereof under investigation; and
c) assessing the amount of mRNA or cDNA hybridizing to each of said probes to produce said pattern reflecting the level of gene expression of genes to which said oligonucleotides bind, in said test sample, thereby obtaining a test gene transcript pattern.

3. A method of diagnosing or identifying or monitoring breast cancer or a stage thereof in an organism, comprising the steps of:

a) isolating mRNA from the cells of a sample of said organism, which isolated mRNA may optionally be reverse transcribed to cDNA;
b) hybridizing the mRNA or cDNA of step (a) to a set of oligonucleotides as defined in claim 1 specific for breast cancer or a stage thereof in an organism and sample thereof corresponding to the organism and sample thereof under investigation;
c) assessing the amount of mRNA or cDNA hybridizing to each of said probes to produce a characteristic pattern reflecting the level of gene expression of genes to which said oligonucleotides bind, in said sample; and
d) comparing said pattern to a standard diagnostic pattern prepared according to the method of claim 1 using a sample from an organism corresponding to the organism and sample under investigation to determine the presence of breast cancer or a stage thereof in the organism under investigation.

4. The method as claimed in claim 1, wherein said set comprises a combination of oligonucleotides from family (i) and family (ii),
wherein an oligonucleotide from family (i) is selected from:
an oligonucleotide having the nucleotide sequence of a gene sequence from a gene encoding a protein involved in protein synthesis and/or stability;
an oligonucleotide having a nucleotide sequence which is entirely complementary to the nucleotide sequence of a gene sequence from a gene encoding a protein involved in protein synthesis and/or stability;
an oligonucleotide which consists of at least 20 consecutive nucleotides of a gene sequence from a gene encoding a protein involved in protein synthesis and/or stability;
an oligonucleotide which consists of a sequence entirely complementary to at least 20 consecutive nucleotides of a gene sequence from a gene encoding a protein involved in protein synthesis and/or stability;
an oligonucleotide having the nucleotide sequence which is at least 80% identical to the sequence of the gene sequence from a gene encoding a protein involved in protein synthesis and/or stability;
an oligonucleotide having the nucleotide sequence which is at least 80% identical to the sequence entirely complementary to the gene sequence from a gene encoding a protein involved in protein synthesis and/or stability;
an oligonucleotide which consists of a sequence which is at least 80% identical to the sequence of at least 20 consecutive nucleotides of the gene sequence from a gene encoding a protein involved in protein synthesis and/or stability; or
an oligonucleotide which consists of a sequence which is at least 80% identical to the sequence entirely complementary to at least 20 consecutive nucleotides of the gene sequence from a gene encoding a protein involved in protein synthesis and/or stability;
and wherein an oligonucleotide from family (ii) is selected from:
an oligonucleotide having the nucleotide sequence of a gene sequence from a gene encoding a protein involved in the regulation of defense and/or chromatin remodeling;
an oligonucleotide having a nucleotide sequence which is entirely complementary to the nucleotide sequence of a gene sequence from a gene encoding a protein involved in the regulation of defense and/or chromatin remodeling;

an oligonucleotide which consists of at least 20 consecutive nucleotides of a gene sequence from a gene encoding a protein involved in the regulation of defense and/or chromatin remodeling;

an oligonucleotide which consists of a sequence entirely complementary to at least 20 consecutive nucleotides of a gene encoding a protein involved in the regulation of defense and/or chromatin remodeling;

an oligonucleotide having the nucleotide sequence which is at least 80% identical to the gene sequence from a gene encoding the protein involved in the regulation of defense and/or chromatin remodeling;

an oligonucleotide having the nucleotide sequence which is at least 80% identical to the nucleotide sequence entirely complementary to the gene sequence from a gene encoding the protein involved in the regulation of defense and/or chromatin remodeling;

an oligonucleotide which consists of a sequence which is at least 80% identical to the sequence of at least 20 consecutive nucleotides of the gene sequence of a gene encoding the protein involved in the regulation of defense and/or chromatin remodeling; and an oligonucleotide which consists of a sequence which is at least 80% identical to the sequence entirely complementary to at least 20 consecutive nucleotides of the gene sequence of a gene encoding the protein involved in the regulation of defense and/or chromatin remodeling.

5. The method as claimed in claim 4, wherein said family (i) gene encoding a protein involved in protein synthesis and/or stability is selected from the group consisting of:
(a) a gene encoding a ribosomal protein or ribosomal activation protein; and
(b) a gene encoding a translation inhibition factor, a translation initiation factor, or an IE transcription factor.

6. The method as claimed in claim 4, wherein said family (ii) gene encoding a protein involved in the regulation of defense and/or chromatin remodelling family is selected from the group consisting of:
(a) a gene encoding an immune response related protein;
(b) a gene encoding a TNF-induced protein;
(c) a gene encoding a hypoxia-induced protein;
(d) a gene encoding an oxidative stress protein; and
(e) a gene encoding a protein involved in chromatin remodeling.

7. The method as claimed in claim 6, wherein:
(i) said immune response related protein is a cytokine, wherein said cytokine is an interleukin or a receptor thereof or a tumour necrosis factor or a receptor thereof or tumor necrosis factor superfamily member or a receptor thereof; and/or
(ii) said immune response protein is an adhesion protein selected from the group consisting of CD1A, CD1C, CD1D, CD3Z, 6, 8, 11, 14, 18, 24, 27, 28, 29, 40, 44, 50, 54, 59, 74, 79B, 80, 81, 83, 86, 96 and ICAM; and/or
(iii) said immune response related protein is an immunoglobulin component which is a heavy chain or Fc fragment; and/or
(iv) said immune response related protein is a growth factor, wherein said growth factor is endothelial cell growth factor or erythropoietin.

8. The method as claimed in claim 6, wherein said protein encoded by family (ii) gene is selected from the group consisting of an adhesion protein, interleukin, interleukin receptor, interleukin receptor superfamily member, TNF; TNF receptor or TNF receptor superfamily member, immunoglobulin component and erythropoietin.

9. The method as claimed in claim 4, wherein the gene encoding by family (i) is down-regulated in breast cancer versus normal patients, and wherein the gene encoding family (ii) is up-regulated in breast cancer versus normal patients.

10. The method as claimed in claim 1 wherein said probes correspond to genes which are systemically affected by breast cancer or a stage thereof.

11. The method as claimed in claim 1, wherein said gene is constitutively moderately or highly expressed.

12. The method as claimed in claim 5, wherein said set of oligonucleotides includes oligonucleotides from group (a).

13. The method as claimed in claim 1, wherein said set includes oligonucleotides from a gene encoding one or more ribosomal protein, and optionally a gene encoding one or more histone, and optionally a gene encoding ferritin.

14. The method as claimed in claim 1, wherein each oligonucleotide probe is selected from:
an oligonucleotide consisting of the sequence of any one of SEQ ID NOs: 113-146;
an oligonucleotide consisting of a sequence entirely complementary to any one of SEQ ID NOs: 113-146;
an oligonucleotide which consists of at least 20 consecutive nucleotides of any one of SEQ ID NOs: 113-146;
an oligonucleotide which consists of a sequence entirely complementary to at least 20 consecutive nucleotides of any one of SEQ ID NOs: 113-146;
an oligonucleotide which consists of a sequence which is at least 80% identical to any one of SEQ ID NOs. 113-146, or an oligonucleotide which consists of a sequence which is at least 80% identical to at least 20 consecutive nucleotides of any one of SEQ ID NOs. 113-146; and
an oligonucleotide which consists of a sequence which is at least 80% identical to the sequence entirely complementary to any one of SEQ ID NOs. 113-146, or an oligonucleotide which consists of a sequence which is at least 80% identical to the sequence entirely complementary to at least 20 consecutive nucleotides of any one of SEQ ID NOs. 113-146.

15. The method as claimed in claim 1, wherein each oligonucleotide probe is selected from:
an oligonucleotide listed in Table 3;
an oligonucleotide consisting of a sequence entirely complementary to an oligonucleotide listed in Table 3;
an oligonucleotide which consists of at least 20 consecutive nucleotides of an oligonucleotide listed in Table 3;
an oligonucleotide which consists of a sequence entirely complementary to at least 20 consecutive nucleotides of an oligonucleotide listed in Table 3;
an oligonucleotide which consists of a sequence which is at least 80% identical to an oligonucleotide listed in Table 3, or an oligonucleotide which consists of a sequence which is at least 80% identical to at least 20 consecutive nucleotides of an oligonucleotide listed in Table 3; and
an oligonucleotide which consists of a sequence which is at least 80% identical to the sequence entirely complementary to an oligonucleotide listed in Table 3, or an oligonucleotide which consists of a sequence which is at least 80% identical to the sequence entirely complementary to at least 20 consecutive nucleotides of an oligonucleotide listed in Table 3.

16. The method as claimed in claim 1, wherein said set additionally comprises one or more oligonucleotide probes selected from:

an oligonucleotide listed in Table 4;
an oligonucleotide consisting of a sequence entirely complementary to an oligonucleotide listed in Table 4;
an oligonucleotide which consists of at least 20 consecutive nucleotides of an oligonucleotide listed in Table 4;
an oligonucleotide which consists of a sequence entirely complementary to at least 20 consecutive nucleotides of an oligonucleotide listed in Table 4;
an oligonucleotide which consists of a sequence which is at least 80% identical to an oligonucleotide listed in Table 4;
an oligonucleotide consisting of a sequence which is at least 80% identical to the sequence entirely complementary to an oligonucleotide listed in Table 4;
an oligonucleotide which consists of a sequence which is at least 80% identical to the sequence of at least 20 consecutive nucleotides of an oligonucleotide listed in Table 4; and
an oligonucleotide which consists of a sequence which is at least 80% identical to the sequence entirely complementary to at least 20 consecutive nucleotides of an oligonucleotide listed in Table 4.

17. The method as claimed in claim 1, wherein said set consists of from 10 to 500 probes.

18. The method as claimed in claim 1, wherein said set of probes are immobilized on one or more solid supports.

19. The method as claimed in claim 1, wherein said cells are not disease cells, have not contacted disease cells and do not originate from the site of disease.

20. The method as claimed in claim 1, wherein said sample is obtained from a site distant to the site of disease.

21. The method as claimed in claim 1, wherein said sample is tissue, body fluid or body waste.

22. The method as claimed in claim 21, wherein said sample is peripheral blood.

23. The method as claimed in claim 1, wherein said organism is a mammal.

24. A set of oligonucleotide probes as defined in claim 1, wherein said probe set contains less than 300 probes.

25. A kit for performing a method as claimed in claim 1 comprising a set of oligonucleotide probes as defined in claim 24 immobilized on one or more solid supports.

26. The kit as claimed in claim 25, additionally comprising a package insert detailing how the method should be performed.

27. A method of preparing a standard gene transcript pattern characteristic of breast cancer or a stage thereof in an organism comprising at least the steps of:
a) releasing target polypeptides from a sample of one or more organisms having breast cancer or a stage thereof;
b) contacting said target polypeptides with one or more binding partners, wherein each binding partner is specific to a marker polypeptide (or a fragment thereof) encoded by the gene to which an oligonucleotide as defined in claim 1 binds, to allow binding of said binding partners to said target polypeptides, wherein said marker polypeptides are specific for breast cancer in an organism and sample thereof corresponding to the organism and sample thereof under investigation; and
c) assessing the target polypeptide binding to said binding partners to produce a characteristic pattern reflecting the level of gene expression of genes which express said marker polypeptides, in the sample with breast cancer or a stage thereof, thereby obtaining a standard gene transcript pattern characteristic of breast cancer or a stage thereof in an organism.

28. A method of preparing a test gene transcript pattern comprising at least the steps of:
a) releasing target polypeptides from a sample of said test organism;
b) contacting said target polypeptides with one or more binding partners, wherein each binding partner is specific to a marker polypeptide (or a fragment thereof) encoded by the gene to which an oligonucleotide as defined in claim 1 binds, to allow binding of said binding partners to said target polypeptides, wherein said marker polypeptides are specific for breast cancer in an organism and sample thereof corresponding to the organism and sample thereof under investigation; and
c) assessing the target polypeptide binding to said binding partners to produce a characteristic pattern reflecting the level of gene expression of genes which express said marker polypeptides, in said test sample, thereby obtaining a test gene transcript pattern.

29. A method of diagnosing or identifying or monitoring breast cancer or a stage thereof in an organism comprising the steps of:
a) releasing target polypeptides from a sample of said organism;
b) contacting said target polypeptides with one or more binding partners, wherein each binding partner is specific to a marker polypeptide (or a fragment thereof) encoded by the gene to which an oligonucleotide as defined in claim 1 binds, to allow binding of said binding partners to said target polypeptides, wherein said marker polypeptides are specific for breast cancer in an organism and sample thereof corresponding to the organism and sample thereof under investigation; and
c) assessing the target polypeptide binding to said binding partners to produce a characteristic pattern reflecting the level of gene expression of genes which express said marker polypeptides in said sample; and
d) comparing said pattern to a standard diagnostic pattern prepared according to the method of claim 26 using a sample from an organism corresponding to the organism and sample under investigation to determine the degree of correlation indicative of the presence of breast cancer or a stage thereof in the organism under investigation.

30. The method as claimed in claim 5, wherein said ribosomal protein or ribosomal activation protein is selected from the group consisting of L1-L56, L7A, L10A, L13A, L18A, L23A, L27A, L35A, L36A, L37A, P0, P1, P2, S2-S29, S31, S33-S36, S3A, S15A, S18A, S18B, S18C, S27A, 63, 115, a pseudogene, ribosomal protein kinase, ribonuclease, putative S1 RNA binding domain protein, eukaryotic translation initiation factor and guanine nucleotide binding protein G.

31. The method as claimed in claim 5, wherein said translation inhibition factor or translation inhibition factor is selected from the group consisting of an eukaryotic translation elongation factor, tRNA synthetase, RNA binding protein, polyadenylation element binding protein, tyrosine phosphatase, eukaryotic translation initiation factor and RNA polymerase I.

32. The method as claimed in claim 5, wherein said another modulator of transcription or translation is a cyclin D-type binding protein or guanine nucleotide binding protein.

33. The method as claimed in claim 6, wherein said immune response recited protein is selected from the group consisting of a T-cell receptor, T-cell receptor associated component, a cytokine, an interferon regulatory factor, oncostatin M, Leukemia inhibitory factor, chemokine ligand, chemokine receptor family member, a complement component, an interferon stimulated factor, MHC class I or II (or related components), an adhesion protein, nuclear factor of kappa polypeptide gene enhancer in B-cells, myelin basic protein, cathepsin, toll-like receptor, a proteosome subunit, ferritin, a protein kinase, protein phosphatase, activator protein kinase, activator protein phosphatase, inhibitor protein kinase, inhibitor protein phosphatase, leukocyte immunoglobulin-like receptor, an immunoglobulin component, defensin, oxytocin, S100 calcium binding protein, lectin, a lectin receptor, a lectin superfamily member, leptin, phospholipase and a growth factor.

34. The method as claimed in claim 6, wherein the gene encoding a TNF-induced protein is selected from the group consisting of TNF alpha-induced protein 8, inhibitor of kappa light polypeptide gene enhancer in B-cells, TNF-associated factor 2, TNF-associated factor 5, nuclear factor of kappa light polypeptide gene enhancer in B-cells, a MAP kinase, protein kinase C, ubiquitous kinase, cadherin, caspase, cyclin DI, superoxide dismutase and an interleukin.

35. The method as claimed in claim 6, wherein the gene encoding a hypoxia-induced protein is selected from the group consisting of sestrin, integrin, EIA binding protein p300, endothelin, ataxia telangiectasia and Rad3 related protein, hexokinase 2, TEK tyrosine kinase, DNA fragmentation factor, caspase, plasminogen activator, hypoxia-inducible factor 1 and glucose phosphate isomerase.

36. The method as claimed in claim 6, wherein an oxidative stress protein is selected from the group consisting of superoxide dismutase, glutathione synthetase, catalase, lactoperoxidase, thyroid peroxidase, myeloperoxidase, eosinophil peroxidase, oxidation resistance 1, peroxiredoxin, cytochrome P450, scavenger receptor, paraoxonase, glutathione reductase, NAD(P)H dehydrogenase, glutathione S-transferase, catenin, glutaredoxin, a heat shock protein, mitogen-activated protein kinases, enolase, thioredoxin reductase and peroxiredoxin.

37. The method of claim 6, wherein said protein involved in chromatin remodelling is a histone replacement protein.

38. The method as claimed in claim 7, wherein said interleukin is selected from the group consisting of DL-1, DL-2, DL-3, DL-4, DL-5, DL-6, DL-7, DL-8, DL-9, DL-10, DL-11, DL-12, DL-13, DL-15, DL-17, DL-18, DL-20, DL-22 and DL-24.

39. The method as claimed in claim 7, wherein said tumor necrosis factor is selected from the group consisting of tumor necrosis factor 2, tumor necrosis factor 3, tumor necrosis factor 4, tumor necrosis factor 5, tumor necrosis factor 6, tumor necrosis factor 7, tumor necrosis factor 8, tumor necrosis factor 9, tumor necrosis factor 11, tumor necrosis factor 12, tumor necrosis factor 13, tumor necrosis factor 14 and tumor necrosis factor 15.

40. The method as claimed in claim 7, wherein said immunoglobulin is a heavy chain or Fc fragment of IgG, IgE or IgA or a superfamily member thereof.

41. The method as claimed in claim 23, wherein said organism is a human.

42. The set of oligonucleotide probes as claimed in claim 24, wherein said set additionally comprises one or more oligonucleotide probes selected from:
an oligonucleotide listed in Table 4;
an oligonucleotide consisting of a sequence entirely complementary to an oligonucleotide listed in Table 4;
an oligonucleotide which consists of at least 20 consecutive nucleotides of an oligonucleotide listed in Table 4;
an oligonucleotide which consists of a sequence entirely complementary to at least 20 consecutive nucleotides of an oligonucleotide listed in Table 4;
an oligonucleotide which consists of a sequence which is at least 80% identical to an olignucleotide listed in Table 4;
an oligonucleotide consisting of a sequence which is at least 80% identical to the sequence entirely complementary to an oligonucleotide listed in Table 4;
an oligonucleotide which consists of a sequence which is at least 80% identical to the sequence of at least 20 consecutive nucleotides of an oligonucleotide listed in Table 4; and
an oligonucleotide which consists of a sequence which is at least 80% identical to the sequence which is entirely complementary to the sequence of at least 20 consecutive nucleotides of an oligonucleotide listed in Table 4.

43. The method as claimed in claim 1, 2 or 3, wherein said set of oligonucleotides is randomly selected from an oligonucleotide consisting of the sequence of any one of SEQ ID NOs: 113-146, or an oligonucleotide listed in Table 3, wherein each oligonucleotide may be replaced with an oligonucleotide selected from the following:
an oligonucleotide consisting of a sequence entirely complementary to any one of SEQ ID NOs: 113-146;
an oligonucleotide consisting of a sequence entirely complementary to an oligonucleotide listed in Table 3;
an oligonucleotide which consists of at least 20 consecutive nucleotides of any one of SEQ ID NOs: 113-146;
an oligonucleotide which consists of a sequence entirely complementary to at least 20 consecutive nucleotides of any one of SEQ ID NOs: 113-146;
an oligonucleotide which consists of at least 20 consecutive nucleotides of an oligonucleotide listed in Table 3;
an oligonucleotide which consists of a sequence entirely complementary to at least 20 consecutive nucleotides of an oligonucleotide listed in Table 3;
an oligonucleotide which consists of a sequence which is at least 80% identical to any one of SEQ ID NOs. 113-146, or an oligonucleotide which consists of a sequence which is at least 80% identical to the sequence of at least 20 consecutive nucleotides of any one of SEQ ID NOs. 113-146;
an oligonucleotide which consists of a sequence which is at least 80% identical to the sequence entirely complementary to the sequence of any one of SEQ ID NOs. 113-146, or an oligonucleotide which consists of a sequence which is at least 80% identical to the sequence entirely complementary to the sequence of at least 20 consecutive nucleotides of any one of SEQ ID NOs. 113-146;
an oligonucleotide which consists of a sequence which is at least 80% identical to an oligonucleotide listed in Table 3, or an oligonucleotide which consists of a sequence which is at least 80% identical to the sequence of at least 20 consecutive nucleotides of an oligonucleotide listed in Table 3; and
an oligonucleotide which consists of a sequence which is at least 80% identical to the sequence entirely complementary to an oligonucleotide listed in Table 3, or an oligonucleotide which consists of a sequence which is at least 80% identical to the sequence entirely complementary to at least 20 consecutive nucleotides of an oligonucleotide listed in Table 3.

44. The method as claimed in claim 1, 2 or 3 wherein said set comprises oligonucleotides consisting of the sequences of SEQ ID NOs: 113-146 and all the oligonucleotides listed in Table 3, wherein each oligonucleotide may be replaced with an oligonucleotide selected from the following:
an oligonucleotide consisting of a sequence entirely complementary to any one of SEQ ID NOs: 113-146;

an oligonucleotide consisting of a sequence entirely complementary to an oligonucleotide listed in Table 3;

an oligonucleotide which consists of at least 20 consecutive nucleotides of any one of SEQ ID NOs: 113-146;

an oligonucleotide which consists of a sequence entirely complementary to at least 20 consecutive nucleotides of any one of SEQ ID NOs: 113-146;

an oligonucleotide which consists of at least 20 consecutive nucleotides of an oligonucleotide listed in Table 3;

an oligonucleotide which consists of a sequence entirely complementary to at least 20 consecutive nucleotides of an oligonucleotide listed in Table 3;

an oligonucleotide which consists of a sequence which is at least 80% identical to any one of SEQ ID NOs. 113-146, or an oligonucleotide which consists of a sequence which is at least 80% identical to the sequence of at least 20 consecutive nucleotides of any one of SEQ ID NOs. 113-146;

an oligonucleotide which consists of a sequence which is at least 80% identical to the sequence entirely complementary to the sequence of any one of SEQ ID NOs. 113-146, or an oligonucleotide which consists of a sequence which is at least 80% identical to the sequence entirely complementary to at least 20 consecutive nucleotides of any one of SEQ ID NOs. 113-146;

an oligonucleotide which consists of a sequence which is at least 80% identical to an oligonucleotide listed in Table 3, or an oligonucleotide which consists of a sequence which is at least 80% identical to the sequence of at least 20 consecutive nucleotides of an oligonucleotide listed in Table 3; and an oligonucleotide which consists of a sequence which is at least 80% identical to the sequence entirely complementary to an oligonucleotide listed in Table 3, or an oligonucleotide which consists of a sequence which is at least 80% identical to the sequence entirely complementary to at least 20 consecutive nucleotides of an oligonucleotide listed in Table 3.

45. The method as claimed in claim 43, wherein said set additionally comprises all of the oligonucleotides listed in Table 4 wherein each oligonucleotide may be replaced with an oligonucleotide selected from the following:

an oligonucleotide consisting of a sequence entirely complementary to an oligonucleotide listed in Table 4;

an oligonucleotide which consists of at least 20 consecutive nucleotides of an oligonucleotide listed in Table 4;

an oligonucleotide which consists of a sequence entirely complementary to at least 20 consecutive nucleotides of an oligonucleotide listed in Table 4;

an oligonucleotide which consists of a sequence which is at least 80% identical to an olignucleotide listed in Table 4;

an oligonucleotide consisting of a sequence which is at least 80% identical to the sequence entirely complementary to an oligonucleotide listed in Table 4;

an oligonucleotide which consists of a sequence which is at least 80% identical to the sequence of at least 20 consecutive nucleotides of an oligonucleotide listed in Table 4; and an oligonucleotide which consists of a sequence which is at least 80% identical to the sequence entirely complementary to at least 20 consecutive nucleotides of an oligonucleotide listed in Table 4.

46. The method as claimed in claim 44, wherein said set additionally comprises all of the oligonucleotides listed in Table 4 wherein each oligonucleotide may be replaced with an oligonucleotide selected from the following:

an oligonucleotide consisting of a sequence entirely complementary to an oligonucleotide listed in Table 4;

an oligonucleotide which consists of at least 20 consecutive nucleotides of an oligonucleotide listed in Table 4;

an oligonucleotide which consists of a sequence entirely complementary to at least 20 consecutive nucleotides of an oligonucleotide listed in Table 4;

an oligonucleotide consisting of a sequence which is at least 80% identical to the sequence entirely complementary to an oligonucleotide listed in Table 4;

an oligonucleotide which consists of a sequence which is at least 80% identical to the sequence of at least 20 consecutive nucleotides of an oligonucleotide listed in Table 4; and an oligonucleotide which consists of a sequence which is at least 80% identical to the sequence entirely complementary to at least 20 consecutive nucleotides of an oligonucleotide listed in Table 4.

47. The method as claimed in claim 6, wherein said set of oligonucleotides includes oligonucleotides from groups a and e.

48. The method as claimed in claim 1, 2, 3, 16, 17, 18, 22, 41, 45 or 46 wherein said 10 oligonucleotides bind to 10 different transcripts.

49. The set of oligonucleotide probes as claimed in claim 24, 25 or 42 wherein said 10 oligonucleotides bind to 10 different transcripts.

* * * * *